(12) United States Patent
Pirat et al.

(10) Patent No.: US 8,383,609 B2
(45) Date of Patent: Feb. 26, 2013

(54) PHOSPHORUS CONTAINING HETEROCYCLIC COMPOUNDS, SUGAR ANALOGUES, AND COMPOSITIONS HAVING ANTI-CANCER ACTIVITY CONTAINING THE SAME

(75) Inventors: Jean-Luc Pirat, Saint-Aunes (FR); David Virieux, Montpellier (FR); Ludovic Clarion, Saint Gely du Fesc (FR); Jean-Noël Volle, Montpellier (FR); Norbert Bakalara, Saint Martin de Londres (FR); Marcel Mersel, Montpellier (FR); Jerôme Montbrun, Chuzelles (FR); Henri-Jean Cristau, Saint-Aunes (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/667,798

(22) PCT Filed: Jul. 7, 2008

(86) PCT No.: PCT/EP2008/058788
§ 371 (c)(1),
(2), (4) Date: Jul. 28, 2010

(87) PCT Pub. No.: WO2009/004096
PCT Pub. Date: Jan. 8, 2009

(65) Prior Publication Data
US 2010/0298272 A1    Nov. 25, 2010

Related U.S. Application Data

(60) Provisional application No. 60/948,143, filed on Jul. 5, 2007.

(51) Int. Cl.
*A61K 31/665* (2006.01)
*C07F 9/06* (2006.01)
*C07F 9/02* (2006.01)
*A61P 35/00* (2006.01)

(52) U.S. Cl. ............. 514/100; 514/99; 549/220; 558/82

(58) Field of Classification Search .................. None
See application file for complete search history.

(56) References Cited

FOREIGN PATENT DOCUMENTS

| WO | WO 98/31697 A1 | 7/1998 |
| WO | WO 01/27128 A1 | 4/2001 |

OTHER PUBLICATIONS

Sorensen et al., Phosphinamides and Phosphonamides, Novel Series of Potent Matrix Metalloproteinase Inhibitors with Antitumour Activity, 11 Bioorg. & Med. Chem. 5461-84 (2003).*
Fuhrhop & Gustav Penzlin, Organic Synthesis: Concepts, Methods, Starting Materials 157 (VCH Publishers, Inc., 2d ed. 1994).*
Thiem & Guenther, Abramov Reaction of Carbohydrate Derivatives with Free Anomeric Centers, 20(1) Phosphorus & Sulfur & The Related Elements 67-79 (1984) (CAS Abstract).*
Hanessian et al., Synthesis of Carbohydrate Phostones as Potential Glycomimetics, 4(23) Bioorg. & Med. Chem. Letts. 2763-8 (1994) (CAS Abstract).*
Richard B. Silverman, The Organic Chemistry of Drug Design and Drug Action, Chapter 2: Drug Discovery, Design, and Development, Academic Press, p. 5-51 (1992).*
International Search Report, dated Oct. 16, 2008, from corresponding PCT application.
Henri-Jean Cristau et al., "First synthesis of P-aryl-phosphinosugars, organophosphorus analogues of C-arylglycosides", Tetrahedron Letters, 2005, pp. 3741-3744, vol. 46, Elsevier Ltd.

* cited by examiner

*Primary Examiner* — Nizal S Chandrakumar
*Assistant Examiner* — Timothy R Rozof
(74) *Attorney, Agent, or Firm* — Young & Thompson

(57) ABSTRACT

A new anticancer compounds of formula (1) Drugs and pharmaceutical compositions to be used in human or veterinary medicine, which include at least one compound of formula (1). A method of treating and/or preventing cancer in a human or an animal using the compound of formula (1)

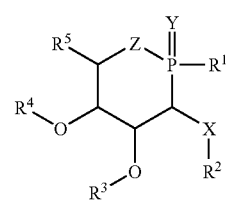

(1)

20 Claims, 1 Drawing Sheet

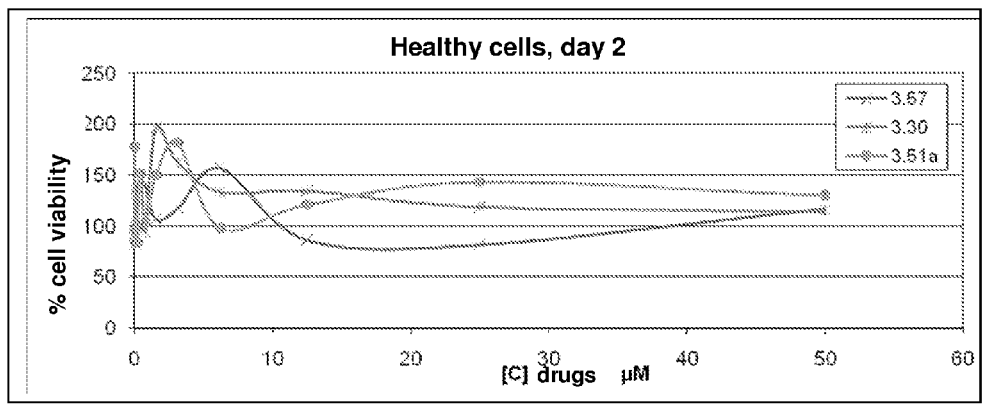

PHOSPHORUS CONTAINING HETEROCYCLIC COMPOUNDS, SUGAR ANALOGUES, AND COMPOSITIONS HAVING ANTI-CANCER ACTIVITY CONTAINING THE SAME

BACKGROUND OF THE INVENTION

1. Field of the Invention

The present invention relates to the field of therapeutic treatment of human or animal cancer. The present invention relates in particular to a family of phosphorus containing carbohydrate analogues comprising a phosphinane ring, and prophylactic or therapeutic pharmaceutical compositions for use in human or veterinary medicine.

2. Description of Related Art

According to recent statistics, cancer is the second cause of death in France after cardiovascular diseases. The measures taken to fight against cancerous diseases do require multiplying the early diagnoses, but also improving the drug treatments. Discovering new original molecules, the specificity for tumoral cells of which as compared to healthy cells would be complete, would enable to develop new therapies.

Prior to choosing a therapy against cancer, some parameters have to be considered: the cancer type (sarcoma, melanoma . . . ), the affected organ, the cancer evolution stage, the whole prognostic factors and the patient own characteristics (age, global health status, psychism . . . ). From these data, a therapy may be selected, whether locally or globally. The most efficient treatments are local therapies that combine surgical and/or radiotherapeutic methods. They do treat less developed affections and heal most of localized cancers. General therapies, i.e. chemotherapy and/or hormonotherapy are typically palliative or auxiliary treatments. These treatments are implemented for localized and more developed cancers that may result in complicated metastases not yet clinically revealed. They make it possible to heal a limited number of generalized cancers but do improve the life expectancy of the patients (see Capdeville R., Buchdunger E., Zimmermann J., Matter A., Nature Rev. Drug Discov., 2002, 1, 493; Eisenberg B. L., Von Mehren M., Expert Opin Pharmacother., 2003, 6, 869; Gilman A., Philips F. S., Science, 1946, 103, 409; Gingras D, Beliveau R. Med. Sci., 1997. 13, 1428-35).

The limitation concerning the use of known antitumoral drugs results from their high toxicity, which causes many various side effects that might even lead to the patient death. "Chemical weapons" used for treating cancer are supposed to kill the tumoral cells while preserving the healthy cells. However the selectivity still remains highly relative as most of the drugs that are used in chemotherapy do present a non negligible haematological toxicity. Reducing the harmful side effects, especially those having serious consequences on the medical and psychic level, is as much important as attempting to improve the efficiency of a given drug. Taken all round, the whole range of drugs of the actual chemotherapist still comprises old highly cytotoxic drugs, as most of known antitumoral drugs are already more than about ten years old, and are very poorly targeted, at least on cellular level and do not offer any alternative to the resistance phenomena. Therefore there is a need for new antitumoral molecules, that can be used in chemotherapy, and that most preferably would only target the tumoral cells.

Sugars, which represent a family of biomolecules being omnipresent in the living world and comprising lots of different structures and functions, have many therapeutic applications: they aid fighting against obesity, diabetes, but also act as antivirus, antibiotic and antitumoral agents. Sugar analogue synthesis is interesting as these compounds may interfere with the various receptors or enzymes that do imply sugars, especially the energetic or biosynthetic mechanisms of some molecules, glycoconjugates, as well as the cell interadhesion mechanisms.

In the field of carbohydrate cyclic analogue preparation, two main axes have already been developed: The substitution of a carbon moiety for the hydroxyl group at the anomeric position (C-arylglycosides), and the substitution of another heteroatom for the intracyclic oxygen atom (phosphosugars, phosphasugars, iminosugars, thioglycosides).

C-aryl glycosides have demonstrated various biological activities and are largely used for treating diabetes, especially the type II diabetes, obesity or atherosclerosis.

The first family of cyclic phosphorus containing analogues of sugars that was synthesized was the phosphosugar family, by Wang and Whistler in 1968. These researchers described the preparation of a D-xylopyranose phosphinic analogue, i.e. 5-phospha-D-xylose (Whistler, R. L.; Wang, C. -C. *Journal of Organic chemistry* 1968, 33, 2495-2497 and 4455-4458).

There are two known phosphosugar families: the phosphonosugars, also known as phostones, and the phosphinosugars. The phosphinosugar family standing half-way between C-aryl-glycosides and phosphonosugars did not arouse much attention. The structures of the compounds that are representative of such large families are given in the scheme hereunder, wherein R represents an aryl or an alkyl group and R' represents an aryl, alkyl, alkoxy or aryloxy group:

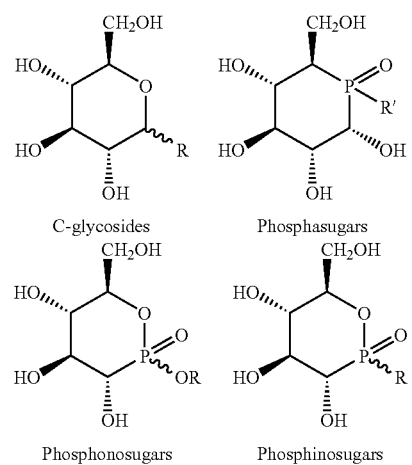

The two first phosphinosugars have been described in furanosic compound series in 2003 in Bisseret, P.; Boiteau, J. G.; Eustache, J. *Tetrahedron Lett.* 2003, 44, 2351-2354. Since then, two other compounds of this family have been prepared in pyranose compound series in Cristau, H. -J., Monbrun, J., Schleiss, J., Virieux, D., Pirat, J. -L., Tetrahedron Lett., 2005, 46, 3741-3744. However, nothing was mentioned concerning any particular biological activity for these phosphinosugars. The structures of known phosphinosugars are presented in the scheme hereafter:

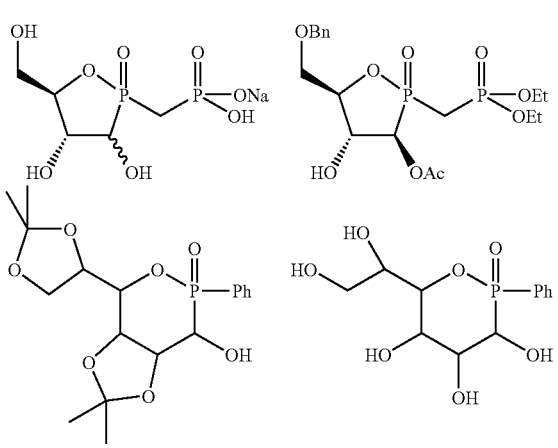

Now the present inventors discovered that new sugar analogue, heterocyclic phosphonic compounds have a cytotoxic activity on tumoral cell mimetics, without any cytotoxicity against healthy cells. As used herein, healthy cells mean non-tumor cells.

SUMMARY OF THE INVENTION

The present invention relates to new compounds with an anti-cancer activity having the following formula (1), that will hereafter be called phosphinosugars in the context of the present invention:

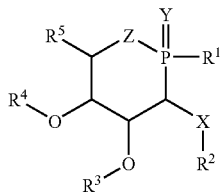

(1)

wherein:

Y represents an oxygen, a sulfur or a selenium atom, preferably an oxygen atom,

Z represents O, S, Se, NH or a $NR^6$ group, wherein $R^6$ is an aryl or an optionally substituted alkyl group, preferably an oxygen atom, $R^1$ represents a hydrogen atom, an optionally substituted alkyl group or an aryl group, X represents an oxygen, a sulfur, a selenium atom, a NH or $NR^7$ group, $R^7$ being an optionally substituted aryl or alkyl group; X preferably represents O or NH, and;

$R^2$ represents an aryl optionally substituted alkyl group, a hydrogen atom, a trichloroacetimidate group (—C(=NH) $CCl_3$), an acyl, formyl, sulfonyl, sulfinyl, tert-butyldiphenylsilyl, allyl group, a saccharyl, ester, amide, thioamide, sulfonamide group, or X—$R^2$ represents a $P(O)R^{2'}R^{6'}$ group, in which $R^{2'}$ and $R^{6'}$ represent independently from each other an aryl group, an optionally substituted alkyl group, OH, an alkoxy or an aryloxy group, $R^3$ and $R^4$ represent independently from each other an aryl, an optionally substituted alkyl group, an hydrogen atom, a trichloroacetimidate group, an acyl, formyl, sulfonyl, sulfinyl, tert-butyldiphenylsilyl group, an allyl, ester, amide, thioamide, sulfonamide group, or $R^3$ and $R^4$ taken together form a divalent radical of formula —$R^3$—$R^4$—, wherein —$R^3$—$R^4$— preferably represents an isopropylidene, benzylidene, diphenyl methylidene, cyclohexyl methylidene group, and their substituted analogues, for example a 4-methoxybenzylidene group, or a linear alkylene group such as an ethylene group (so as to form a propane-1,2-diol group), $R^5$ represents a hydrogen atom or a hydrocarbon group comprising one or more heteroatoms preferably selected from oxygen, sulfur or nitrogen, more preferably oxygen, provided that the compound of formula (1) is not:

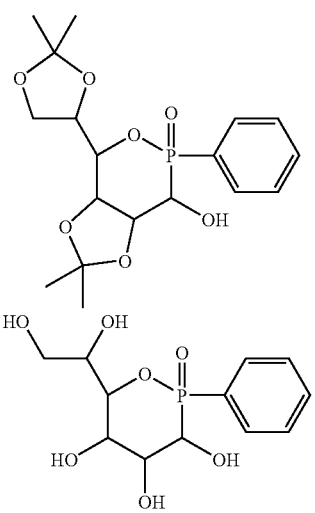

The present invention also provides anti-cancer pharmaceutical compositions for use in medical or veterinary medicine, which comprise at least one compound of formula (1).

The present invention further relates to a compound of formula (1) such as defined in the present description, for use as a drug.

The present invention also relates to the use of a compound of formula (1) for preparing a human or a veterinary pharmaceutical composition for treating and/or preventing cancer.

The present invention further relates to a therapeutic treatment method for a human or an animal, for preventing or treating the development of a cancer, said method comprising a step during which a therapeutically effective amount of a compound of formula (1) such as defined in the present description is administered to a human or an animal, either alone or in admixture with one or more pharmaceutically acceptable excipients and/or vehicles.

BRIEF DESCRIPTION OF THE DRAWINGS

FIG. 1 is a diagram showing the lack of cytotoxic effect of three compounds of the invention against non tumor cells. It shows the cell viability percentage as a function of the inventive compound (1) concentration, as expressed in μmol/L.

DETAILED DESCRIPTION OF THE INVENTION:

The present invention provides a new family of phosphinosugar compounds comprising a 6-membered ring including a phosphorus atom (phosphinane ring), in particular a new family of 1,2-oxaphosphinane 2-oxide.

Moreover, it has been demonstrated that a small dose of the new phosphinosugar family according to the invention was cytotoxic in vitro against cells collected from rat cerebral tumors (some compounds having $IC_{50}$ of less than 1 μM), and that they could hence be used as active ingredients for treating or preventing cancer.

It has also been proved that the new phosphinosugars of the invention were not cytotoxic in vitro against healthy cells at the doses where they do possess an anti-cancer activity.

In the present description of chemical compounds, the names are typically employed according to their usual definition.

As used herein, "alkyl" means a linear or branched, saturated or unsaturated hydrocarbon group, having from 1 to 25 carbon atoms, including in particular the acyclic groups with from 1 to 8 carbon atoms, such as methyl, ethyl, n-propyl, isopropyl, butyl, n-hexyl groups; cycloalkyl groups having preferably from 3 to 7 carbon atoms, cycloalkylmethyl groups having preferably from 4 to 8 carbon atoms.

As used herein, "substituted alkyl" means an alkyl group such as defined hereabove, that is bound through a $sp^3$ carbon atom and substituted with one or more aryl groups and/or comprising one or more heteroatoms such as N, S or O. Suitable examples include arylalkyl groups such as (—$CPh_3$)-trityl group, benzyl group noted Bn or 4-methoxybenzyl group, alkoxyalkyl groups, especially dialkoxymethyl groups such as diethoxymethyl or dimethoxymethyl groups, $CH_2CO_2R^{11}$ groups, wherein $R^{11}$ represents an optionally substituted alkyl group or an aryl group.

As used herein, "alkoxy" means an alkyl group that is bound to the rest of the molecule through an oxygen atom, for example an ethoxy, methoxy, or n-propoxy group.

As used herein, "aryloxy" means an aryl group bound to the rest of the molecule through an oxygen atom, for example a benzoxy group.

As used herein, "acyl" means a group derived from a carboxylic acid by removing the hydroxyl group, having preferably the formula —$C(O)R^8$, wherein $R^8$ represents an aryl or an optionally substituted alkyl group, for example an acetyl, propionyl, oleoyl, myristoyl or benzoyl group.

As used herein, "sulfonyl" means a group derived from a sulfonic acid by removing the hydroxyl group, having preferably the formula —$SO_2R^9$, wherein $R^9$ represents an optionally substituted alkyl group or an aryl group.

As used herein, "sulfinyl" means a radical derived from a sulfinic acid by removing the hydroxyl group, having preferably the formula —$SO_2R^{10}$, wherein R" represents an optionally substituted alkyl group or an aryl group.

As used herein, an "ester group" means a group of formula —$C(O)OR^{10'}$, wherein $R^{10'}$ represents an optionally substituted alkyl group or an aryl group.

As used herein, an "amide group" means a group of formula —$C(O)NR^{9'}R^{9''}$, wherein $R^{9'}$ represents an optionally substituted alkyl group or an aryl group and $R^{9''}$ represents an optionally substituted alkyl group, an aryl group or a hydrogen atom.

As used herein, a "thioamide group" means a group of formula —$C(S)NR^{9a}R^{9b}$, wherein $R^{9a}$ represents an optionally substituted alkyl group or an aryl group and $R^{9b}$ represents an optionally substituted alkyl group, an aryl group or a hydrogen atom.

As used herein, a "sulfonamide group" means a group of formula —$C(O)NR^{11'}R^{11''}$, wherein $R^{11'}$ represents an optionally substituted alkyl group or an aryl group and $R^{11''}$ represents an optionally substituted alkyl group, an aryl group or a hydrogen atom.

As used herein, "aryl" means an aromatic monovalent carbocyclic radical comprising only one ring (for example a phenyl group) or a plurality of fused rings (for example the naphthyl and terphenyl groups), which may optionally be substituted with one or more groups such as, without limitation, the alkyl (for example methyl), hydroxyalkyl, aminoalkyl, hydroxyl, thiol, amino, halogeno (fluoro, bromo, iodo, chloro), nitro, alkylthio, alkoxy (for example methoxy), aryloxy, mono-alkylamino, dialkylamino, acyl, carboxyl, alkoxycarbonyl, aryloxycarbonyl, hydroxysulfonyl, alkoxysulfonyl, aryloxysulfonyl, alkylsulfonyl, alkylsulfinyl, cyano, trifluoromethyl, tetrazolyl, carbamoyl, alkylcarbamoyl and dialkylcarbamoyl groups. Alternatively, two adjacent positions in the aromatic ring may be substituted with a methylenedioxy or ethylenedioxy group.

As used herein, "aryl" also includes the "heteroaryl" groups, that is to say the aromatic rings wherein one or more carbon atoms of the one or more aromatic rings are substituted with one heteroatom such as a nitrogen, oxygen, phosphorus or sulfur atom. The heteroaryl groups may be one or several aromatic rings-containing structures or structures with only one or several aromatic rings coupled to one or more non aromatic rings. In structures possessing many rings, the rings may be fused, covalently bound or bound to each other through a divalent common group such as a methylene, ethylene or a carbonyl group. Suitable examples of heteroaryl groups include the thiophene groups (2-thienyl, 3-thienyl), pyridine groups (2-pyridyl, 3-pyridyl, 4-pyridyl), isoxazole, phthalimide, pyrazole, indole and furan groups, as well as their benzofused analogues, phenyl pyridyl ketone, quinoline, phenothiazine, carbazole and benzopyranone.

As used herein, a "saccharyl group" includes all radicals derived by removing a hydroxyl group or a hydrogen atom (preferably a hydroxyl group), from a natural or synthetic, protected or unprotected carbohydrate or sugar. The saccharyl group does include the monosaccharyl and oligosaccharyl groups, such as disaccharyl groups. The saccharyl groups, for example glucosyl and mannosyl groups may be derived from sugars such as, without limitation, the glucuronic acid, the lactose, the sucrose, the maltose, the allose, the alltrose, the glucose, the mannose, the idose, the galactose, the talose, the ribose, the arabinose, the xylose, the lyxose, the fructose, the threose, the erythrose, the β-D-N-acetylgalactosamine, the β-D-N-acetylglucosamine, the fucose, the sialic acid, the N-acetylneuraminic acid, the N-acetylmuramic acid, the glucosamine, the galactosamine, the rhamnose and their protected or substituted analogues, that are substituted for example with acyl, alkyl, aryl, halogeno and amino groups, as well as their desoxy type analogues. As used herein, an oligosaccharyl group means a saccharyl group derived from at least two covalently bound monosaccharides, comprising preferably from 1 to 3 saccharide units. Preferred saccharyl groups are monosaccharyl groups. In compounds of formula (1), the saccharyl group is preferably bound through a X group representing O or NH, preferably O. For a description of saccharide type structures, see "Essentials of Glycobiology," Varki and al. Eds., Chapter 2 (Cold Spring Harbor Press, Cold Spring Harbor, N.Y., 1999).

As used herein, a "saccharide" means a monosaccharide or an oligosaccharide.

"Bn" stands for a benzyl group, "Ac" an acetyl group.

Some compounds of the invention may equally present in a solvated or a non solvated form, for example as an hydrate. Generally, solvated forms are equivalent to non solvated forms and are included within the frame of the invention. Some compounds of the invention may have a plurality of various crystalline or amorphous forms. Generally, all physical forms are equivalent for the uses that are intended according to the present invention and are included within the frame of the present invention.

The compounds of the invention have several asymmetric (optical) centers, so that enantiomers or diastereoisomers may exist. It is understood that the present invention does include all the enantiomers and diastereoisomers of the compounds of formula (1), as well as their mixtures, especially those based on racemates. The different isomers may be separated according to methods known to those skilled in the art, notably silica gel chromatography- or fractional crystallisation-based methods.

The preferred compounds of formula (1) are those wherein $Y=Z=O$, that is to say 1,2-oxaphosphinane 2-oxide compounds.

In the compounds of the invention, $R^1$ substituent, where it does not represent a hydrogen atom, is always bound to the intracyclic phosphorus atom through a carbon atom.

Preferred $R^1$ groups include H, alkyl groups, such as 2-benzyloxyethyl, ethyl, n-butyl, 3-phenylpropyl, n-octyl, dialkoxymethyl groups such as a diethoxymethyl or dimethoxymethyl group, aryl groups, such as phenyl, 4-methylphenyl, 4-nitrophenyl, 4-aminophenyl, 4-methoxyphenyl, 3,4-difluorophenyl, 2-thienyl, 4-fluorophenyl, 4-biphenyl, 3-methylphenyl, 3-methoxyphenyl and 3,5-difluorophenyl groups, as well as the following groups:

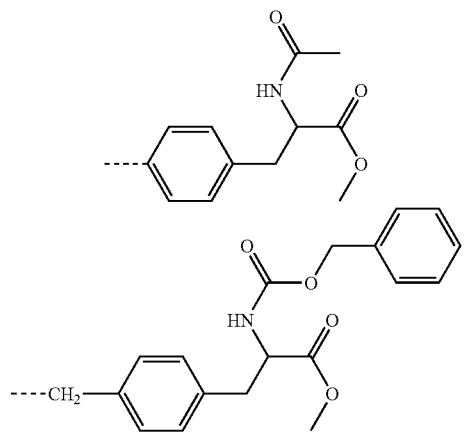

Preferred $R^2$ groups include H, arylsulfonyl, methylsulfonyl, trichloroacetimidate, benzyl, saccharyl and aryl groups, such as phenyl, 4-methylphenyl, 4-nitrophenyl, 4-aminophenyl, 3,4-difluorophenyl, 3,5-difluorophenyl, and 3,4-dinitrophenyl groups.

Preferred $X$—$R^2$ groups include O-aryl, OH, $NH_2$, NH-aryl, and S-aryl groups, and $NHCH_2CO_2R^{11}$, wherein $R^{11}$ is such as defined hereabove, $NHC(O)R^{12}$, wherein $R^{12}$ represents an aryl group or an optionally substituted alkyl group, O—$SO_2R^9$ wherein $R^9$ is such as defined hereabove, NH-Bn, O-saccharyl, $OC(=NH)CCl_3$, phosphonic acid, phosphinic acid or phosphine oxide, urea, thiourea, carbamate and carbonate groups.

Preferably, $R^3$ and $R^4$ represent independently from each other, a hydrogen atom, a benzyl, benzoyl or an acetyl group, or they form together a divalent radical of formula —$R^3$—$R^4$— representing preferably an isopropylidene group.

According to a preferred embodiment of the invention, $R^5$ is such that the compounds (1) have following formula:

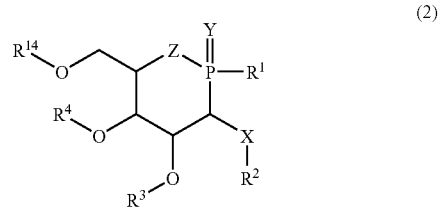

(2)

or following formula:

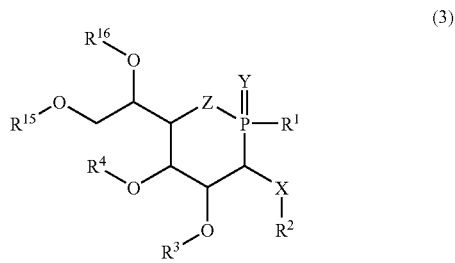

(3)

wherein $R^1$, $R^2$, $R^3$, $R^4$, X, Y and Z are as defined hereabove, $R^{14}$, $R^{15}$ and $R^{16}$ represent, independently from each other, a hydrogen atom, an aryl, an optionally substituted alkyl group, a trichloroacetimidate group, an acyl, formyl, sulfonyl, sulfinyl, tert-butyldiphenylsilyl group, an allyl, ester, amide, thioamide, sulfonamide group, or $R^{15}$ and $R^{16}$, taken together, form a divalent radical of formula —$R^{15}$—$R^{16}$—, wherein —$R^{15}$—$R^{16}$— preferably represents an isopropylidene, benzylidene, diphenyl methylidene, cyclohexyl methylidene group, and their substituted analogues, for example a 4-methoxybenzylidene group, or a linear alkylene group such as an ethylene group.

$R^5$ when not representing a hydrogen atom, does preferably have from 1 to 25 carbon atoms, preferably from 1 to 20 carbon atoms, more preferably from 1 to 10 carbon atoms, and even more preferably from 1 to 8 carbon atoms. $R^5$ may represent an optionally substituted alkyl group comprising one or more heteroatoms preferably selected from oxygen, sulfur or nitrogen, more preferably oxygen. Preferred $R^5$ groups include alkoxyalkyl groups such as benzyloxymethyl (—$CH_2OBn$), —$CH_2OH$, 2,2-dimethyl-[1,3]-dioxolan-4-yl and 1,2-dihydroxy-ethyl $CH(OH)CH_2OH$ groups, which means in the formulas (2) and (3) that $R^{14}$=H or Bn, and $R^{15}$=$R^{16}$=H or $R^{15}$ and $R^{16}$, taken together, do form an isopropylidene radical.

Compounds of formula (1) may be advantageously prepared by reacting an alkyl hydrogenophosphinate (5) with a sugar or a sugar analogue (4), providing a phosphinane (6), and optionally by post-functionalizing by means of a suitable reagent (e.g. by alkylation or arylation with an appropriate alkyl or aryl halide), essentially when $R^{18}$ such as defined hereafter is a hydrogen atom. Where $R^{18}$ represents a $R^2$ group, the compound of formula (6) is a compound of formula (1). The reaction scheme is shown hereunder:

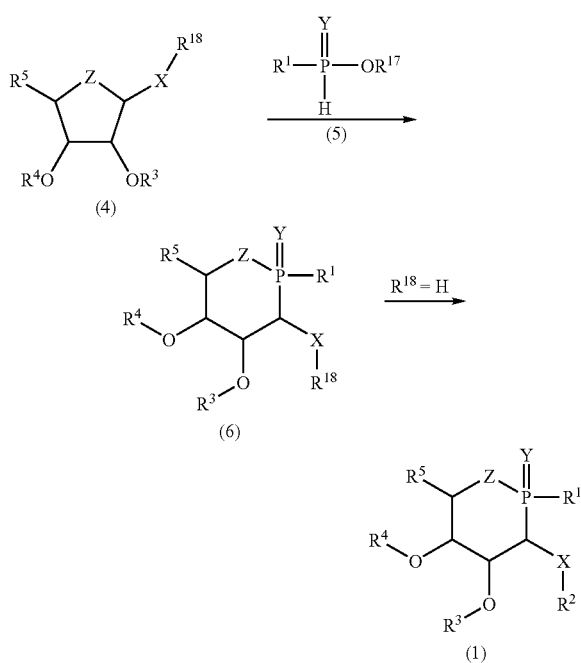

wherein $R^1$ to $R^5$, X, Y and Z are such as defined hereabove, $R^{17}$ represents an optionally substituted alkyl group or an aryl group, preferably an alkyl group and $R^{18}$ represents a hydrogen atom, an aryl group, an optionally substituted alkyl group, a trichloroacetimidate, acyl, formyl, sulfonyl, sulfinyl, tert-butyldiphenylsilyl, allyl, ester, amide, thioamide or sulfonamide group. Where X—$R^{18}$ is a X—H group, and especially a OH or $NH_2$ group, such group may undergo various reactions with electrophiles, amongst which some will be described below in detail, such as acylation, sulfonylation, alkylation or aromatic nucleophilic substitution reactions.

As used herein, the hydrogenophosphinate compounds will be simply referred to as H-phosphinates in the rest of the present description. Preferred H-phosphinates (5) are those wherein Y=O. Suitable examples of H-phosphinates (5) to be used in the present invention include alkylaryl-H-phosphinates ($R^1$=aryl, $R^{17}$=alkyl), for example methyl phenylhydrogenophosphinate and alkyl alkyl-H-phosphinates ($R^1$ and $R^{17}$ represent alkyl groups that can be the same or different), for example methyl ethylhydrogenophosphinate, methyl isopropylhydrogenophosphinate.

Amongst H-phosphinates (5), dialkoxymethyl-H-phosphinates of hereunder formula (7), wherein $R^{17'}$ represents an optionally substituted alkyl group, are another class of H-phosphinates that are particularly interesting in the context of the invention. $R^{17'}$ preferably represents a methyl or an ethyl group, more preferably an ethyl group, and Y preferably represents an oxygen atom.

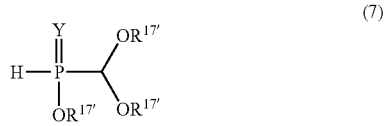

H-phosphinates (5) are reagents that are readily prepared by those skilled in the art, starting from commercially available precursors, for example by esterifying the corresponding phosphinic acid compound of formula (5), wherein $R^{17}$=H). As an example, we remind here the methyl phenylhydrogenophosphinate ($R^1$=Ph, Y=O, $R^{17}$=Me) synthesis, which can be prepared by esterifying phenylphosphinic acid with methyl chloroformate in the presence of pyridine, such as described in Afarinkia, K.; Yu, H. W. *Tetrahedron Lett.* 2003, 44. 781-783. Many alkyl H-phosphinates may be prepared according to the same method. Methyl phenylhydrogenophosphinate may also be prepared from dichlorophenylphosphine in methanol in the presence of pyridine, but the first synthetic route is more appropriate. Moreover, aryl-H-phosphinates ($R^1$=aryl) differently substituted on the aromatic ring may be obtained by pallado-catalyzed arylation of the corresponding hypophosphorous acid anilinium salt, according to the method described in Montchamp J. L., Dumond R. Y., *J. Am. Chem. Soc.,* 2001, 123, 510-511.

Alkyl alkylhydrogenophosphinates can also be prepared in two steps using trialkylphosphites, alkyl halides (generally an alkyl bromide) and magnesium as reagents, as detailed in the experimental part. For example, ethyl alkylhydrogenophosphinates can be generated from triethylphosphite and the corresponding alkyl halide. Alkyl arylhydrogenophosphinates can be prepared similarly, starting from the corresponding aryl halide, generally an aryl bromide or iodide (see e.g. Petnehazy I., Jaszay Z. M., Szabo, A., Everaert K., *Synthetic Commun.,* 2003, 33, 1665-1674).

Dialkoxymethyl-H-phosphinates (7) may be synthesized by reacting crystalline hypophosphorous acid ($H_2PO_2H$) with a trialkyl orthoformate according to the general reaction illustrated below, by using conditions similar to those described in Fitch S. J., *J. Am. Chem. Soc.,* 1964. 86, 61-64:

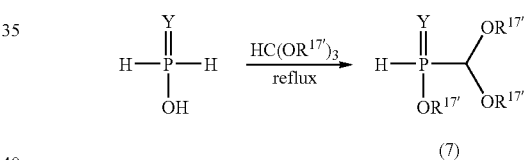

Preferably, triethyl orthoformate is used for such synthesis. The latter provides a more stable H-phosphinate as compared to the one obtained from trimethyl orthoformate. Preferred H-phosphinates (7) include ethyl diethoxymethyl hydrogenophosphinate and methyl dimethoxymethyl hydrogenophosphinate.

According to one embodiment of the invention, methyl phosphinate ($H_2PO_2Me$) is reacted with a compound (4) to produce a phosphinane (6) in which $R^1$=H and Y=O.

Sugars or sugar analogues (4) that can be used in the present invention preferably do not have any free hydroxyl group, except, possibly, the anomeric hydroxyl group, where present (then X=O). Hydroxyl groups may be protected by protecting groups that are the same or different. In particular, $R^3$, $R^4$, $R^{14}$, $R^{15}$ and $R^{16}$ groups are preferably protecting groups, that are the same or different.

As used herein, a protecting group is a group of atoms the aim of which consists in temporarily masking the site functionality to which it is linked in a molecule. Suitable examples of protecting groups may be found in Greene, T. W., Wuts, P. G. M. "Protective Groups in Organic Synthesis," $4^{eme}$ Ed. John Wiley & Sons, 2007.

The most interesting hydroxyl group protections in the context of the present invention include i) the acetate protection, using acetyl chloride, described inter alia in Zhdanov R. I., Zhenodarova S. M., *Synthesis,* 1975. 9. 222; Holfe G., Steglich W., Vorbruggen H., *Angew. Chem. Int. Ed. Engl.*, 1978, 17. 569; Stork G., Takahashi I., Kawamoto I., Suzuki T., *J. Am. Chem. Soc.*, 1978, 100, 8272, the deprotection being conducted in a basic non nucleophilic medium; ii) the benzoate protection, using benzoyl chloride or benzoyl anhydride, described inter alia in Schlessinger R. H., Lopes A., *J. Org. Chem.*, 1981, 46, 5252; Smith A. B., Hale K. J., *Tetrahedron Lett.*, 1989. 30, 1037. the deprotection being conducted in a basic non nucleophilic medium; iii) the benzyl protection, using benzyl halide in the presence of a base such as sodium hydride or potassium hydroxide, described inter alia in Czech B. P., Bartsch R. A., *J. Org. Chem.*, 1984. 49. 4076; Hartung C. H., Simonoff C., *Org. React.*, 1953, 7. 263, the deprotection being conducted by hydrogenolysis (see Heathcock C. H., Ratcliffe R., *J. Am. Chem., Soc.*, 1971, 93, 1746-1749 and Cook G. R., Beholz L. G., Stille J. R., *J. Org. Chem.*, 1994. 59. 3575-3581); iv) the benzylidene protection, using benzaldehyde in acidic medium, described especially in Wood H. B., Diehl H. W., Fletcher H. G. Jr, *J. Am. Chem. Soc.*, 1956. 78, 4715-4717; Fletcher H. G., *Methods Carbohydr. Chem.*, 1963, 2, 307; Carman R. M., Kibby J. J., *Aust. J. Chem.*, 1976, 29. 1761; McGowan D. A., Berchtold G. A., *J. Am. Chem. Soc.*, 1982, 104. 7036, the deprotection being conducted by hydrogenolysis or in acidic medium (see Hartung W. H., Simonoff R., Org. React., 1953, 7. 263-326); v) the isopropylidene protection, using acetone in the presence of a iodine catalytic amount, described inter alia in Kohn B. D., *Carbohydrate Research*, 1971, 18, 349-355 and Kim, C.; Hoang, R.; Theodorakis, E. A. Org. Lett. 1999. 1, 1295-1297, the deprotection being conducted by acid hydrolysis (see Angyal S. J., Beveridge R. J., *Carbohydr. Res.*, 1978, 65. 229; Ohgi T., Kondo T., Goto T., *Tetrahedron Lett.*, 1977. 4051; Lewbart M. L., Schneider J. J., *J. Org. Chem.*, 1969, 34, 3505).

According to a first embodiment of the invention, sugars (4) are hexoses or pentoses, all the hydroxyl groups of which being protected, except the anomeric hydroxyl group, which has to remain free so as to be able to produce an open reactive form during the ring-closure step. These sugars correspond to formula (8), wherein $R^3$ to $R^5$ are such as previously defined:

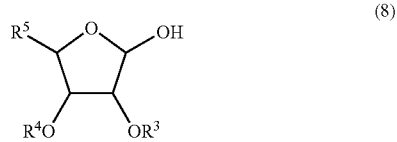

(8)

Suitable examples of hexose compounds to be used as starting materials (4) for producing a sugar (8) include, without limitation, L- or D-mannose (9), L- or D-glucose, L- or D-galactose.

D-mannose may be easily converted into 2,3:5,6-di-O-isopropylidene-α-D-mannofuranose (10) by acetalizing with acetone in the presence of iodine according to the method described in Kohn B. D., *Carbohydrate Research*, 1971, 18, 349-355 and C.; Hoang, R.; Theodorakis, E. A. Org. Lett. 1999. 1, 1295-1297. It is preferred to employ the isopropylidene protection used as compared to a benzylidene protection, as this latter produces a mixture of four di-O-benzylidene mannofuranose diastereomers.

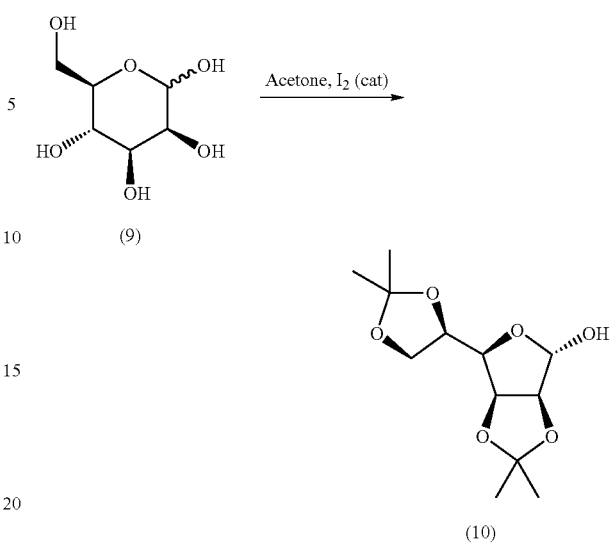

Suitable examples of pentoses to be used as starting materials (4) for producing a sugar (8) include, without limitation, L- or D-arabinose, L- or D-ribose, L- or D-xylose and L- or D-lyxose.

The present invention will be described below in more detail using D-arabinose (11) and D-ribose, but should not be in any way considered as limited to phosphinosugars derived from these building blocks. D-arabinose may be converted in three steps into 2,3,5-tri-O-benzyl-D-arabinofuranose (12), first of all by methoxylating the anomeric position in methanol in the presence of a catalytic amount of sulfuric acid, then by benzylating the $C_2$, $C_3$ and $C_5$ positions in THF using benzyl chloride and potassium hydroxide, and finally by selectively deprotecting the anomeric position in hydrochloric acid or in a mixture of acetic acid and hydrochloric acid. Another (8) type sugar, the 2,3,5-tri-O-benzyl-D-ribofuranose, may be obtained by following the same reaction process. Moreover, the synthesis of another usable sugar of the (8) type, 2,3,5-tri-O-benzyl-L-xylose, has been described in three steps starting from the commercial sugar in Behr J. B., Erard A., Guillerm G., *Eur. J. Org. Chem.*, 2002, 1256-1262. The corresponding synthesis from D-xylose rather than from L-xylose is also known (Desvergnes S., Py S., Vallée Y., *J. Org. Chem.*, 2005. 70, 1459-1462). While the benzyl protection is preferably used in the present invention, other protections may be used, especially the protection through benzoyl moieties, already described in the literature in Behr J. B., Guillerm G., Gaultier-Lefebvre A., Ryder N. S., *Bioorg. Med. Chem.*, 2000, 13, 1483-1486.

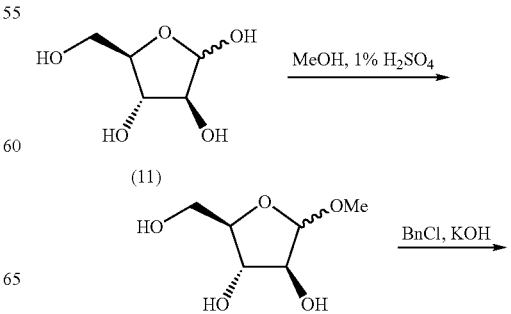

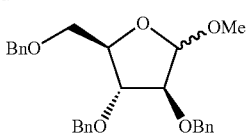

(12)

AcOH, HCl aq.

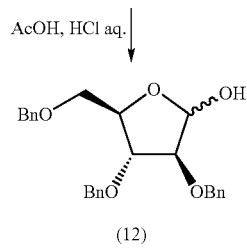

Another example of a sugar of the (8) type usable in the context of the present invention is the 2,3,5-tri-O-acetyl-D-ribofuranose (14), obtained in two steps from D-ribose (13), by first protecting the whole hydroxyl functionalities in the form of acetate, then by selectively deprotecting the anomeric position, especially by means of bis(tri-n-butyltin) oxide in dichloromethane. However, the benzyl protection is preferred as it provides the triprotected sugar with far better yields.

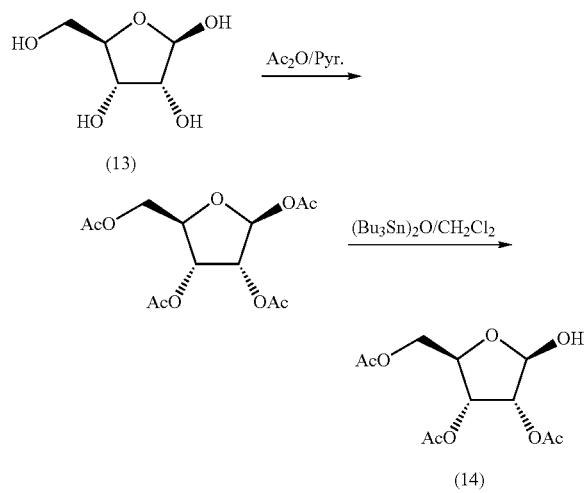

According to another alternative, a pentose such as D-ribose (13) may produce a sugar (8) type in two steps, namely the compound (15), the first step consisting in introducing the benzylidene moiety at the $C_2$-$C_3$ positions, which is conducted directly in benzaldehyde in the presence of acetic acid and zinc dichloride, and the second step consisting in introducing a trityl moiety onto the free primary alcohol position at the $C_5$ position.

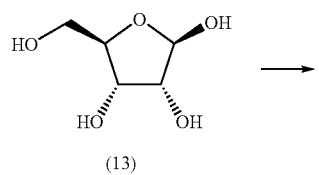

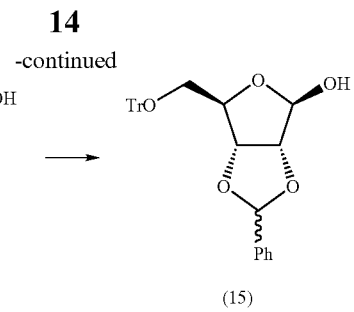

(15)

According to a second embodiment of the invention, as an alternative to the sugars (8) fully protected except their anomeric position, it is possible to use sugars (4) that have been modified at the anomeric position, wherein X does not represent oxygen, especially sugars (4), wherein X represents a sulfur atom or a nitrogen containing group NH or $NR^7$, $R^7$ being as previously defined. Modified sugars (16) may be obtained from protected sugars (8) having a free anomeric position according to the following reaction scheme:

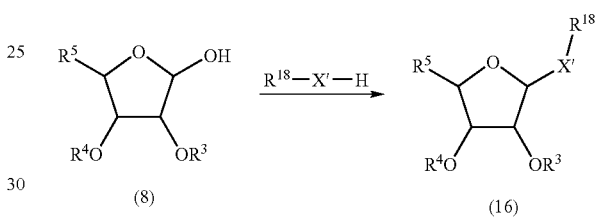

wherein $R^3$ to $R^5$ and $R^{18}$ are such as previously defined, and X' represents a sulfur or a selenium atom, a NH or $NR^7$ group, wherein $R^7$ is an optionally substituted alkyl group or an aryl group. Preferred modified sugars (16) are those wherein X'=NH, but the present invention should not be considered as being limited to this embodiment.

Sugars containing nitrogen at the anomeric position have been extensively described in the literature, in particular in Yamakazi, H. Y., Takabe, K., *Tet. Asymm.*, 1996, 2, 373-374; Yoda, H., Katoh, H., Takabe, K., *Tet. Lett.*, 2000, 40, 7661-7665; Noe, C. R., Knollmueller, M., Steinbauer, G., Jangg, E., Vollenkle, H., *Chem. Ber.*, 1988, 7, 1231-1239.

Sugars having the hereunder formula (17), wherein $R^3$ to $R^5$ and $R^{18}$ are such as previously defined, $R^{19}$ representing a hydrogen atom, an aryl group or an optionally substituted alkyl group, with the proviso that at least one of $R^{18}$ and $R^{19}$ groups represents a hydrogen atom, may be obtained by reacting a sugar having a free hydroxyl group at the anomeric position with a primary amine, under conditions that are well known to those skilled in the art, described in particular in Kleeman H. W., Heitsch H., Weck R., Wiegand F., *J. Med. Chem.*, 1992, 35, 559-567. Such amine may be aliphatic or aromatic in nature. Suitable examples of amines to be used herein include, without limitation, the following amines: aniline, benzyl amine, toluidine such as p-toluidine, ethyl amine, n-propyl amine, sec-propyl amine, n-butyl amine, sec-butyl amine, isobutyl amine, tert-butyl amine, n-pentyl amine, n-hexyl amine, n-heptyl amine, n-octyl amine, n-decyl amine, n-lauryl amine, myristyl amine, 1,2-dimethylhexyl amine, 3-pentyl amine, 2-ethylhexyl amine, allyl amine, 3-ethoxypropyl amine, 3-propoxypropyl amine, 3-isopropoxypropyl amine, 3-butoxypropyl amine, 3-isobutoxypropyl amine, 3-(2-ethylhexyloxy)propyl amine, aminocyclopentane, aminocyclohexane, aminonorbornene, phenethyl amine, alpha-methylphenethyl amine, naphthylamine, furfuryl amine.

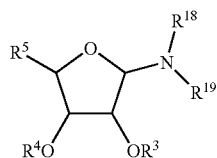

(17)

Examples of preferred families of compounds of formula (1) are those having the following formulae, in which $R^1$, $R^2$ and X are such as defined previously:

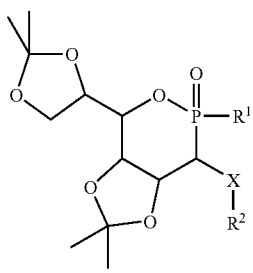

(1a)

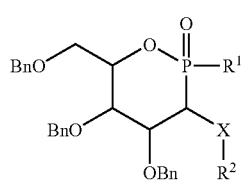

(1b)

The preparation of phosphinosugars (1) or (6) of the invention will be now described.

The condensation reaction of H-phosphinates (5) with protected sugars (4) may be conducted at room temperature in the presence of a basic catalyst. A first preferred class of compounds (1) of the invention corresponds to the 1,2-oxaphosphinanes of general formula (18) prepared such as illustrated in the following scheme:

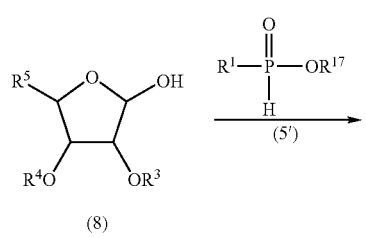

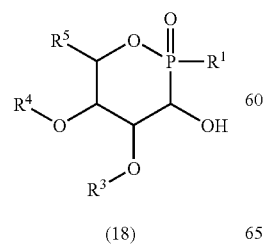

(18)

wherein $R^1$, $R^3$ to $R^5$ and $R^{17}$ are such as previously defined. Their synthesis does imply an addition, in the presence of tBuOK as basic catalyst, of H-phosphinate (5') on sugar (8), followed by a cyclization through intramolecular transesterification. The diastereoisomers formed may be separated according to usual methods, and their stereochemistry may be experimentally determined by means of X-ray diffraction conducted on monocrystals of these compounds or $^1$H NMR. Protecting the sugar (8) hydroxyl groups, except at the anomeric position, by groups that are non sensitive to the basic conditions used during the intramolecular transesterification, for example isopropylidene or benzyl groups, is particularly recommended. A basic catalyst amount corresponding to at least 0.2 base equivalent is preferably used, so as to obtain a complete conversion into a cyclic phosphinosugar.

Amongst the compounds (18), the compounds of formulae (19) and (20) are preferred, $R^1$ being as previously defined and preferably representing an aryl group, a hydrogen atom, an optionally substituted alkyl group such as a dialkoxymethyl group:

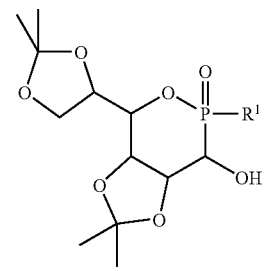

(19)

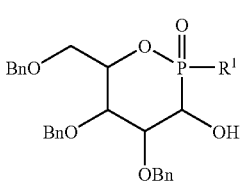

(20)

A second preferred class of compounds (1) of the invention corresponds to the 1,2-oxaphosphinanes of general formula (21) prepared such as illustrated in the following scheme:

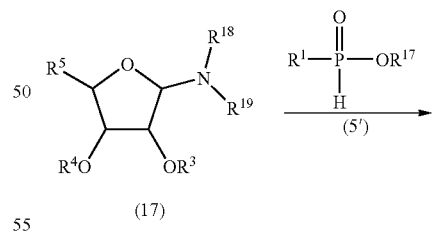

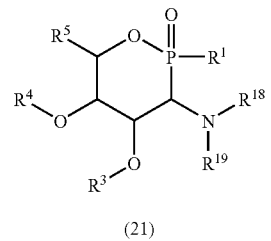

(21)

wherein $R^1$, $R^3$ to $R^5$ and $R^{17}$ to $R^{19}$ are such as previously defined, $R^{18}$ being preferably a hydrogen atom. The synthesis of these nitrogen containing phosphinosugars is conducted under the same conditions as their oxygenated analogues (18). A phosphinosugar (21') bearing an amino group at $C_3$ may be obtained from the nitrogen containing sugar (17) derived from benzylamine ($R^{18}$=H, $R^{19}$=Bn), by deprotecting on compound (21) the N-benzyl group by catalytic hydrogenation:

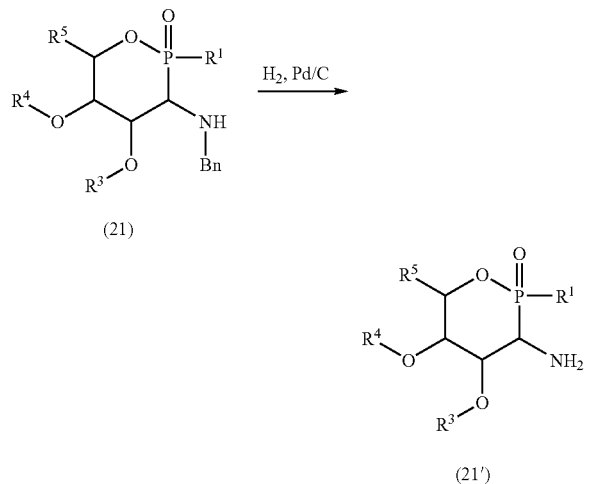

Amongst compounds (21), compounds of formulas (22) and (23) are preferred, $R^1$ and $R^{19}$ being as previously defined and $R^1$ representing preferably an aryl group, a hydrogen atom or a dialkoxymethyl group and $R^{19}$ representing preferably an aryl group:

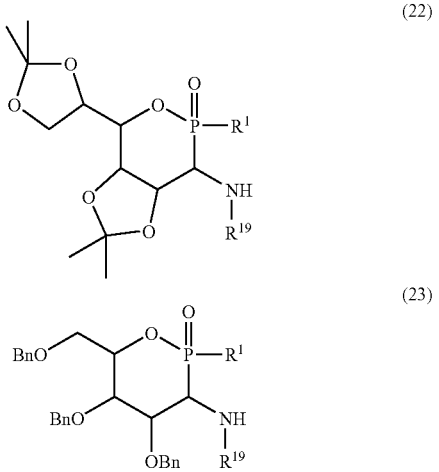

Some particular classes of compounds (1) that may be obtained by functionalizing X—$R^{18}$ in a compound of formula (6) will now be described.

According to one embodiment of the invention, the compounds (1), wherein $R^2$ represents an aryl group and X is an oxygen atom, may be obtained by modifying X—$R^{18}$ representing OH in a compound (6) by implementing an O-arylation reaction, especially by an aromatic nucleophilic substitution taking advantage of the nucleophilic nature of the concerned compound (6) alkoxide. The alkoxide may be formed by means of a base such as sodium hydride in a polar medium, preferably in DMF. As is well known to those skilled in the art, alkoxides may be arylated with various electrodeficient aromatic or heterocyclic halides, preferably fluorinated, chlorinated or brominated halides. The aromatic or heterocyclic reagents are preferably substituted with one or more electron-withdrawing groups such as nitro, cyano, fluoro or trifluoromethyl groups. Non limitative examples of particularly suitable halogenated reagents to be particularly used for such an aromatic nucleophilic substitution reaction are the 4-fluoronitrobenzene, 3,4-dinitrobromobenzene and 3,4-difluorobromobenzene. Substituents that are not compatible with the aromatic nucleophilic substitution reaction may be introduced later on the $R^2$ aryl group, either by modifying an already present substituent, or by directly introducing it, as is well known to those skilled in the art. The aromatic nitro moieties introduced may be easily converted later into amino moieties under usual conditions, especially by means of a pallado-catalyzed hydrogenation.

A third class of preferred compounds (1) corresponds to the following compounds of formula (24), wherein the various substituents are such as previously defined and $R^{20}$ represents a saccharyl group, preferably a monosaccharyl group.

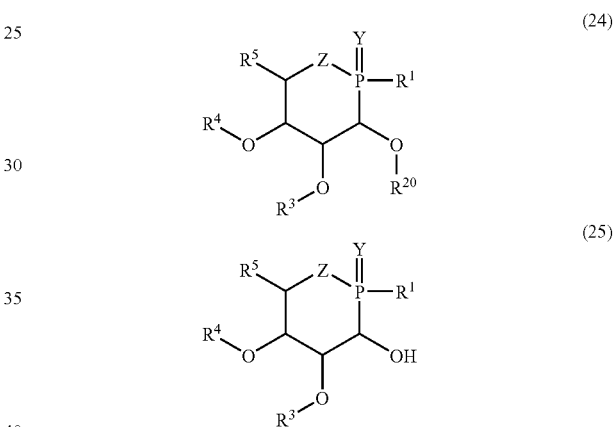

The compounds of formula (24) may be prepared by saccharide coupling from precursor compounds of formula (25), that do not present any anomeric position, according to methods that are well known to the one skilled in the art and described in particular in Tsukasa I., Takamura H., Watanabe K., Akari Y., Ishido Y., *Carbohydr. Res.*, 1986, 156. 241-246; Bravo-Altamirano K., Huang Z., Montchamp J. L., *Tetrahedron*, 2005. 61, 6315-6329; Montchamp J. L., Dumond Y. R., *J. Am. Chem. Soc.*, 2001, 123, 510-511; Varki A., *Glycobiology*, 1997. 3, 97; Lis H., Sharon N., *Eur. J. Biochem.*, 1993, 1, 218; Toshima K., Tatsuta K., *Chem. Rev.*, 1993, 93, 1503; Banoub J., Boulanger P., Lafont D., *Chem. Rev.*, 1992, 92, 1167. The glycoside coupling may be performed by using an activating moiety at the anomeric position, for example a fluorinated or a sulfur containing moiety such as described in Nicolaou, K. C., Seitz, S. P., Papahatjis, D. P., *J. Am. Chem. Soc.*, 1983, 105. 2430; Nicolaou K. C., Dolle R. E., Papahatjis D. P., Randall J. L., *J. Am. Chem. Soc.*, 1984, 106, 4189, a trichloroacetimidate moiety such as described in Schmidt R. R., *Angew. Chem.*, 1986, 98, 213 or by using n-pentenyl-type sugars, such as described in Fraser-Reid B., Udodong U. E., Wu Z., Ottosson H., Merritt J. R., Rao C. S., Roberts C., Madsen R., *Synlett*, 1992, 927.

In the context of the present invention, the compounds of formula (24) are preferably obtained by coupling a phosphinosugar of formula (25) with a saccharide (26) bearing a trichloroacetimide group at the anomeric position in the presence of a Lewis acid, for example boron trifluoride etherate, such as described in Stauch T., Dissertation, Universität Konstanz, 1995. The reaction proceeds while retaining the hydroxyl configuration of the phosphinosugar unit and provides a single enantiomer:

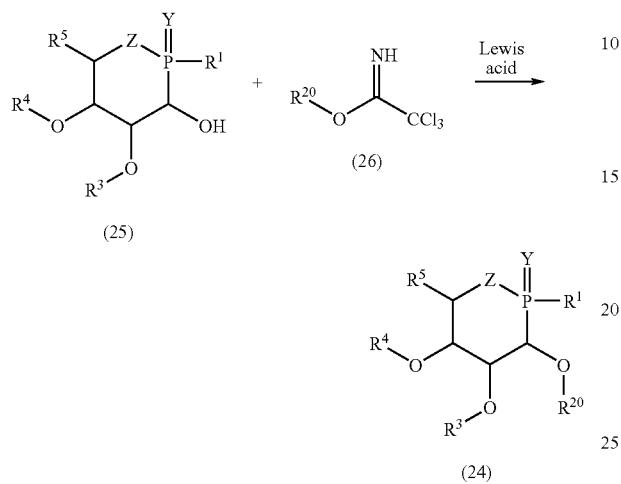

The activated saccharide (26) is traditionally obtained by reacting the corresponding saccharide with trichloroacetonitrile in the presence of a base compatible with the existing protecting groups, for example sodium hydride, as described in Schmidt R. R., Michel J., Roos M., *Liebigs Ann. Chem.*, 1984, 1343; Yamakazi F., Sato S., Nukada T., Ito Y., Ogawa T., *Carbohydr. Res.*, 1990, 31, 201; Grundler G., Schmidt R. R., *Liebigs Ann. Chem.*, 1984, 1826.

Amongst the compounds of formula (24), the preferred compounds are those obtained by coupling the phosphinosugar acceptor (25) with the trichloroacetimidate derivative of di-O-isopropylidene-D-mannofuranose (10), thus producing the following pseudo-disaccharides (27), the substituents being such as previously defined:

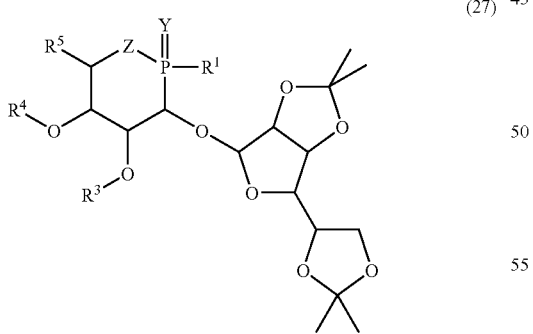

Another class of preferred compounds (1) corresponds to the following compounds of formula (24a), wherein the different substituents are such as previously defined. These compounds may be obtained by treating a compound of formula (25) with trichloroacetonitrile in the presence of a base compatible with the existing protecting groups, for example sodium hydride. Amongst these compounds, those of formulas (24b) and (24c) are preferred:

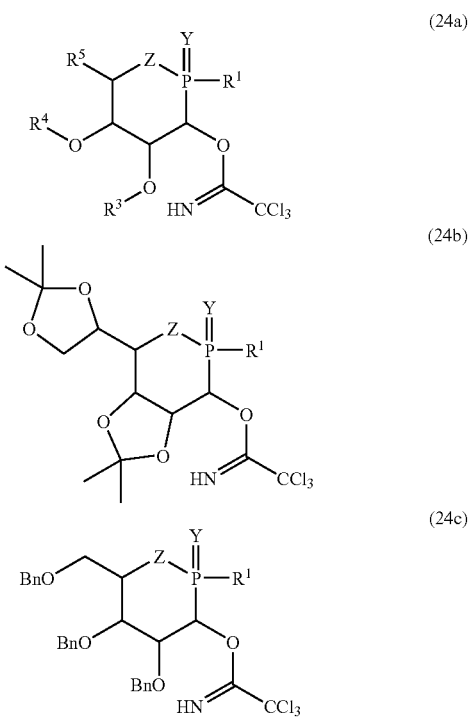

The compounds (1), wherein $R^1$ represents a hydrogen atom, noted compounds (28), may be prepared by acidic hydrolysis of the dialkoxymethyl group linked to the phosphorus atom of the precursor (29), especially by treatment with hydrochloric acid 1N at 40° C.:

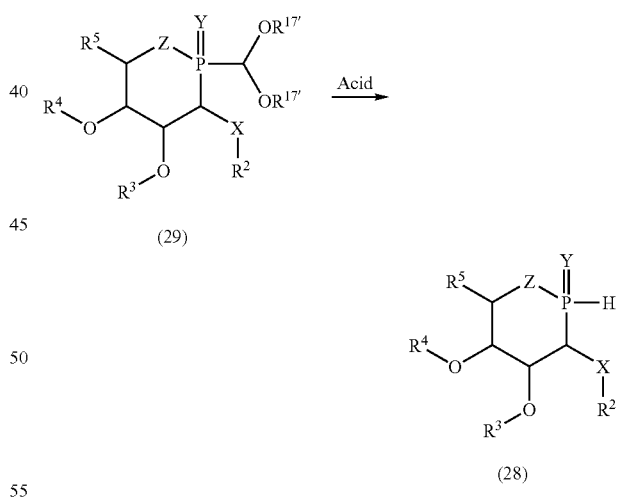

This synthesis route is preferred as compared to the direct condensation on a protected sugar of a P-unsubstituted alkyl H-phosphinate such as methyl phosphinate ($H_2PO_2Me$), because the phosphinane ring producing reaction proceeds in that case with a weak phosphinosugar (29) formation rate.

Protecting the compound (29) hydroxyl groups ($R^3$, $R^4$ and protecting groups included in the group $R^5$) with protecting moieties orthogonal to dialkoxymethyl groups rather than acid-labile isopropylidene groups makes it possible to prevent the deprotection of said hydroxyl groups during the acidic hydrolysis providing (28). In this embodiment, baselabile protecting groups or protecting groups that can be removed through hydrogenolysis are preferred, in particular the benzyl protection.

The presence of a P—H bond in the compounds (28) makes it possible to functionalize the phosphorus atom by means of various electrophiles, and thus to introduce $R^1$ moieties according to the invention. A suitable example is an arylation functionalization as described below or an alkylation functionalization (Michaelis Becker reaction in the presence of an alkyl halide and a base). Such synthetic route represents an alternative to the introduction of a $R^1$ moiety, such as an aryl or an alkyl group, by means of a H-phosphinate bearing said $R^1$ group.

In particular, the compounds (28) may undergo P-arylation reactions providing the compounds (30), wherein $R^{21}$ represents an aryl group. Said P-arylation reaction may be conducted by using aryl halides $R^{21}$—$X_1$ as reagents, wherein $X_1$ represents a bromine or iodine atom, and a palladium catalysis, preferably under the following conditions: palladium tetrakis triphenylphosphine (10 mol %), triethylamine (300 mol %), aryl halide (100 mol %) in toluene at 70° C. This reaction enables to introduce on the phosphorus atom aryl groups as varied as phenyl, 2,4-difluorophenyl, 4-methoxyphenyl, or 4-nitrophenyl groups, that is to say aryl groups that are either electrodeficient or electron-rich groups. The reaction proceeds even if the X—$R^2$ group is a OH group, and makes it possible to avoid using aryl-H-phosphinates (5) that are substituted in different ways.

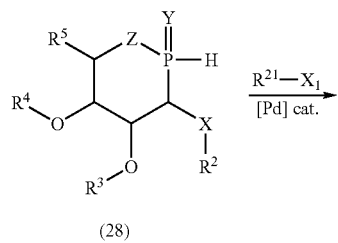

(28)

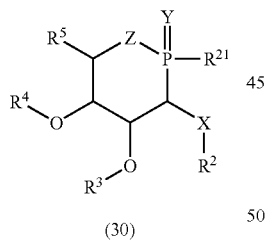

(30)

Although the phosphinosugars (1) of the invention may be obtained in a form in which all their hydroxyl groups are protected, the invention should not be in any way considered as limited to this embodiment and also includes the phosphinosugars (1) obtained in a form in which all their hydroxyl groups are deprotected, or only some of them. The preferred polyhydroxylated phosphinosugars corresponding to this other embodiment of the invention have formulae (31), (32), (33), (36) and (37), wherein $R^1$, $R^2$, Y and Z are such as previously defined, and $R^{22}$ represents an aryl group, for example a 4-tolyl group:

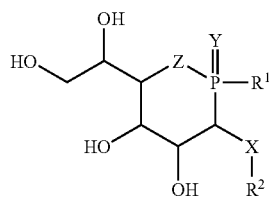

(31)

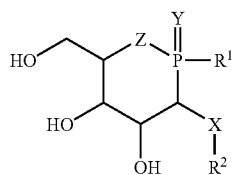

(32)

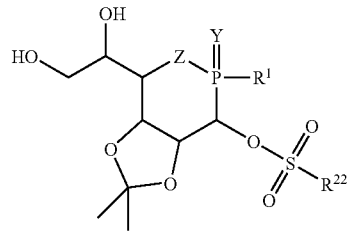

(33)

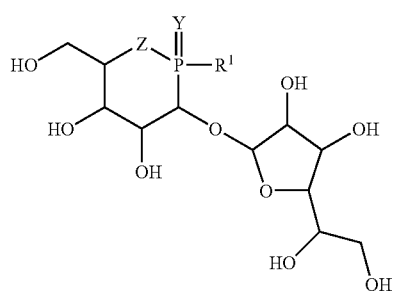

(36)

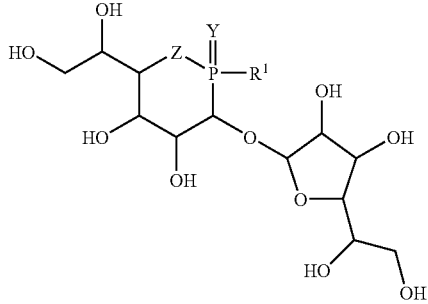

(37)

The compounds (31) and (33) may be obtained from precursors (34), either by deprotecting both isopropylidene groups using a hydrochloric acid treatment at 70° C. in the first case, or by selectively deprotecting only one of both isopropylidene groups using a sulfonic resin Amberlyst 15 as an acidic catalyst, in methanol at room temperature or at reflux under transacetalization conditions in the case of a compound (34), wherein X represents an oxygen atom and $R^2$ is an $SO_2R^{22}$ group such as defined hereabove. Without being bound by any theory, the present inventors believe that the presence of an arylsulfonyloxy group prevents the second isopropylidene group from being deprotected. Where $R^2$ represents a hydrogen atom, both isopropylidene groups of compound (34) are deprotected by a treatment with Amberlyst 15/methanol. Where $R^1$ represents a dialkoxymethyl group, the latter is simultaneously deprotected by a treatment with hydrochloric acid, thus providing a P—H bond. Moreover, the compound (31) was obtained by treating the compound (34) with hydrochloric acid even in the presence of a compound (34) in which X represents an oxygen atom and $R^2$ is a $SO_2R^{22}$ group such as defined hereabove.

C. rather than by a treatment with hydrochloric acid so as not to damage the glycosidic bond.

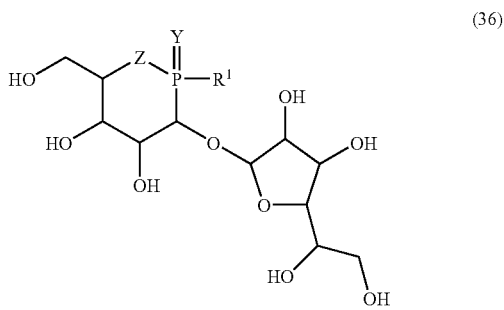

(36)

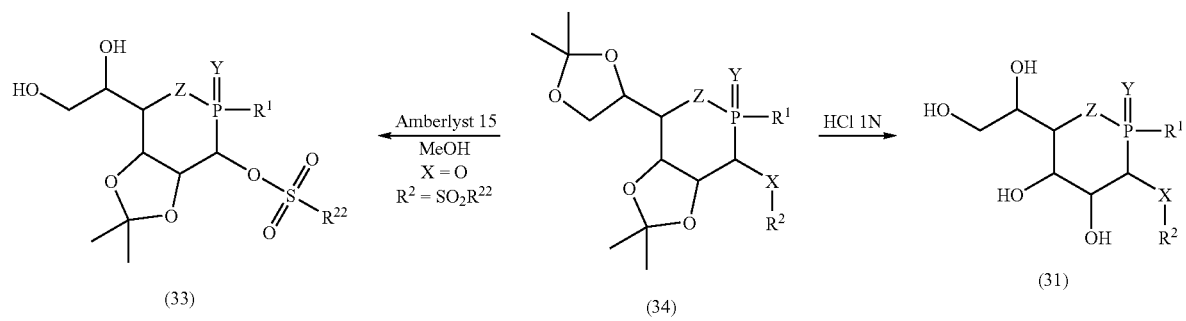

(33) (34) (31)

The compound (32) may be obtained from the benzylated precursor (35), by hydrogenolysis:

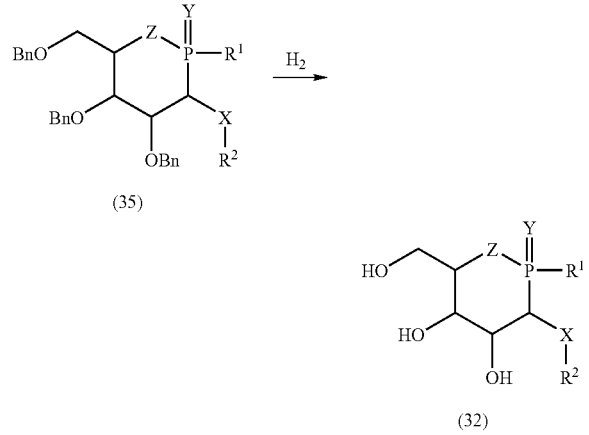

(35)

(32)

-continued

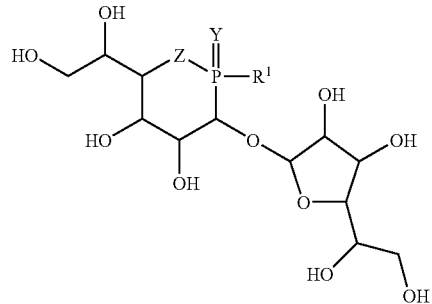

(37)

Several embodiments of the compounds of formula (1) of the invention, as well as their analytic data (NMR, mass spectrometry) are detailed in the examples.

Compositions Comprising a Compound of Formula (1) According to the Invention

As already mentioned in the present description, the compounds of formula (1) have an anti-cancer activity and thus represent active ingredients that can be used for any type of anticancer composition.

In particular, the compounds of formula (1) are useful as active ingredients in pharmaceutical compositions intended for a human or veterinary use, for treating cancers, that is to say cancerous cells, or for preventing cancers.

It is a further object of the invention to provide a pharmaceutical composition to be used in human or veterinary medicine, comprising at least one compound of formula (1) such as The various methods for deprotecting hydroxyl groups mentioned hereabove do not affect the cyclic phosphinic ester function.

The pseudo-disaccharide compounds of formula (36) and (37) may be obtained by deprotecting the aforementioned compounds of formula (27). Where an isopropylidene protection is used for some hydroxyl groups of the precursor compound and its group $R^2$ represents a saccharyl group, it is recommended to deprotect the existing isopropylidene groups using a treatment with Amberlyst 15/methanol at 55° defined in the present description, preferably in combination with one or more pharmaceutically acceptable excipients and/or vehicles.

The present invention further relates to a compound of formula (1) such as defined in the present description, for use as a drug in human or veterinary medicine.

The present invention further relates to a compound of formula (1) such as defined in the present description, for manufacturing an anticancer drug.

In the present application, cancerous cells represent cells having typical characteristics of cells developing a cancer, such as an uncontrolled cell proliferation, immortality, metastatic potential, rapid growth and very high proliferation rate, as well as some specific morphologic characteristics. Cancerous cells often come as a tumor, although such cells may exist alone in the body, or may be non oncogenic cancerous cells, such as leukemic cells. Cancerous cells may be associated to many cancer types, including without limitation, leukaemia, lymphoma, melanoma, neuroblastoma, liver cancer, cancer of the ovary, of the brain, of the lung, of the colon, of the breast, of the pancreas, of the prostate, of the testicles, of the oesophagus, of the uterus, of the uterine cervix, of the kidney, of the stomach, of the bladder, and cerebrospinal cancer or colorectal cancer. The pharmaceutical compositions of the invention may be used for the therapeutic treatment of at least one of the aforementioned cancers.

A human or veterinary pharmaceutical composition according to the invention may also comprise one or more other active ingredients, including one or more other anticancer compounds. As other active ingredients that may be included in a pharmaceutical composition according to the invention, there are in particular antihistaminic agents, anti-inflammatory agents, disinfectant agents or local anaesthetic agents.

A pharmaceutical composition comprising an anticancer compound of the invention presents equally in either a solid or a liquid form. In a liquid form, the pharmaceutical composition preferably comes as an aqueous suspension or as a non aqueous suspension, or as a water-in-oil or a oil-in-water emulsion.

Amongst the pharmaceutical compositions of the invention, those compositions can be particularly mentioned, that are suitable for the oral, topical, parenteral, nasal, intravenous, percutaneous, transcutaneous, rectal, perlingual or airway administration, and especially simple or sugar coated tablets, sublingual tablets, capsules, lozenges, suppositories, creams, ointments, dermic gels, and oral intake or injection ampoules.

The dosage regimen varies depending on the sex, the age and the weight of the patient, depending on the administration route, and on the cancer type, the evolution state of the cancer, in particular on whether metastases have been detected in the patient or not. The dosage regimen may also vary depending on the type of associated anticancer treatment(s).

Generally speaking, a compound of formula (1) such as defined in the present description is used in amounts preferably ranging from 0.001 mg/kg of patient or animal body weight, to 1 g/kg of patient or animal body weight per 24 hours, in one or several drug intakes. Preferably, said amount is at least equal to 0.01 mg/kg, more preferably 0.05 mg/kg. Preferably, said amount is at most equal to 500 mg/kg, more preferably to 100 mg/kg.

To be administered by the oral route, a pharmaceutical composition according to the invention may present in the form of tablets, capsules, coated tablets, syrups, suspensions, solutions, powders, pellets, emulsions, suspensions of microspheres or nanospheres, lipid vesicle suspensions or various polymer-based vesicles.

To be administered by the oral route, a pharmaceutical composition according to the invention may be in the form of tablets that may be obtained from solid compositions comprising at least one compound of formula (1) in combination with various excipients such as microcrystalline cellulose, sodium citrate, calcium carbonate, dicalcium phosphate or glycine. Various disintegrating agents such as starch (corn, potato or tapioca starch, etc.), alginic acid or a silicate may be used. Binders such as polyvinyl pyrrolidone, sucrose, gelatin, or acacia may also be used. Lubricants such as magnesium stearate, sodium laurylsulfate, or even talc may also be used. Such solid compositions, as a powder, may be used for preparing gelatin capsules. For solid compositions, lactose or polyethylene glycol with a high molecular weight may also be used.

In order to prepare liquid compositions for oral administration, the compound of formula (1) may be combined with various sweeteners, flavouring agents, colouring agents, possibly together with emulsifying agents or suspending agents, in combination with diluents such as water, ethanol, propylene glycol, glycerin or any combination of these excipients.

To be administered by the parenteral route, a pharmaceutical composition according to the invention may present in the form of infusion or injection solutions and suspensions.

To be administered by the parenteral route, oil or water solutions or suspensions, emulsions, or implants may be used, in particular, including suppositories. For example, a compound of formula (1) may be dispersed in a liquid vehicle such as a liquid saline solution or a saline solution containing 5% by weight of dextrose, that are traditionally used for preparing pharmaceutical formulations for injection.

To be administered by the enteral route, controlled release compositions may be used, for example compositions wherein the compound of formula (1) is protected from the external environment by a plurality of coating layers that decompose in a different way, for example upon contact with a neutral or basic medium (enteric coatings) or upon contact with an aqueous medium (coating layers comprising soluble polymers or polymers that decompose in water).

Generally speaking, a pharmaceutical composition according to the invention comprises from 0.01% to 99% by weight, and advantageously from 1% to 90% by weight, of an anticancer compound, as compared to the total weight of the composition.

Generally speaking, a pharmaceutical composition according to the invention comprises from 1% to 99.99% by weight, and advantageously from 10% to 99% by weight of an excipient or a mixture of pharmaceutically acceptable excipients.

The pharmaceutical composition of the present invention may be used for a parenteral, topical or local administration, and in a prophylactic and/or therapeutic way. Thus, the anticancer compound according to the invention is prepared in a form that is adapted to the selected administration route, for example in a liquid or a freeze-dried form. The pharmaceutical compositions comprising an anticancer compound of the invention may contain an excipient and/or a liquid or solid, pharmaceutically acceptable vehicle, for example an aqueous vehicle. Many pharmaceutically acceptable excipients and/or vehicles may be used, for example, water, where appropriate in admixture with propylene glycol or polyethylene glycol, buffered water, a saline solution, a glycine solution and their derivatives as well as agents that are required to produce the physiologic conditions, as for example buffering agents and pH regulating agents, surfactants such as sodium acetate, sodium lactate, sodium chloride, potassium chloride, calcium chloride, this list being non limitative. In addition, the pharmaceutical composition may be sterilized using sterilization methods that are well known to those skilled in the art.

Suitable inert, non toxic, pharmaceutically acceptable vehicles, adjuvants or excipients include as non limitative examples, diluents, solvents/solubilizing agents, preservatives, wetting agents, emulsifying agents, dispersing agents, binders, swelling agents, disintegrating agents, capsulating agents, retardants, lubricants, absorbents, suspending agents, colouring agents, flavours, stabilizers, thickeners, etc. Such compounds are for example magnesium carbonate, magnesium stearate, talc, lactose, pectin, dextrin, starch, gelatin, cellulose-based materials, cacao butter, etc.

When preparing a solid composition in the form of tablets, the main active ingredient is mixed with a pharmaceutical vehicle such as gelatin, starch, lactose, magnesium stearate, talc, gum arabic or equivalents.

Tablets may be coated with sucrose or any other suitable starting material or they otherwise can be treated in such a way that they have a long-acting or a delayed activity and they release in a sustained manner a predetermined amount of active ingredient.

A capsule preparation is obtained by mixing the active ingredient with a diluent and by pouring the thus obtained mixture in soft or hard capsules.

A pharmaceutical composition in the form of a syrup or elixir may contain the active ingredient together with a sweetener, preferably a hypocaloric sweetener, methylparaben and propylparaben as antiseptic agents, as well as a flavouring agent and a suitable colouring agent.

Water dispersible powders or granules may contain the active ingredient in admixture with dispersing agents or wetting agents or suspending agents, such as polyvinyl pyrrolidone, as well as sweeteners or taste modifiers.

The active ingredient may also be formulated in microcapsules, optionally with one or more supports or additives.

Generally speaking, for providing a pharmaceutical composition according to the present invention, those skilled in the art can advantageously refer to the most recent edition of the European Pharmacopoeia, for example to the 5th European Pharmacopoeia edition published in January 2005, or to the 6th European Pharmacopoeia edition, made publicly available in June 2007.

Methods for preparing pharmaceutical compositions according to the invention may be easily found by those skilled in the art, for example in Remington's Pharmaceutical Sciences, Mid. Publishing Co, Easton, Pa., USA.

Physiologically acceptable adjuvants, vehicles and excipients are also described in "Handbook of Pharmaceutical Excipients," Second Ed., American Pharmaceutical Association, 1994.

For formulating a pharmaceutical composition according to the invention, the man skilled in the art may advantageously refer to the most recent edition of the European Pharmacopoeia or the United States Pharmacopoeia (USP).

Those skilled in the art may especially advantageously refer to the USP 30-NF 25 edition of the United States Pharmacopoeia (USP).

Advantageously, a pharmaceutical composition such as defined hereabove can suitably be administered by the oral, parenteral or intravenous route.

When the pharmaceutical composition according to the invention comprises at least one pharmaceutically or physiologically acceptable excipient, it is in particular an excipient that is suitable for an oral administration of the composition or an excipient suitable for a parenteral administration of the composition.

The present invention also relates to a therapeutic treatment method for a human or an animal, in particular a non human mammal, for preventing or treating the development of a cancer, said method comprising a step during which a therapeutically effective amount of a compound of formula (1) such as defined in the present description or of a pharmaceutical composition containing said compound of formula (1), is administered to the human or to the animal.

The invention may be applied in combination with other therapeutic modalities, such as chemotherapy, cryotherapy, hyperthermia, radiotherapy, etc.

The present invention will now be illustrated with following non limitative examples.

EXAMPLES

A) Synthesis Procedures for the Compounds of the Invention a) Material

Unless otherwise specified, NMR spectra were recorded on a BRUKER AVANCE 400 spectrometer working at 400.13 MHz ($^1$H) in $CDCl_3$. Chemical shifts are expressed in ppm/TMS for $^1$H and $^{13}$C; the coupling constants $^nJ$ are expressed in Hz. When the spectra are spectra of first order or can be considered as such, the signals are referred to with letters s (singlet), d (doublet), t (triplet), q (quadruplet), m (multiplet) and with combinations of these letters. A broad signal will be identified with one of these letters, followed with letter l.

The high resolution mass spectra (HRMS) were measured in a JEOL JMS DX-300 apparatus in FAB (fast atom bombardment) positive ionization mode with a p-nitrobenzyl alcohol (NBA) matrix.

The moisture sensible or oxygen sensible compounds were manipulated under nitrogen using Schlenk methods. Anhydrous solvents were distillated under nitrogen with the suitable dessicant.

Flash chromatography separation of the products was conducted on a Merck silica gel column of 15-40 µm or 30-75 µm.

b) Production of Compound of Formula (1) Precursors

Methyl phenyl hydrogenophosphinate preparation

In a three-necked flask under nitrogen were introduced 30 g of phenylphosphinic acid (0.211 mol), 440 ml of dichloromethane and 16.3 ml of methyl chloroformate (0.211 mol, 1 eq.). 17.2 ml of pyridine (0.211 mol, 1 eq.) were slowly added under vigourous stirring. Once the effervescence stopped, it was refluxed for 40 mn and then was allowed to come back to room temperature.

The reaction medium was poured in 160 ml of hydrochloric acid 0.1 N. The organic phase was separated, washed with water and dried on sodium sulfate. After solvent evaporation, crude methyl phenyl hydrogenophosphinate was collected (yellow oil). Distillation under reduced pressure (0.1 mmHg) and under nitrogen.

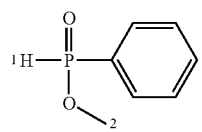

3.1

M (g/mol)=156.12
C₇H₉O₂P (N° CAS 7162-15-4)
Colourless oil (21.31 g, 13.6 mol)
1 diastereomer
Yield=64%
¹H NMR (400.13 MHz, CDCl₃): δ 3.75 (d, 3H, ³$J_{P-H}$=12.0 Hz, ²CH₃), 7.51 (d, 1H, ¹$J_{P-H}$=565.7 Hz, P—H), 7.61-7.74 (m, 5H, $CH_{Ar}$)

Methyl(dimethoxymethyl)phenylphosphinate preparation

In a previously deoxygenated three-necked flask were introduced under nitrogen 2 g of phenylphosphinic acid (0.011 mol), 17 ml of methyl orthoformate (0.092 mol, 8 eq.). 400 mg of p-toluenesulfonic acid (0.002 mol, 0.2 eq.) were then added. The medium was then refluxed for 48 hours.

The reaction medium was then filtered, the filtration product was evaporated under reduced pressure using a vane pump, to give an oily residue. This residue was taken up in diethyl ether resulting in a white precipitate (phenylphosphinic acid) that was filtered, then the filtration product was evaporated to give the expected pure compound as a colourless oil.

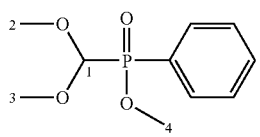

3.11

M (g/mol)=230.20
C₁₀H₁₅O₄P
Colourless oil (2,3 g)
1 diastereomer
Yield=69%
¹H NMR (400.13 MHz, CDCl₃): δ 3.37 (s, 3H, ²CH₃), 3.38 (s, 3H, ³CH₃), 3.65 (d, 3H, ³$J_{P-H}$=10.5 Hz, ⁴CH₃), 4.54 (d, 1H, ²$J_{P-H}$=7.9 Hz, ¹CH), 7.29-7.48 (m, 3H, $CH_{Ar}$), 7.68-7.78 (m, 2H, $CH_{Ar}$).

Deprotection of methyl(dimethoxymethyl)phenylphosphinate

In a Schott tube were introduced 1 g of methyl (dimethoxymethyl)phenylphosphinate (0.011 mol), and 10 ml of hydrochloric acid 1N. The medium was then heated at 70° C. for 1 hour.

The reaction medium was then evaporated under reduced pressure to give the methyl phenylhydrogenophosphinate as a colourless oil.

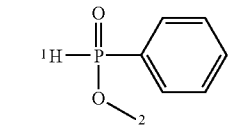

3.12

M (g/mol)=156.12
C₇H₉O₂P
Colourless oil
Yield=100%
¹H NMR (400.13 MHz, CDCl₃): δ 3.75 (d, 3H, ³$J_{P-H}$=12.0 Hz, ²CH₃), 7.51 (d, 1H, ¹$J_{P-H}$=565.7 Hz, P—H), 7.61-7.74 (m, 5H, $CH_{Ar}$)

Preparation of crystalline hypophosphorous acid

A 50% hypophosphorous acid aqueous solution was concentrated on a rotary evaporator under the vacuum of the vane pump (0.3 mmHg). The water bath was heated to a temperature of less than 50° C. When the acid became sirupy, it was allowed to cool to room temperature, then a piece of the single neck flask was dipped into cold alcohol (−40° C.), the crystal nucleation was spontaneous and developed within the whole flask. The anhydrous hypophosphorous acid is a very hygroscopic, white solid at room temperature, that will hence be stored under nitrogen in a refrigerator. After each use, it was then arranged under vane pump vacuum with phosphorous pentoxide in an intermediate schlenk tube, then isolated under nitrogen and placed in a refrigerator again.

Preparation of methyl(dimethoxymethyl)phenylphosphinate

In a previously deoxygenated three-necked flask were introduced under nitrogen 11 g of hypohosphorous acid (0.165 mol), 45 ml of methyl orthoformate (0.31 mol, 2.1 eq.) and then 6 g of p-toluenesulfonic acid (0.032 mol, 0.2 eq.). The medium was then refluxed for 48 hours.

The reaction medium was then evaporated under reduced pressure. The thus obtained oily residue was taken up in 150 ml of chloroform and washed with a sodium hydrogenocarbonate saturated solution. After drying, the organic phase was concentrated, the thus obtained oil was then distilled under reduced pressure (0.03 mmHg, 90° C.)

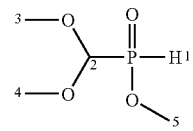

3.14

M (g/mol)=154.12
C₄H₁₁O₄P
Colourless oil (15.4 g)
Yield=64%
¹H RMN (400.13 MHz, CDCl₃): δ 3.37 (s, 3H, ³CH₃), 3.40 (s, 3H, ⁴CH₃), 3.75 (d, 3H, ³$J_{P,H}$=10.6 Hz, ⁵CH₃), 4.46 (d, 1H, ²$J_{P-H}$=12.1 Hz, ²CH), 6.83 (d, 1H, ¹$J_{P-H}$=557.0 Hz, P—¹H).

Preparation of ethyl(diethoxymethyl)phosphinate

In a previously deoxygenated three-necked flask were introduced under nitrogen 14.2 g of hypophosphorous acid (0.215 mol), 80 ml of methyl oformate (0.48 mol, 2.2 eq.) and 7.4 g of p-toluene-sulfonic acid (0.043 mol, 0.2 eq.). The medium was then refluxed for 24 hours.

The reaction medium in a first step was taken up in 200 ml of chloroform and washed with a sodium hydrogenocarbonate saturated solution. After drying The organic phase was evaporated using the vane pump, the resulting oil was then distilled under reduced pressure (0.02 mmHg, 100° C.)

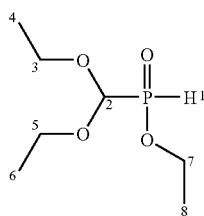

3.16

M (g/mol)=196.18
$C_7H_{17}O_4P$
Colourless oil (37.9 g)
Yield=61%
$^1$H NMR (400.13 MHz, CDCl$_3$): δ 1.20 (t, 3H, $^3J_{H-H}$=3.4 Hz, $^4CH_3$), 1.22 (t, 3H, $^3J_{H-H}$=3.4 Hz, $^6CH_3$), 1.34 (t, 3H, $^3J_{H-H}$=3.6 Hz, $^8CH_3$), 3.62-3.82 (m, 4H, $^3CH_2+^5CH_2$), 4.07-4.28 (m, 2H, $^7CH_2$), 4.67 (d, 1H, $^2J_{P-H}$=23.1 Hz, $^2CH$), 6.91 (d, 1H, $^1J_{P-H}$=560.0 Hz, $^1$P—H).

Preparation of ethyl alkylhydrogenophosphinates and ethyl arylhydrogenophosphinates In a three-necked flask, with a cooler and a dropping funnel that had been previously deoxygenated and under nitrogen atmosphere were introduced 3.6 g of magnesium (0.1 mol), and 70 ml of anhydrous tetrahydrofuran. Alkyl or aryl halide (0.15 mol) was slowly added. The medium was stirred at 50° C. for 2 hours. The reaction developpement was monitored by NMR $^{31}$P. The medium was cooled to room temperature, and added dropwise on a second three-necked flask deoxygenated and under nitrogen atmosphere, containing 17.4 ml of triethylphosphite freshly distilled (0.1 mol) and 20 ml of anhydrous tetrahydrofuran. The medium was refluxed for 3 hours, then cooled at room temperature to hydrolyse the phosphonite with an hydrochloric acid solution 6N, until pH 2.

The medium was then evaporated under reduced pressure. The oily residue was diluted in 150 ml of chloroform and washed with water. After drying on magnesium sulfate, the organic layer was evaporated and the oily residue was distilled under reduce pressure.

Ethyl ethylhydrogenophosphinate (3.17)

This compound was obtained using 11.2 ml of ethyl bromide (0.15 mol).

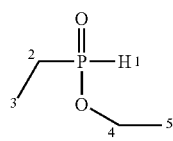

M (g/mol)=122.10
$C_4H_{11}O_2P$
Colorless oil
Yield=21%
$^{31}$P RMN (161.97 MHz, CDCl$_3$): δ 33.8
$^1$H RMN (400.13 MHz, CDCl$_3$): δ 1.08 (qd, 3H, $^3CH_3$), 1.29 (q, 3H, $^5CH_3$), 1.71 (qd, 2H, $^2CH_2$), 4.07 (m, 2H, $^4CH_2$), 6.95 (d, 1H, $^1J_{P-H}$=525.8 Hz, P—$^1$H).

Ethyl n-butylhydrogenophosphinate (3.34)

This compound was obtained using 16.2 ml of n-butyl bromide (0.15 mol).

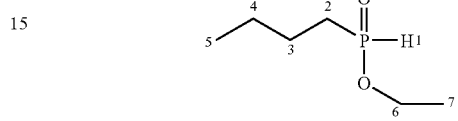

M (g/mol)=150.16
$C_6H_{15}O_2P$
Colorless oil
Yield=18%
$^{31}$P RMN (161.97 MHz, CDCl$_3$): δ 39.2
$^1$H RMN (400.13 MHz, CDCl$_3$): δ 0.86 (t, 3H, $^5CH_3$), 1.27 (t, 3H, $^7CH_3$), 1.31-1.74 (m, 6H, $^2CH_2+^3CH_2+^4CH_2$), 3.95-4.01 (m, 2H, $^6CH_2$), 7.02 (d, 1H, $^1J_{P-H}$=526.0 Hz, P—$^1$H).

Ethyl n-octylhydrogenophosphinate (3.13)

This compound was obtained using 26 ml of n-octyl bromide (0.15 mol).

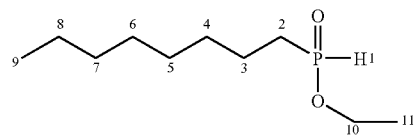

M (g/mol)=206.27
$C_{10}H_{23}O_2P$
Colorless oil
Yield=22%
$^{31}$P RMN (161.97 MHz, CDCl$_3$): δ 37.7

Ethyl phenylpropylhydrogenophosphinate (3.23)

This compound was obtained using 23 ml of 3-phenylpropyl bromide (0.15 mol).

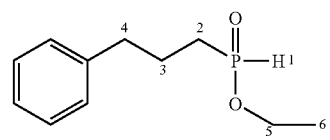

M (g/mol)=212.23
$C_{11}H_{17}O_2P$
Colorless oil
Yield=30%
$^{31}$P RMN (161.97 MHz, CDCl$_3$): δ 39.5

¹H RMN (400.13 MHz, CDCl₃): δ 1.25 (td, 3H, ⁷CH₃), 1.65-1.88 (m, 4H, ⁴CH₂+³CH₂), 2.62-2.71 (m, 2H, ²CH₂), 3.96-4.11 (m, 2H, ⁵CH₂), 6.98 (d, 1H, ¹$J_{P-H}$=527.8 Hz, P—¹H), 7.02-7.24 (m, 5H, $CH_{Ar}$).

Ethyl 2-thienylhydrogenophosphinate (3.15)

Obtained from 2-thienyl bromide.

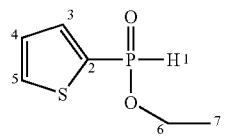

M (g/mol)=176.18
$C_6H_9O_2PS$
Colorless oil
Yield=18%
³¹P RMN (161.97 MHz, CDCl₃): δ 14.9
¹H RMN (400.13 MHz, CDCl₃): δ 1.01 (s, 3H, ⁷CH₃), 3.76-3.83 (m, 2H, ⁶CH₂), 3.75 (d, 3H, ³$J_{P-H}$=10.6 Hz, ⁵CH₃), 4.46 (d, 1H, ²$J_{P-H}$=12.1 Hz, ²CH), 6.77-7.32 (m, 3H, $CH_{Ar}$), 7.31 (d, 1H, ¹$J_{P-H}$=592.8 Hz, P—¹H).

Ethyl phenylhydrogenophosphinate (3.4)

Obtained from phenyl iodide.

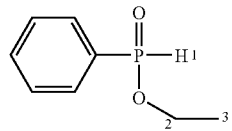

M (g/mol)=170.15
$C_8H_{11}O_2P$
Colorless oil
Yield=50%
31P RMN (101.25 MHz, CDCl₃): δ 24.7
¹H RMN (400.13 MHz, CDCl₃): δ 1.31 (t, ³$J_{HH}$=8.16 Hz, 3H, ⁶CH₃), 4.08 (m, 2H, ⁶CH₂), 6.97 (d, 1H, P—H), 7.44 (m, 2H, ³$CH_m$), 7.52 (s, 1H, P—H), 7.52 (m, 1H, ⁴$CH_p$), 7.70 (m, 2H, ²$CH_o$)

Ethyl diphenylhydrogenophosphinate (3.44)

Obtained from 4-biphenyl bromide.

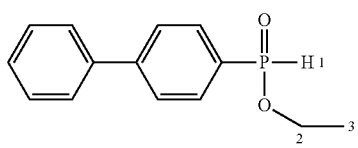

M (g/mol)=246.25
$C_{14}H_{15}O_2P$
Colorless oil
Yield=29%
31P RMN (101.25 MHz, CDCl₃): δ 24.8

¹H RMN (400.13 MHz, CDCl₃): δ 1.32 (t, ³$J_{HH}$=7.04 Hz, 3H, ⁵CH₃), 4.06 (m, 2H, ⁴CH₂), 6.84 (s, 1H, P—H), 7.29-7.81 (m, 9H, $CH_{Ar}$)

Ethyl para-methoxyphenylhydrogenophosphinate (3.49)

Obtained from 4-methoxyphenyl bromide.

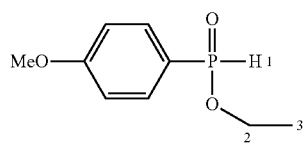

M (g/mol)=200.18
$C_9H_{13}O_3P$
Colorless oil
Yield=21%
³¹P RMN (101.25 MHz, CDCl₃): δ 23.4
¹H RMN (400.13 MHz, CDCl₃): δ 1.32 (t, ³$J_{HH}$=5.36 Hz, 3H, ⁶CH₃), 3.81 (s,3H, OCH₃), 4.09 (m, 2H, CH₂), 6.97 (d, ³$J_{HH}$=7.88 Hz, 2H, ³$CH_m$), 7.51 (s, 1H, P—H), 7.66 (d, ³$J_{HH}$=8.88 Hz, 2H, ²$CH_o$)

Ethyl meta-methoxyphenylhydrogenophosphinate (3.59)
Obtained from 3-anisyl bromide.

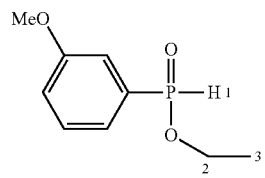

M (g/mol)=200.18
$C_9H_{13}O_3P$
Colorless oil
Yield=19%
31P RMN (101.25 MHz, CDCl₃): δ 24.76
¹H RMN (400.13 MHz, CDCl₃): δ 1.34 (t, ³$J_{HH}$=7.04 Hz, 3H, ⁷CH₃), 3.76 (s, 3H, OCH₃), 4.13 (m, 2H, ⁶CH₂), 7.08 (m, 1H, $CH_{Ar}$), 7.28 (m, 2H, $CH_{Ar}$), 7.38 (m, 1H, $CH_{Ar}$), 7.55 (d, ¹$J_{PH}$=564.77 Hz 1H, PH).

Ethyl para-methylphenylhydrogenophosphinate (3.60)

Obtained from 4-tolyl bromide.

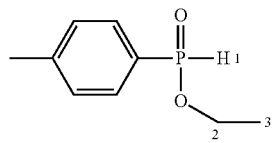

M (g/mol)=185.18
$C_9H_{14}O_2P$
Colorless oil
Yield=47%
³¹P RMN (101.25 MHz, CDCl₃): δ 25.2

$^1$H RMN (400.13 MHz, CDCl$_3$): δ 1.29 (t, $^3$J$_{HH}$=7.12 Hz, 3H, $^7$CH$_3$), 2.34 (s, 3H, CH$_3$), 4.06 (m, 2H, $^6$CH$_2$), 7.24 (d,$^3$J$_{HH}$=7.60 Hz, 2H, $^3$CH$_m$), 7.49 (s, 1H, P—H), 7.59 (d,$^3$J$_{HH}$=8.12 Hz, 2H, 2CH$_o$)

Ethyl meta-methylphenylhydrogenophosphinate (3.62)

Obtained from 3-tolyl bromide.

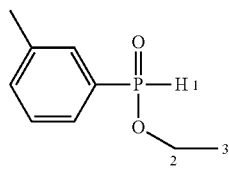

M (g/mol)=185.18
C$_9$H$_{14}$O$_2$P
Colorless oil
Yield=45%
$^{31}$P RMN (101.25 MHz, CDCl$_3$): δ 23.7
$^1$H RMN (400.13 MHz, CDCl$_3$): δ 1.30 (t, $^3$J$_{HH}$=7.04 Hz, 3H, $^7$CH$_3$), 2.31 (s, 3H, CH$_3$), 4.08 (m, 2H, $^6$CH$_2$), 7.31 (m, 2H, CH$_{Ar}$m), 7.47 (s, 1H, P—H), 7.48 (m, 2H, CH$_{Ar}$o)

Ethyl para-fluorophenylhydrogenophosphinate (3.63)

Obtained from 4-fluorophenyl bromide.

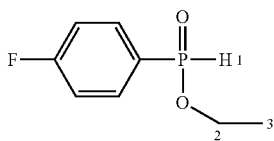

M (g/mol)=188.14
C$_8$H$_{10}$FO$_2$P
Colorless oil
Yield=31%
31P RMN (101.25 MHz, CDCl$_3$): δ 23.1
$^1$H RMN (400.13 MHz, CDCl$_3$): δ 1.31 (t, $^3$J$_{HH}$=8.08 Hz, 3H, $^5$CH$_3$), 4.08 (m, 2H, $^4$CH$_2$), 7.15 (m, 2H, $^3$CH$_m$), 7.25 (s, 1H, P—H), 7.74 (m, 2H, $^2$CH$_o$)

Ethyl meta-fluorophenylhydrogenophosphinate (3.68)

Obtained from 3-fluorophenyl bromide.

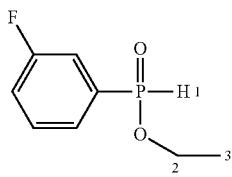

M (g/mol)=188.14
C$_8$H$_{10}$FO$_2$P
Colorless oil
Yield=20%

31P RMN (101.25 MHz, CDCl$_3$): δ 22.3
$^1$H RMN (400.13 MHz, CDCl$_3$): δ 1.30 (t, $^3$J$_{HH}$=6.84 Hz, 3H, $^7$CH$_3$), 4.09 (m, 2H, $^6$CH$_2$), 7.18-7.48 (m, 4H, CH$_{Ar}$), 7.49 (s, 1H, P—H)

Mannose protection: preparation of [2,3,5,6]-di-O-isopropylidene-D-Mannose

In a three-necked flask were introduced 50.8 g of D-mannose (0.282 mol), 2.5 L of acetone and 14.3 g of iodine sublimate (56.4 mmol, 0.2 eq.). The medium was stirred at room temperature until solubilization of mannose was complete (about 18 h). 640 ml of a 10% sodium thiosulfate aqueous solution were added. The pH value was brought back near to neutrality with a sodium hydrogenocarbonate saturated solution. After addition of the sodium chloride saturated solution, the organic phase was collected and extracted with chloroform. The combined organic phases were then dried on magnesium sulfate, filtered, and then evaporated. A yellow solid was produced, that was recristallized in a hexane/acetone mixture (80/20).

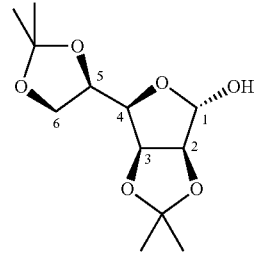

3.2

M (g/mol)=260.29
C$_7$H$_9$O$_2$P (N° CAS 7757-38-2)
Translucent crystals (62.4 g)
Yield=85%
$^1$H NMR (400.13 MHz, CDCl$_3$): δ 1.34 (s, 3H, CH$_3$), 1.39 (s, 3H, CH$_3$), 1.47 (s, 3H, CH$_3$), 1.48 (s, 3H, CH$_3$), 3.45 (d, 1H, $^3$J$_{H-H}$=2.4 Hz, OH), 4.08 (dd, 2H, $^2$J$_{H-H}$5.5 Hz, $^3$J$_{H-H}$=1.0 Hz, $^6$CH$_2$), 4.19 (dd, 1H, $^3$J$_{H-H}$=7.0 Hz, $^3$J$_{H-H}$=3.7 Hz, $^4$CH), 4.41 (q broad, 1H, $^3$J$_{H-H}$=5.5 Hz, $^5$CH), 4.62 (d, 1H, $^3$J$_{H-H}$=5.9 Hz, $^2$CH), 4.82 (dd, 2H, $^3$J$_{H-H}$=5.9 Hz, $^3$J$_{H-H}$=3.7 Hz, $^3$CH), 5.39 (d, 1H, $^3$J$_{H-H}$=2.1 Hz, $^1$CH).

2,3: 5,6-Di-O-isopropylidene-N-benzyl-D-mannosyl amine

In a three-necked flask were introduced 10 g of protected D-mannose (38 mmol), 100 ml of ethanol, 10 g of magnesium sulfate and 7.5 ml of distilled benzylamine (57 mmol, 1.5 eq.). The medium was stirred at reflux for 48 hours.

The medium was filtered on Celite, the obtained filtrate was evaporated under reduced pressure. The oily residue was directly purified on a silica gel column using a dichloromethane/ethyl acetate system according to a gradient of from 100/0 to 50/50. The product was obtained as a yellow oil.

3.24

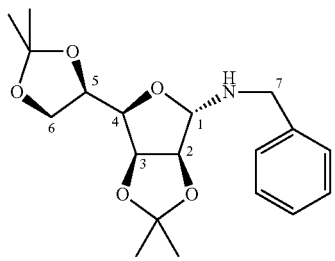

M (g/mol)=349.43
$C_{19}H_{27}O_5N$
Yellow oil
Yield=58%
$^1$H NMR (400.13 MHz, CDCl$_3$): δ 1.19 (s, 3H, CH$_3$), 1.24 (s, 3H, CH$_3$), 1.30 (s, 3H, CH$_3$), 1.38 (s, 3H, CH$_3$), 3.30 (dd, 1H, $^3J_{H-H}$=3.3 Hz, $^3J_{H-H}$=7.6 Hz, $^4$CH), 3.67 (dd, 1H, $^3J_{H-H}$=5.9 Hz, $^3J_{H-H}$=7.2 Hz, $^5$CH), 3.81 (dd, 1H, $^2J_{H-H}$=3.8 Hz, $^3J_{H-H}$=2.0 Hz, $^2$CH), 3.97 (m, 2H, $^6$CH$_2$), 4.29 (td, 1H, $^3J_{H-H}$=3.3 Hz, $^3$CH), 4.48 (ddd, 2H, $^2J_{H-H}$=41.8 Hz, $^3J_{H-H}$6.3 Hz, $^2J_{H-H}$=3.5 Hz, $^7$CH$_2$), 4.66 (dd, 1H, $^3J_{H-H}$=5.1 Hz, $^3J_{H-H}$=3.6 Hz, $^1$CH), 4.81 (s, 1H, NH), 7.22-7.47 (m, 5H, CH$_{Ar}$).

2,3: 5,6-Di-O-isopropylidene-N-phenyl-D-mannosyl amine

In a 250 ml three-necked flask were introduced 15 g of protected D-mannose (58 mmol), 150 ml of ethanol, 15 g of magnesium sulfate and 16.5 ml of distilled aniline (181 mmol, 3 eq.). The medium was stirred at reflux for 24 hours.

The medium was filtered on Celite, the obtained filtrate was evaporated under reduced pressure up to 30% of the initial volume. After a couple of hours at 4° C., the expected product did precipitate. After a first filtration, petroleum ether was added to the filtrate so as to precipitate the rest.

3.25

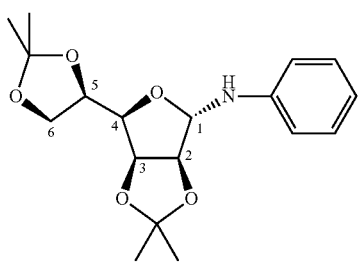

M (g/mol)=335.44
$C_{18}H_{25}NO_5$
White solid
Yield=90%
$^1$H RMN (400.13 MHz, CDCl$_3$): δ 1.31 (s, 3H, CH$_3$), 1.34 (s, 3H, CH$_3$), 1.39 (s, 3H, CH$_3$), 1.48 (s, 3H, CH$_3$), 3.46 (dd, 1H, $^3J_{H-H}$=3.3 Hz, $^3J_{H-H}$=8.4 Hz, $^4$CH), 4.02 (m, 2H, $^6$CH$_2$), 4.37 (qd, 1H, $^3J_{H-H}$=4.5 Hz, $^3J_{H-H}$=5.7 Hz,$^3J_{H-H}$=8.6 Hz, $^5$CH), 4.63 (dd, 1H, $^2J_{H-H}$=6.1 Hz, $^3J_{H-H}$=3.5 Hz, $^2$CH), 4.72 (dd, 1H, $^2J_{H-H}$=6.1 Hz, $^3J_{H-H}$=3.3 Hz, $^3$CH), 4.93 (m, 2H, $^1$CH+NH), 6.72-7.13 (m, 5H, CH$_{Ar}$).

2,3: 5,6-Di-O-isopropylidene-N-p-tolyl-D-mannosyl amine

In a 250 ml three-necked flask were introduced 15.1 g of protected D-mannose (58 mmol), 100 ml of ethanol, 15 g of magnesium sulfate and 12.2 g of freshly recristallized toluidine (181 mmol, 3 eq.). The medium was stirred at reflux for 24 hours.

The reaction medium was cooled at room temperature whereby causing the precipitation of the expected protected sugar. The medium was filtered on sintered glass, the filtrate was introduced at 4° C. for 4 hours allowing the rest of the compound to precipitate. The whole solid was solubilized in dichloromethane, then filtered to remove magnesium sulfate. The filtrate was then evaporated under reduced pressure to produce a white solid.

3.26

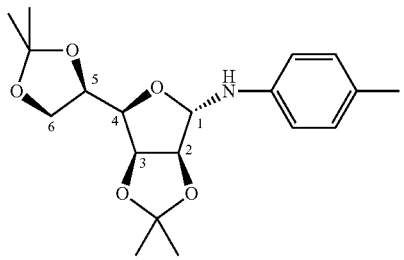

M (g/mol)=349.43
$C_{19}H_{27}O_5N$
White solid
Yield=65%
$^1$H RMN (400.13 MHz, CDCl$_3$): δ 1.40 (s, 3H, CH$_3$), 1.44 (s, 3H, CH$_3$), 1.49 (s, 3H, CH$_3$), 1.58 (s, 3H, CH$_3$), 2.27 (s, 3H, CH$_3$tol), 3.53 (dd, 1H, $^3J_{H-H}$=3.3 Hz, $^3J_{H-H}$=8.5 Hz, $^4$CH), 4.12 (m, 2H, $^6$CH$_2$), 4.47 (m, 1H, $^5$CH), 4.71 (q, 1H, $^3J_{H-H}$=6.0 Hz,$^3J_{H-H}$=3.2 Hz, $^2$CH), 4.82 (q, 1H, $^3J_{H-H}$=6.0 Hz, $^3J_{H-H}$=3.2 Hz, $^3$CH), 4.91 (d, 1H, $^3J_{H-H}$=10.0 Hz, NH), 5.03 (q, 1H, $^3J_{H-H}$=10.0 Hz, $^3J_{H-H}$=3.2 Hz, $^1$CH), 6.72-7.01 (m, 4H, CH$_{Ar}$).

The following compound was also prepared similarly to compounds 3.24 to 3.26:

2,3:
5,6-Di-O-isopropylidene-N-naphthyl-D-mannosylamine
(3.27)

3.27

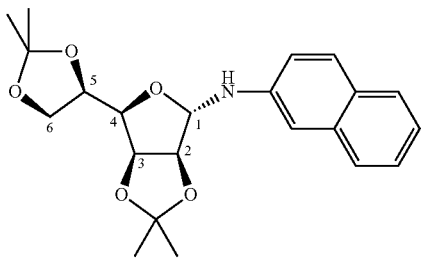

2,3,5-tri-O-benzyl-D-arabinofuranose (3.45)

In a 500 ml two-necked flask covered with a condenser were introduced 7 g of arabinose (0.043 mol), 7.5 g of magnesium sulfate, 300 ml of methanol and 2.3 ml of sulfuric acid. This medium was stirred at room temperature for 5 hours prior to being neutralized through an Amberlite IRA 400 resin. The resin was washed again twice with 100 ml of methanol. The phases were then combined and evaporated under reduced pressure. This crude product did undergo two coevaporations with tetrahydrofuran to produce a slightly viscous white solid.

The resulting solid residue was then introduced in a 250 ml two-necked flask covered with a condenser. 100 ml of THF were added, then 15 g of magnesium sulfate, 78 g of powdered potassium hydroxide and 100 ml of benzyl chloride. This heterogenous medium was then refluxed with THF under very vigourous mechanical stirring for 24 hours. The crude product was then filtered on Celite, and the obtained filtrate was evaporated under reduced pressure with a vane pump. A yellow syrup was obtained.

The syrup obtained was taken up in 200 ml of glacial acetic acid and 30 ml of hydrochloric acid 6N. The medium was then stirred at 65° C. for 1 hour. The medium was concentrated up to one third of the initial volume, and then was poured onto a water/ice bath. Decantation of the organic phase and new extraction of the aqueous phase from dichloromethane.

The organic phases were then combined, dryed then evaporated under reduced pressure, to produce a coloured oil. Crude product purification on a silica gel column using a dichloromethane-hexane system.

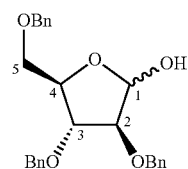

3.45

M (g/mol)=420.21
$C_{26}H_{28}O_5$
White solid (7.1 g)
Yield=43%
$^1$H NMR (400.13 MHz, CDCl$_3$): δ 3.56 (qd, 1H, $^2J_{H-H}$=20.1 Hz, $^3J_{H-H}$=3.8 Hz, $^3J_{H-H}$=10.1 Hz, $^5CH_2$), 3.91 (d, 1H, $^3J_{H-H}$=10.1 Hz, OH), 4.05 (t, 1H, $^3J_{H-H}$=4.6 Hz, $^3CH$), 4.12 (q, 1H, $^3J_{H-H}$=4.2 Hz, $^3J_{H-H}$=8.3 Hz, $^4CH$), 4.21 (q, 1H, $^3J_{H-H}$=4.6 Hz, $^3J_{H-H}$=9.3 Hz, $^2CH$), 4.65 (m, 6H, CH$_2$OBn), 5.35 (dd, 1H, $^3J_{H-H}$=6.0 Hz, $^3J_{H-H}$=3.2 Hz, $^1CH$),7.28-7.34 (m, 15H, CH$_{Ar}$).

2,3,5-tri-O-benzyl-N-benzyl-D-arabinosylamine (3.78)

This compound was prepared similarly to compounds 3.24 to 3.26, starting from precursor 3.45 and benzylamine.

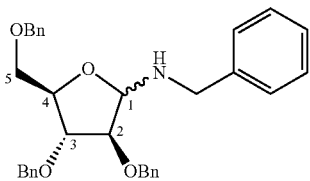 [SMILES: c1ccc(CNC2O[C@H](COCc3ccccc3)[C@@H](OCc3ccccc3)[C@@H]2OCc2ccccc2)cc1]

2,3: 5,6-Di-O-isopropylidene-1-O-trichloroacetami-doyl-D-mannofuranose

In a Schlenk tube that had been previously deoxygenated, under nitrogen atmosphere, were introduced 0.5 g of pro-tected mannose (1.92 mmol), 15 ml of dichloromethane and 1 ml of trichloroacetonitrile (19.2 mmol, 10 eq.). 55 mg of sodium hydride (2.3 mmol, 1.2 eq.) were then added and the medium was stirred for one hour at room temperature.

The reaction medium was then filtered on Celite. The obtained filtrate was evaporated under reduced pressure to produce a slightly coloured oil.

This oil was then triturated in hexane thus resulting in a white precipitate. After the filtration, the filtration product was evaporated to produce a yellow oil that did spontaneously crystallize. Such solid corresponds to the pure trichloroaceta-midate derivative.

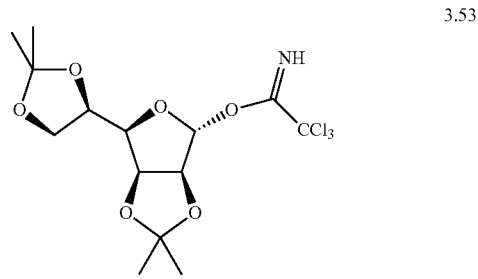

3.53

M (g/mol)=403.45
$C_{14}H_{20}NO_6Cl_3$
Yellow solid
Yield=89%
$^1$H NMR (400.13 MHz, (CD)$_3$CO): δ 1.39 (s, 3H, CH$_3$), 1.40 (s, 3H, CH$_3$), 1.47 (s, 3H, CH$_3$), 1.53 (s, 3H, CH$_3$), 4.02 (AB, 2H, $^6$CH$_2$), 4.22 (dd, 1H, $^3J_{H-H}$=7.2 Hz, $^3J_{H-H}$=3.7 Hz, $^4$CH), 4.39 (q, 1H, $^5$CH), 4.92 (d, 1H, $^3J_{H-H}$=6.1 Hz, $^2$CH), 4.99 (dd, 1H, $^3J_{H-H}$=5.9 Hz, $^3J_{H-H}$=3.3 Hz, $^3$CH), 6.31 (s, 1H, $^1$CH), 8.61 (sl, 1H, NH).

The Phosphinosugars 3.3 Prepared Below are Not Compounds According to the Invention, but they have been Used During Many Synthesis Procedures as Precursors for Compounds of the Invention.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-ol In a Schlenk tube that had been previously deoxygenated were introduced under nitrogen atmosphere 30.25 g of [2,3-5,6]-di-O-isopropylidene-D-mannofuranose (0.116 mol), 2.4 g of potassium tert-butoxide (0.023 mol, 0.2 eq.) and 150 ml of anhydrous THF. 15 ml of methyl phenyl hydrogenophos-phinate (0.116 mol, 1 eq.) were then added dropwise at room temperature under mechanical stirring. This medium was then stirred at room temperature for 15 hours.

The reaction medium was filtered on sintered glass and the white precipitate obtained was rinsed with THF. The compound did correspond to the first pure diastereomer I (3.3a) (δ=31.4 ppm) (13.6 g). A sodium chloride saturated solution was then added to the filtrate. The aqueous phase thus obtained was extracted three times from dichloromethane. The organic phases were then combined, dried on magnesium sulfate, filtered, and then evaporated under reduced pressure to produce a coloured oil. This residue taken up in diethyl ether resulted in the selective precipitation of the diastereoi-somer 3.3a that had been previously isolated. The filtration product was evaporated, and then purified by means of a silica gel flash chromatography. The eluent ether/AcOEt system (100/0-50/50) could isolate the three other impure diastereomers (3.3b, 3.3c and 3.3d) that were later easily purified by recrystallization in hexane.

3.3

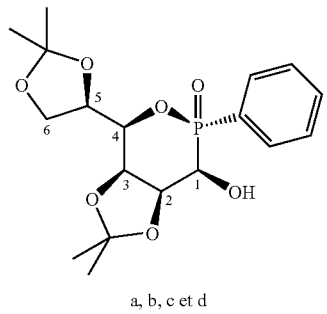

a, b, c et d

M (g/mol)=384.37
$C_{18}H_{25}O_7P$
White solid
4 diastereomers, 3.3a, 3.3b, 3.3c and 3.3d
Overall yield=85%
Dia I 3.3a Yield=35%
$^1$H NMR (400.13 MHz, CDCl$_3$): δ 1.41 (s, 3H, CH$_3$), 1.44 (s, 3H, CH$_3$), 1.47 (s, 3H, CH$_3$), 1.71 (s, 3H, CH$_3$), 3.25 (dd, 1H, $^3J_{H-H}$=3.1 Hz, $^2J_{H-H}$=11.7 Hz, OH), 4.04 (dd, 1H, $^3J_{H-H}$=4.1 Hz, $^3J_{H-H}$=11.7 Hz, $^1$CH), 4.13 (m, 1H, $^4$CH), 4.17 (m, 2H, $^6$CH$_2$), 4.47 (q, 1H, $^3J_{H-H}$=5.5 Hz, $^3J_{H-H}$=12.1 Hz, $^5$CH), 4.65 (dd, 1H, $^3J_{H-H}$=7.9 Hz, $^3J_{H-H}$=1.3 Hz, $^3$CH), 4.84 (ddd, 1H, $^3J_{H-H}$=4.1 Hz, $^3J_{H-H}$=24.6 Hz, $^3J_{H-H}$=7.9 Hz, $^2$CH), 7.50-7.86 (m, 5H CH$_{Ar}$).
MS HR$^+$ (NBA): Theoretical mass 384.1416; Experimental mass 384.1431.
Dia II 3.3b Yield=13%
$^1$H NMR (400.13 MHz, CDCl$_3$): δ 1.38 (s, 3H, CH$_3$), 1.40 (s, 3H, CH$_3$), 1.43 (s, 3H, CH$_3$), 1.57 (s, 3H, CH$_3$), 4.14 (m, 2H, $^6$CH$_2$), 4.26 (ddd, 1H, $^3J_{H-H}$=1.9 Hz, $^2J_{H-H}$=8.1 Hz, $^3J_{H-H}$=6.0 Hz, $^4$CH), 4.48 (m, 1H, $^5$CH), 4.59 (dd, 1H, $^3J_{H-H}$=3.5 Hz, $^3J_{H-H}$=13.7 Hz, $^1$CH), 4.64 (dd, 1H, $^3J_{H-H}$=1.3 Hz, $^3J_{H-H}$=7.6 Hz, $^3$CH), 4.88 (ddd, 1H, $^3J_{H-H}$=7.6 Hz, $^3J_{H-H}$=3.5 Hz, $^3J_{P-H}$=26.8 Hz, $^2$CH), 7.49-7.73 (m, 5H CH$_{Ar}$).
MS HR$^+$ (NBA): Theoretical mass 384.1416; Experimental mass 384.1429.
Dia III 3.3c Yield=14%
$^1$H NMR (400.13 MHz, CDCl$_3$): δ 1.31 (s, 3H, CH$_3$), 1.33 (s, 3H, CH$_3$), 1.38 (s, 3H, CH$_3$), 1.41 (s, 3H, CH$_3$), 4.03 (m, 2H, $^6$CH$_2$), 4.15 (dl, 1H, OH), 4.30 (dd, 1H, $^3J_{H-H}$=6.3 Hz,$^3J_{P-H}$=3.6 Hz, $^1$CH), 4.35 (m, 1H, $^5$CH), 4.52 (m, 1H, $^4$CH), 4.60 (td, 1H,$^3J_{H-H}$=1.7 Hz, $^3J_{P-H}$=7.2 Hz, $^3$CH), 4.88 (ddd, 1H,$^3J_{H-H}$=3.6 Hz, $^3J_{P-H}$=24.5 Hz, $^3J_{H-H}$=7.2 Hz, $^2$CH), 7.38-7.89 (m, 5H, CH$_{Ar}$).
MS HR$^+$ (NBA): Theoretical mass 384.1416; Experimental mass 384.1402.
[α]$_D^{25}$=+50 (c=0.19. MeOH)
Dia IV, 3.3d Yield=34%
$^1$H NMR (400.13 MHz, CDCl$_3$): δ 1.26 (s, 3H, CH$_3$), 1.31 (s, 3H, CH$_3$), 1.36 (s, 3H, CH$_3$), 1.57 (s, 3H, CH$_3$), 3.96 (qd, 1H, $^3J_{H-H}$=1.5 Hz, $^2J_{H-H}$=2.2 Hz, $^2J_{H-H}$=6.7 Hz, $^4$CH), 4.02 (m, 2H, $^6$CH$_2$), 4.15 (dl, 1H, $^2J_{P-H}$=3.6 Hz, $^1$CH), 4.34 (q, 1H, $^3J_{H-H}$=6.1 Hz, $^3J_{H-H}$=11.4 Hz, $^5$CH), 4.45 (dL, 1H, $^3J_{H-H}$=8.1 Hz, $^3$CH), 4.79 (ddd, 1H, $^3J_{H-H}$=3.6 Hz, $^3J_{P-H}$=24.7 Hz, $^3J_{H-H}$=8.1 Hz, $^2$CH), 7.50-7.86 (m, 5H CH$_{Ar}$).
MS HR$^+$ (NBA): Theoretical mass 384.1416; Experimental mass 384.1415.
[=]D$^{25}$=+62 (c=0.20, MeOH).

C) Preparation of Compounds of Formula (1) According to the Invention

Most of the following phosphinosugars have been prepared similarly to compounds 3.3. Treatment of the reaction mixture was achieved by addition of 0.1 N hydrochloric acid, sodium chloride saturated solution and 50 ml of chloroform. The aqueous phase was extracted with chloroform. The organic phases were combined, dried on magnesium sulfate and evaporated under reduced pressure. The thus obtained oily residue was then purified on a silica gel column (ether/AcOEt gradient ranging from 100/0 to 50/50).

4-(2,2-Dimethyl-[1,3]dioxolan-4-yl)-2,2-dimethyl-2-oxo-2-[4-tolyl]-tetrahydro-6λ*5*-[1,3]dioxolo[4,5-d][1,2]oxaphosphinan-3-ol (3.37)

This compound was obtained from [2,3-5,6]-di-O-isopropylidene-D-mannofuranose and ethyl tolylhydrogenophosphinate.

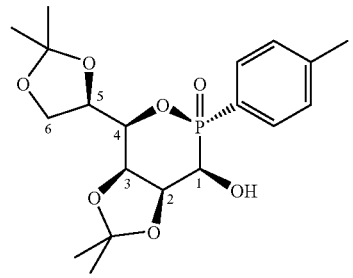

M(g/mol)=398.40
$C_{19}H_{27}NO_7P$
4 diastereomers
Yield=32%
$^{31}$P RMN (101.25 MHz, CDCl$_3$): δ 32.3 $^1$H RMN (400.13 MHz, CDCl$_3$): δ1.38 (s, 3H, CH$_3$), 1.40 (s, 3H, CH$_3$), 1.44 (s, 3H, CH$_3$), 1.67 (s, 3H, CH$_3$), 2.40 (s, 3H, CH$_3$), 3.48 (dd, $^3J_{HH}$=11.47 Hz, $^3J_{PH}$=3.87 Hz, 1H, OH), 4.01 (dd, $^3J_{HH}$=4.11 Hz, $^3J_{HH}$=11.47 Hz, 1H, $^1$CH), 4.10 (ddd, $^3J_{HH}$=1.21 Hz, $^3J_{HH}$=6.91 Hz, $^3J_{PH}$=2.36 Hz, 1H, $^4$CH), 4.11 (dd, $^2J_{HH}$=9.00 Hz, $^3J_{HH}$=5.08 Hz, 1H, $^6$CH), 4.13 (dd, $^2J_{HH}$=9.00 Hz, $^3J_{HH}$=5.86 Hz, 1H, $^6$CH), 4.43 (ddd, $^3J_{HH}$=5.86 Hz, $^3J_{HH}$=5.08 Hz, $^3J_{HH}$=6.91 Hz, 1H, $^5$CH), 4.62 (ddd, $^3J_{HH}$=7.94 Hz, $^3J_{HH}$=1.21 Hz, $^4J_{PH}$=1.08 Hz, 1H, $^3$CH), 4.81 (ddd, $^3J_{PH}$=24.59 Hz, $^3J_{HH}$=4.11 Hz, $^3J_{HH}$=7.54 Hz, 1H, $^2$CH), 7.29 (dd, $^3J_{HH}$=2.92 Hz, $^4$J7.16 Hz, 2H, CH$_{Arom}$), 7.69 (dd, $^3J_{HH}$=10.08 Hz, $^4$J =12.00 Hz, 2H, CH$_{Arom}$)

4-(2,2-Dimethyl-[1,3]dioxolan-4-yl)-2,2-dimethyl-2-oxo-2-[4-fluorophenyl]-tetrahydro-6λ*5*-[1,3]dioxolo[4,5-d][1,2]oxaphosphinan-3-ol (3.38)

This compound was obtained from [2,3-5,6]-di-O-isopropylidene-D-mannofuranose and ethyl p-fluorophenylhydrogenophosphinate.

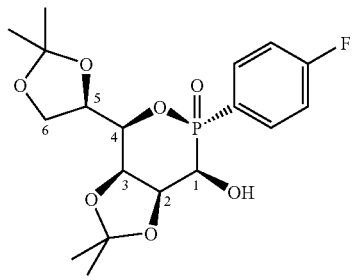 [SMILES: CC1(C)O[C@H]2[C@@H]([C@H]3COC(C)(C)O3)O[P@@](=O)(c3ccc(F)cc3)[C@@H](O)[C@H]2O1]

M(g/mol)=398.40

C$_{18}$H$_{24}$FO$_7$P 4 diastereomers

Yield=32%

$^{31}$P RMN (101.25 MHz, CDCl$_3$): δ 30.1

4-(2,2-Dimethyl-[1,3]dioxolan-4-yl)-2,2-dimethyl-2-oxo-2-[4-methoxyphenyl]-tetrahydro-6λ*5*-[1,3]dioxolo[4,5-d][1,2]oxaphosphinan-3-ol (3.39)

This compound was obtained from [2,3-5,6]-di-O-isopropylidene-D-mannofuranose and ethyl p-methoxyphenylhydrogenophosphinate.

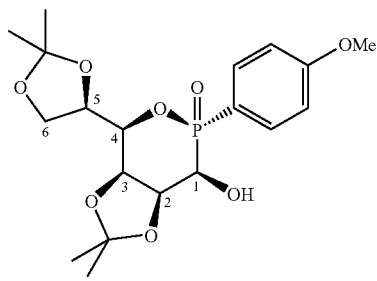 [SMILES: COc1ccc([P@]2(=O)O[C@H]([C@H]3COC(C)(C)O3)[C@@H]3OC(C)(C)O[C@@H]3[C@@H]2O)cc1]

M(g/mol)=414.14

C$_{19}$H$_{27}$NO$_8$P 4 diastereomers

Yield=16%

$^{31}$P RMN (101.25 MHz, CDCl$_3$): δ 31.1

$^1$H RMN (400.13 MHz, CDCl$_3$): δ 1.39 (s, 3H, CH$_3$), 1.42 (s, 3H, CH$_3$), 1.45 (s, 3H, CH$_3$), 1.68 (s, 3H, CH$_3$), 2.39 (s, 3H, CH$_3$), 3.42 (dd, $^3J_{HH}$=11.19 Hz, $^3J_{3.79}$ Hz, 1H, OH), 4.06 (dd, $^3J_{HH}$=11.70 Hz, $^3J_{HH}$=4.07 Hz, 1H, $^1$CH), 4.14 (m, 3H, $^5$CH et $^6$CH$_2$), 4.44 (dd, $^3J_{HH}$=5.85 Hz, $^3J_{HH}$=11.95, 1 H, $^4$CH), 4.62 (dd, $^3J_{HH}$=7.88 Hz, $^3J_{HH}$=1.52 Hz, 1H, $^3$CH), 4.82 (ddd, $^3J_{PH}$=24.50 Hz, $^3J_{HH}$=4.07 Hz, $^3J_{HH}$=7.54 Hz, 1H, $^2$CH), 7.38 (m, 2H, CH$_{Arom}$).

4-(2,2-Dimethyl-[1,3]dioxolan-4-yl)-2,2-dimethyl-2-oxo-2-[3-tolyl]-tetrahydro-6λ*5*-[1,3]dioxolo[4,5-d][1,2]oxaphosphinan-3-ol (3.40)

This compound was obtained from [2,3-5,6]-di-O-isopropylidene-D-mannofuranose and ethyl m-methylphenylhydrogenophosphinate.

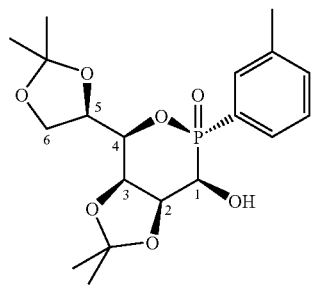 [SMILES: Cc1cccc([P@]2(=O)O[C@H]([C@H]3COC(C)(C)O3)[C@@H]3OC(C)(C)O[C@@H]3[C@@H]2O)c1]

M(g/mol)=398.15

C$_{19}$H$_{27}$NO$_7$P 4 diastereomers

Yield=33%

$^{31}$P RMN (400.13 MHz, CDCl$_3$): δ 31.0 $^1$H RMN (400.13 MHz, CDCl$_3$): δ 1.40 (s, 3H, CH$_3$), 1.42 (s, 3H, CH$_3$), 1.46 (s, 3H, CH$_3$), 1.69 (s, 3H, CH$_3$), 2.40 (s, 3H, CH$_3$), 3.37 (dd, $^3J_{HH}$=11.45 Hz, $^3J_{Ph}$=4.05 Hz, 1H, OH), 4.02 (dd, $^3J_{HH}$=4.07 Hz, $^3J_{HH}$=11.70 Hz, 1H, $^1$CH), 4.14 (m, 3H, $^6$CH$_2$ et $^5$CH), 4.44 (ddd, $^3J_{HH}$=5.85 Hz, $^3J_{HH}$=5.60 Hz, $^3J_{HH}$=6.35 Hz, 1H, $^5$CH), 4.62 (ddd, $^3J_{HH}$=7.88 Hz, $^3J_{HH}$=1.27 Hz, $^4J_{PH}$=1.01 Hz, 1H, $^3$CH), 4.82 (ddd, $^3J_1D_H$=24.50 Hz, $^3J_{HH}$=4.32 Hz, $^3J_{HH}$=7.88 Hz, 1H, $^2$CH), 7.38 (m, 2H, CH$_{Arom}$), 7.58 (m, 1H, CH$_{Arom}$), 7.66 (S$_{large}$, 1H, CH$_{Arom}$)

4-(2,2-Dimethyl-[1,3]dioxolan-4-yl)-2,2-dimethyl-2-oxo-2-[4-diphenyl]-tetrahydro-6λ*5*-[1,3]dioxolo[4,5-d][1,2]oxaphosphinan-3-ol (3.41)

This compound was obtained from [2,3-5,6]-di-O-isopropylidene-D-mannofuranose and ethyl diphenylhydrogenophosphinate.

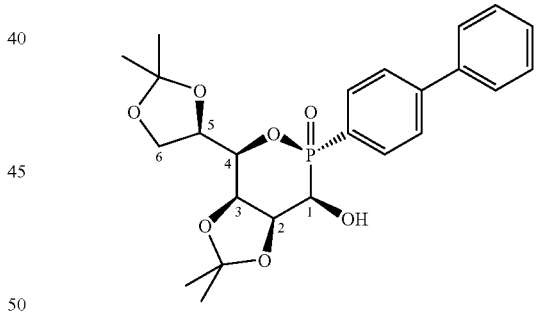

M(g/mol)=460.17

C$_{24}$H$_{29}$O$_7$P 4 diastereomers

Yield=53%

$^{31}$P RMN (101.25 MHz, CDCl$_3$): δ 40.2

$^1$H RMN (400.13 MHz, CDCl$_3$): δ1.32 (s, 3H, CH$_3$), 1.36 (s, 3H, CH$_3$), 1.40 (s, 3H, CH$_3$), 1.52 (s, 3H, CH$_3$), 4.05 (m, $^3J_{HH}$=5.85 Hz, $^3J_{HH}$=9.15 Hz, 2H, $^6$CH$_2$), 4.17 (dd, $^2J_{HH}$=8.39 Hz, $^3J_{HH}$=1.52 Hz, 1H, $^1$CH), 4.40 (m, 1H, $^5$CH), 4.53 (d, $^3J_{HH}$=2.8 Hz, 1H, OH), 4.56 (dd, $^3J_{HH}$=1.52 Hz, $^3J_{HH}$=7.37 Hz, 1H, $^3$CH), 4.82 (dd, $^3J_{HH}$=3.30 Hz, $^3J_{HH}$=$^3J_{HH}$=7.37 Hz, 1H, $^2$CH), 7.33 (m, 3H, CH$_{Arom}$), 7.43 (dd, $^3J_{HH}$=2.03 Hz, $^3J_{HH}$=7.63 Hz, 2H, CH$_{Arom}$), 7.52 (d, $^3J_{HH}$=8.14 Hz, 2H, CH$_{Arom}$), 7.97 (d, $^3J_{HH}$=8.13 Hz, 2H, CH$_{Arom}$).

4-(2,2-Dimethyl-[1,3]dioxolan-4-yl)-2,2-dimethyl-2-oxo-2-phenyl-tetrahydro-6λ*5*-[1,3]dioxolo[1,2]oxaphosphinan-3-O-benzyl (3.77)

This compound was obtained by alkylation of compound 3.3 with benzyl chloride.

3.61

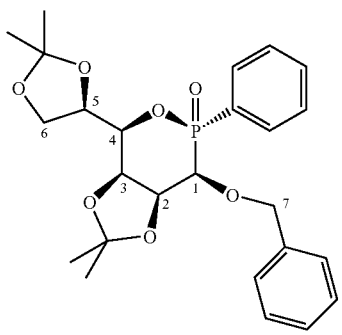

M(g/mol)=474.50
$C_{25}H_{31}NO_7P$
Yield=91%
$^{31}$P RMN (161.97 MHz, CDCl$_3$): δ 25.5
$^1$H RMN (400.13 MHz, CDCl$_3$): δ 1.37 (s, 3H, CH$_3$), 1.42 (s, 3H, CH$_3$), 1.44 (s, 3H, CH$_3$), 1.74 (s, 3H, CH$_3$), 3.84 (d, 1H, $^3J_{H-H}$=3.3 Hz, $^1$CH), 4.03 (m, 2H, $^6$CH$_2$), 4.11 (dd, 1H, $^3J_{H-H}$=9.1 Hz, $^2J_{H-H}$=6.1, $^4$CH), 4.44 (m, 1H, $^3$CH), 4.62 (m, 3H, $^5$CH+$^7$CH$_2$) 4.90 (ddd, 1H, $^3J_{P-H}$=23.8 Hz, $^3J_{H-H}$=3.3 Hz, $^2J_{H-H}$=8.1 Hz, $^2$CH), 7.00-7.83 (m, 10H, CH$_{Ar}$).
MS Q-TOF: m/z (%) 475.22 [M+H$^+$] (90%).

4-(2,2-Dimethyl[1,3]dioxolan-4-yl)-2,2-dimethyl-2-oxo-2-butyl-tetrahydro-6λ*5*-[1,3]dioxolo[4,5-d][1,2]oxaphosphinan-3-ol This compound was prepared similarly to compound 3.3, starting from 2,3: 5,6-Di-O-isopropylidene-D-mannofuranose and ethyl butylhydrogenophosphinate 3.34.

3.66

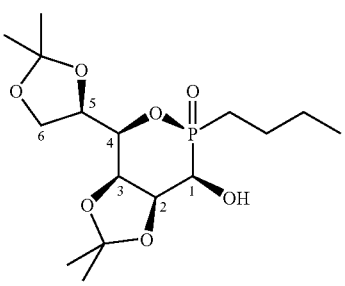

M(g/mol)=364,38
$C_{16}H_{29}O_7P$
2 diastereomers
Yield$_{(overall)}$=41%
Dia I $^{31}$P RMN (161.97 MHz, CDCl$_3$): δ 45.4
$^1$H RMN (400.13 MHz, CDCl$_3$): δ 0.92 (t, 3H, CH$_3$Bu), 1.36 (s, 3H, CH$_3$), 1.37 (s, 3H, CH$_3$), 1.42 (s, 3H, CH$_3$), 1.43 (m, 2H, CH$_2$Bu), 1.59 (s, 3H, CH$_3$), 1.62-1.94 (m, 4H, CH$_2$Bu), 3.35 (ddd, 1H, OH), 3.77 (dd, 1H, $^3J_{H-H}$=1.3 Hz, $^3J_{H-H}$=3.1 Hz, $^2J_{P-H}$=7.3 Hz, $^4$CH), 3.82 (dd, 1H, $^3J_{H-H}$=2.5 Hz, $^2J_{P-H}$=10.8 Hz, $^1$CH), 4.04 (AB, 2H, $^6$CH$_2$), 4.36 (m, 1H, $^5$CH), 4.54 (dl, 1H, $^3H_{H-H}$=7.8 Hz, $^3$CH), 4.76 (ddd, 1H, $^3J_{P-H}$=23.0 Hz, $^3J_{H-H}$=3.8 $^3J_{H-H}$=7.8 Hz, $^2$CH).
MS FAB$^+$ (NBA): m/z (%) 365.19 [M+H$^+$](80%), 366.22 [M+2H$^+$](10%), 729.39 [2M+H$^+$](10%).
Dia II $^{31}$P RMN (161.97 MHz, CDCl$_3$): δ 49.3

4-(2,2-Dimethyl-[1,3]dioxolan-4-yl)-2,2-dimethyl-2-oxo-2-octyl-tetrahydro-6λ*5*-[1,3]dioxolo[4,5-d][1,2]oxaphosphinan-3-ol (3.42)

This compound was prepared similarly to compound 3.3, starting from 2,3: 5,6-Di-O-isopropylidene-D-mannofuranose and ethyl octylhydrogenophosphinate 3.13.

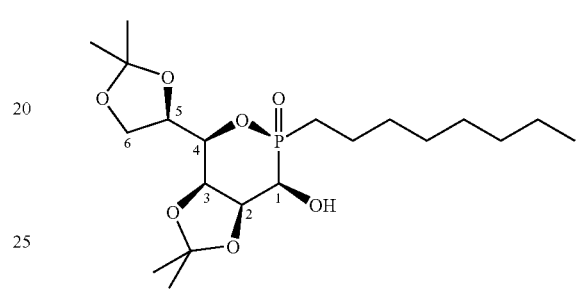

M(g/mol)=420.49
$C_{20}H_{37}O_7P$
3 diastereomers
Yield$_{(overall)}$=39%
Dia I $^{31}$P RMN (161.97 MHz, CDCl$_3$): δ 41.3
Dia II $^{31}$P RMN (161.97 MHz, CDCl$_3$): δ 45.7
Dia III $^{31}$P RMN (161.97 MHz, CDCl$_3$): δ 48.9

4-(2,2-Dimethyl-[1,3]dioxolan-4-yl)-2,2-dimethyl-2-oxo-2-phenylpropyl-tetrahydro-6λ*5*-[1,3]dioxolo[4,5-d][1,2]oxaphosphinan-3-ol (3.43)

This compound was prepared similarly to compound 3.3, starting from 2,3: 5,6-Di-O-isopropylidene-D-mannofuranose and ethyl phenylpropylhydrogenophosphinate 3.23.

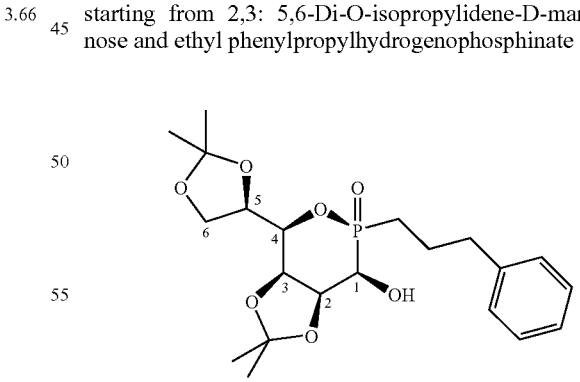

M(g/mol)=412.42
$C_{20}H_{29}O_7P$
2 diastereomers
Yield$_{(overall)}$=35%
Dia I $^{31}$P RMN (161.97 MHz, CDCl$_3$): δ 45.4
Dia II $^{31}$P RMN (161.97 MHz, CDCl$_3$): δ 48.5

4-(2,2-Dimethyl-[1,3]dioxolan-4-yl)-2,2-dimethyl-2-oxo-2-ethyl-tetrahydro-6λ*5*-[1,3]dioxolo[4,5-d][1,2]oxaphosphinan-3-ol This compound was prepared similarly to compound 3.3, starting from 2,3: 5,6-Di-O-isopropylidene-D-mannofuranose and ethyl ethylhydrogenophosphinate 3.17.

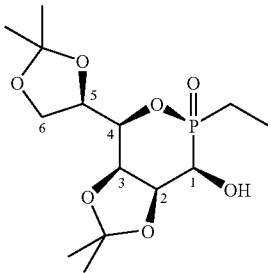

3.65

M(g/mol)=336,32
$C_{14}H_{25}O_7P$
4 diastereomers
Yield$_{(overall)}$=42%
Dia I
$^{31}$P RMN (161.97 MHz, CDCl$_3$): δ 46.6
$^1$H RMN (400.13 MHz, CDCl$_3$): δ 1.23 (td, 3H, $^2J_{P-H}$=18.2 Hz, CH$_3$Et), 1.36 (s, 3H, CH$_3$), 1.38 (s, 3H, CH$_3$), 1.41 (s, 3H, CH$_3$), 1.59 (s, 3H, CH$_3$), 1.83 (m, 2H, CH$_2$Et), 3.69 (dd, 1H, $^3J_{H-H}$=1.3 Hz, $^2J_{P-H}$=10.6 Hz, $^1$CH), 3.77 (qd, 1H, $^3J_{H-H}$=3.1 Hz, $^3J_{H-H}$=7.3 Hz, $^2J_{P-H}$=12.4 Hz, $^1$CH), 3.90 (qd, 1H, $^3J_{H-H}$=1.8 Hz, $^3J_{H-H}$=3.5 Hz, $^2J_{P-H}$=10.8 Hz, $^4$CH), 4.05 (ddd, 2H, $^3J_{H-H}$=4.3 Hz, $^2J_{H-H}$=13.4 Hz, $^2J_{P-H}$=51.8 Hz, $^6$CH$_2$), 4.36 (td, 1H, $^3J_{H-H}$=5.3 Hz, $^5$CH), 4.5 (dl, 1H, $^3J_{H-H}$=7.8 Hz, $^3$CH), 4.78 (ddd, 1H, $^3J_{P-H}$=22.7 Hz, $^3J_{H-H}$=3.5 Hz, $^3J_{H-H}$=7.6 Hz, $^2$CH).
MS FAB$^+$ (NBA): m/z (%) 337.18 [M+H$^{30}$] (90%), 338.18 [M+2H$^+$] (5%), 673.33 [2M+H$^+$] (5%).

4-(2,2-Dimethyl-[1,3]dioxolan-4-yl)-2,2-dimethyl-2-oxo-2-thienyl-tetrahydro-6λ*5*-[1,3]dioxolo[4,5-d][1,2]oxaphosphinan-3-ol (3.67)

This compound was prepared similarly to compound 3.3, starting from 2,3: 5,6-Di-O-isopropylidene-D-mannofuranose and ethyl 2-thienylhydrogenophosphinate 3.15.

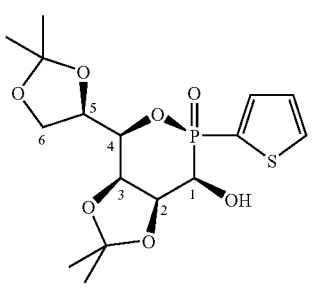

3.67

M(g/mol)=390.40
$C_{16}H_{23}O_7PS$
4 diastereomers
Yield$_{(overall)}$=49%
Dia I $^{31}$P RMN (161.97 MHz, CDCl$_3$): δ 25.5

$^1$H RMN (400.13 MHz, CDCl$_3$): δ 1.27 (s, 3H, CH$_3$), 1.31 (s, 3H, CH$_3$), 1.34 (s, 3H, CH$_3$), 1.46 (s, 3H, CH$_3$), 3.78 (dd, 1H, $^3J_{H-H}$=4.8 Hz, $^2J_{P-H}$=8.6 Hz, $^1$CH), 4.02 (q, 1H, $^3J_{H-H}$=6.3 Hz, $^2J_{P-H}$=8.4 Hz, $^4$CH), 4.23 (q, 1H, $^3J_{H-H}$=6.1 Hz, $^3J_{P-H}$=5.3 Hz, $^5$CH), 4.36 (dl, 1H, $^3J_{H-H}$=5.5 Hz, $^3$CH), 4.51 (m, 2H, $^6$CH$_2$), 4.67 (ddd, 1H, $^3J_{P-H}$=26.8 Hz, $^3J_{H-H}$=3.1 Hz, $^3J_{H-H}$=7.9 Hz, $^2$CH), 7.50-7.70 (m, 3H, CH$_{Ar}$), 7.31 (tl, 1H, CH$_{thi}$), 7.71 (q, 1H, CH$_{thi}$), 8.04 (t, 1H, CH$_{thi}$).
MS FAB$^+$ (NBA): m/z (%) 391.14 [M+H$^{+}$] (90%), 392.15 [M+2H$^+$] (5%).
Dia II $^{31}$P RMN (161.97 MHz, CDCl$_3$): δ 29.8
MS FAB$^+$ (NBA): m/z (%) 391.13 [M+H$^+$] (90%), 392.14 [M+2H$^+$] (5%).
Dia III $^{31}$P RMN (161.97 MHz, CDCl$_3$): δ 30.1
MS FAB$^+$ (NBA): m/z (%) 391.14 [M+H$^+$] (90%), 392.15 [M+2H$^+$] (5%).
Dia IV $^{31}$P RMN (161.97 MHz, CDCl$_3$): δ 32.3

4-(2,2-Dimethyl-[1,3]dioxolan-4-yl)-2,2-dimethyl-2-oxo-2-dimethoxymethyl-tetrahydro-6λ*5*-[1,3]dioxolo[4,5-d[1,2]oxaphosphinan-3-ol In a Schlenk tube that had been previously deoxygenated were introduced under nitrogen atmosphere 1.3 g of protected mannose (5.2 mmol), 0.8 g of methyl dimethoxyphosphinate (5.2 mmol, 1 eq.), 120 mg of potassium tert-butoxide (1 mmol, 0.2 eq.) and 10 ml of anhydrous THF. This medium was then stirred at room temperature for 15 hours.

To the medium were added 10 ml of a 0.1N hydrochloric acid solution, 10 ml of a sodium chloride saturated solution. The thus obtained aqueous phase was extracted three times with chloroform. The organic phases were then combined, dried on magnesium sulfate, filtered, and then evaporated under reduced pressure to produce a coloured oil. This residue was then purified using an automated flash chromatography (CH$_2$Cl$_2$/AcOEt eluent system using a gradient ranging from 100/0 to 0/100).

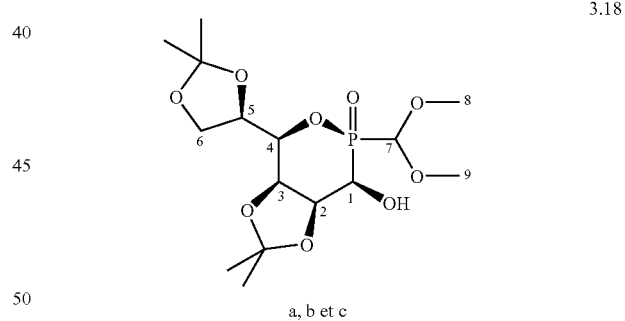

3.18 a, b et c

M (g/mol)=382.32
$C_{15}H_{31}O_8NP$
White solid
3 diastereomers 3.18a (45%),
3.18b (31%) and 3.18c (14%)
Overall yield=68%
Dia I (3.18a)
$^1$H NMR (400.13 MHz, CDCl$_3$): δ 1.34 (s, 3H, CH$_3$), 1.36 (s, 3H, CH$_3$), 1.39 (s, 3H, CH$_3$), 1.55 (s, 3H, CH$_3$), 3.55 (s, 6H, $^{8,9}$CH$_3$), 4.05 (m, 3H, $^6$CH$_2$+$^3$CH), 4.26 (ddd, 1H, $^3J_{H-H}$=1.5 Hz, $^3J_{H-H}$=2.6 Hz, $^2J_{P-H}$=7.9 Hz, $^1$CH), 4.32 (dd, 1H, $^3J_{H-H}$=3.5 Hz, $^2J_{P-H}$=5.9 Hz, $^5$CH), 4.54 (dd, 1H, $^3J_{H-H}$=1.6 Hz, $^3J_{P-H}$=7.9 Hz, $^4$CH), 4.66 (d, 1H, $^2J_{P-H}$=5.9 Hz, $^7$CH), 4.85 (ddd, 1H, $^3J_{H-H}$=3.4 Hz, $^3J_{H-H}$=7.9 Hz, $^3J_{P-H}$=23.7 Hz, $^2$CH).

MS HR+ (NBA): Theoretical mass 382.3548; Experimental mass 382.3553.

Dia II (3.18b)

$^1$H NMR (400.13 MHz, CDCl$_3$): δ 1.35 (s, 3H, CH$_3$), 1.39 (s, 3H, CH$_3$), 1.41 (s, 3H, CH$_3$), 1.47 (s, 3H, CH$_3$), 3.53 (s, 3H, $^8$CH), 3.56 (s, 3H, $^9$CH$_3$), 3.84 (dd, 1H, $^3J_{H-H}$=1.8 Hz, $^2J_{P-H}$=10.5 Hz, $^1$CH), 4.09 (m, 2H, $^6$CH$_2$), 4.32 (m, 1H, $^5$CH), 4.46 (AB, 1H, $^4$CH), 4.51 (ddd, $^3J_{H-H}$=1.1 Hz, $^3J_{H-H}$=1.5 Hz, $^2J_{P-H}$=7.3 Hz, $^3$CH), 4.74 (d, 1H, $^2J_{P-H}$=$^7$CH), 4.81 (ddd, 1H, $^3J_{H-H}$=4.2 Hz, $^3J_{H-H}$=7.2 Hz, $^2J_{P-H}$=26.3 Hz, $^2$CH).

Dia III $^1$H NMR (400.13 MHz, CDCl$_3$): δ 1.26 (s, 3H, CH$_3$), 1.29 (s, 3H, CH$_3$), 1.37 (s, 3H, CH$_3$), 1.53 (s, 3H, CH$_3$), 3.49 (s, 3H, $^8$CH$_3$), 3.57 (s, 3H, $^9$CH$_3$), 4.12 (m, 3H, $^1$CH+$^6$CH$_2$), 4.39 (AB, 1H, $^5$CH), 4.49 (ddd, 1H, $^3J_{H-H}$=1.1 Hz, $^3J_{H-H}$=9.0 Hz, $^2J_{P-H}$=12.0 Hz, $^4$CH), 4.81 (ddd, $^3J_{H-H}$=1.9 Hz, $^3J_{H-H}$=2.3 Hz, $^2J_{P-H}$=9.8 Hz, $^3$CH), 4.84 (ddd, 1H, $^3J_{H-H}$=2.8 Hz, $^3J_{H-H}$=7.3 Hz, $^2J_{P-H}$=26.2 Hz, $^2$CH), 5.08 (d, 1H,$^2J_{P-H}$=15.3 Hz, $^1$CH).

4-(2,2-Dimethyl-[1,3]dioxolan-4-yl)-2,2-dimethyl-2-oxo-2-diethoxymethyl-tetrahydro-6λ*5*-[1,3]dioxolo[4,5-d][1,2]oxaphosphinan-3-ol In a Schlenk tube that had been previously deoxygenated were introduced under nitrogen atmosphere 6.6 g of protected mannose (25.6 mmol), 5 g of ethyl diethoxyphosphinate (25.6 mmol, 1eq.), 0.6 g of potassium tert-butoxide (5.2 mmol, 0.2 eq.) and 50 ml of anhydrous THF. This medium was then stirred at room temperature for 15 hours.

To the medium were added 25 ml of a 0.1 N hydrochloric acid solution, 25 ml of a sodium chloride saturated solution. The thus obtained aqueous phase was extracted three times with chloroform. The organic phases were then combined, dried on magnesium sulfate, filtered, and then evaporated under reduced pressure to produce a coloured oil. This residue was then taken up in an ethyl acetate/n-hexane mixture, whereby causing the precipitation of major diastereomer. After filtration and evaporation of the filtrate, the residue obtained was purified on a silica gel column according to a DCM/AcOEt gradient ranging from 100/0 to 80/20.

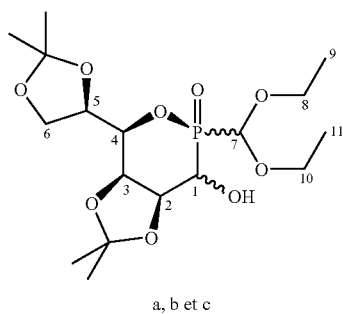

a, b et c

M (g/mol)=410.41
C$_{17}$H$_{32}$O$_9$P
White solid
2 diastereomers 3,19a (54%), 3,19b (22%), 3,19c (24%)
Overall yield=69%

Dia I (3,19a)

$^1$H NMR (400.13 MHz, CDCl$_3$): δ 1.25 (t, 3H, $^3J_{H-H}$=6.9 Hz, $^9$CH$_3$), 1.26 (t, 3H, $^3J_{H-H}$=7.1 Hz, $^{11}$CH$_3$), 1.33 (s, 3H, CH$_3$), 1.36 (s, 3H, CH$_3$), 1.37 (s, 3H, CH$_3$) 1.54 (s, $^3$H, CH$_3$), 3.78 (m, 4H, $^{8,10}$CH$_2$), 4.06 (m, 2H, $^6$CH$_2$), 4.13 (ddd, 1H, $^3J_{H-H}$=1.5 Hz, $^3J_{H-H}$=8.3 Hz, $^3$CH), 4.27 (ld, 1H, $^3J_{H-H}$=3.3 Hz, $^1$CH), 4.31 (ddd, 1H, $^3J_{H-H}$=4.1 Hz, $^3$H$_{H-H}$=5.8 Hz, $^3J_{P-H}$=9.8 Hz, $^5$CH), 4.53 (ld, 1H, $^3J_{H-H}$=8.1 Hz, $^4$CH), 4.78 (d, 1H, $^2J_{P-H}$=5.9 Hz, $^7$CH), 4.82 (ddd, 1H, $^3J_{H-H}$=3.3 Hz, $^3J_{H-H}$=5.4 Hz, $^3J_{P-H}$=23.5 Hz, $^2$CH).

MS HR+ (NBA): Theoretical mass 411.1784; Experimental mass 411.1790.

Dia II (3,19b)

$^1$H NMR (400.13 MHz, CDCl$_3$): δ 1.27 (t, 3H, $^3J_{H-H}$=7.1 Hz, $^9$CH$_3$), 1.28 (t, 3H, $^3J_{H-H}$=7.0 Hz, $^{11}$CH$_3$), 1.31 (s, 3H, CH$_3$), 1.34 (s, 3H, CH$_3$), 1.38 (s, 3H, CH$_3$), 1.52 (s, 1.52 (s, 3H, CH$_3$), 3.82 (m, 4H, $^{8,10}$CH$_2$), 4.11 (AB, 2H, $^6$CH$_2$), 4.30 (AB, 2H, $^1$CH+$^3$CH), 4.47 (dd, 1H), $^3J_{P-H}$=2.0 Hz, $^3J_{H-H}$=3.0 Hz, $^4$CH), 4.57 (Id, 1H, =7.8 Hz, $^5$CH), 4.81 (ddd, 1H, =3.0 Hz, $^3J_{H-H}$=7.8 Hz, $^3J_{P-H}$=24.0 Hz, $^2$CH), 4.91 (d, 1H, $^2J_{P-H}$=5.7 Hz, $^7$CH).

6-(1,2-dihydroxy-ethyl)-2-oxo-2-hydro-2λ*5*-[1,2]oxaphosphinane-3,4,5-triol

In a Schott tube were introduced 1 g of protected phosphinosugar (2.4 mmol), and 10 ml of a 1N hydrochloric acid solution. The tube, closed with a septum, was heated at 80° C. for 1-2 hours.

The reaction medium was then brought back to room temperature, then evaporated under vacuum (vane pump). After two coevaporations with ethanol, a powdered white solid was collected corresponding to the pure deprotected compound.

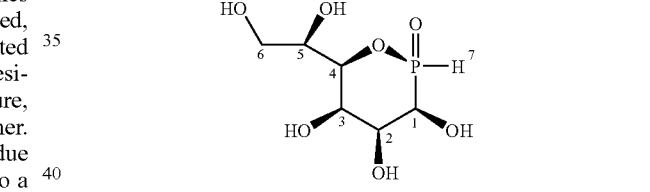

3.20

M (g/mol)=228.56
C$_6$H$_{13}$O$_7$P
White solid (0.55 g)
1 diastereomer 3.20
Yield=100%

$^1$H NMR (400.13 MHz, DMSO): δ 3.34-3.63 (m, 4H, $^6$CH$_2$, $^5$CH, $^3$CH), 3.74-3.94 (m, 2H, $^2$CH, $^4$CH), 3.96 (d, 1H, $^2J_{P-H}$=7.5. $^1$CH), 5.39 (sl, 1H, OH), 6.86 (dd, $^3J_{P-H}$=17.2 Hz, $_3J_{H-H}$=2.6 Hz, P—H).

MS HR+ (NBA): Theoretical mass 228.2182; Experimental mass 228.2191.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinin-3-tosyl In a Schlenk tube that had been previously deoxygenated and under nitrogen atmosphere were introduced 1.5 g of protected phosphinosugar 3.3a (3.6 mmol) and 5 mL of distilled pyridine (43 mmol, 12 eq.). The medium was then cooled to 0° C. prior to adding 5 g of freshly recrystallized tosyl chloride (0.036 mol, 10 eq.). After stirring at 0° C. for 1 hour, the medium was allowed to warm to room temperature and stirring was continued for 24 hours.

The reaction medium was taken up in chloroform. The organic phase was washed with a sodium hydrogenocarbonate saturated solution, dried, then evaporated under reduced pressure using a vane pump so as to remove the pyridine traces. The product was obtained in a pure form as a white solid.

3.5

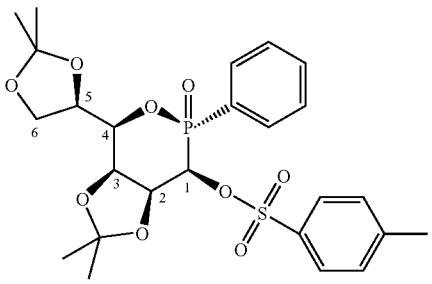

M (g/mol)=538.55
$C_{25}H_{31}O_9PS$
White solid (1.95 g)
1 diastereomer 3.5
Yield=95%
$^1$H NMR (400.13 MHz, CDCl$_3$): δ 1.29 (s, 3H, CH$_3$), 1.37 (s, 3H, CH$_3$), 1.44 (s, 3H, CH$_3$), 1.69 (s, 3H, CH$_3$), 2.38 (s, 3H, CH$_3$Tol), 4.02 (m, 2H, $^6$CH$_2$), 4.24 (d, 1H, $^3J_{H-H}$=7.1 Hz, $^4$CH), 4.43 (dd, 1H, $^3J_{H-H}$=8.6 Hz, $^3J_{H-H}$=4.2 Hz, $^5$CH), 4.71 (d, 1H, $^3J_{H-H}$=9.1 Hz, $^2$CH), 4.83 (d, 1H, $^2J_{P-H}$=8.3 Hz, $^1$CH), 5.01 (ddd, 1H, $^3J_{H-H}$=3.6 Hz, $^3J_{H-H}$=8.2 Hz, $^3$CH), 7.00-7.58 (m, 9H, CH$_{Ar}$).
MS HR$^+$ (NBA): Theoretical mass 538.1505; Experimental mass 538.1498.

6-(1,2-dihydroxy-ethyl)-2,2-dimethyl-2-oxo-2-diethoxymethyl-tetrahydro-6λ*5*-[1,3]dioxolo[4,5-d][1,2]oxaphosphinan-3-tosyl In a 50 ml flask were introduced 1 g of phosphinosugar (1.8 mmol), 1 g of Amberlyst 15 resin and 20 ml of methanol. This medium was mechanically stirred for 24 hours at room temperature.

The reaction medium was filtered on sintered glass, then evaporated under reduced pressure to produce a colourless oil. This oil did correspond to the expected product without further purification.

3.6

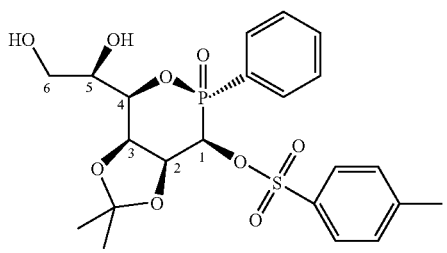

M (g/mol)=498.49
$C_{22}H_{27}O_9PS$
Colourless oil (0.65 g, 13.6 mol)
1 diastereomer 3.6
Yield=100%
$^1$H NMR (400.13 MHz, DMSO): δ 1.12 (s, 3H, CH$_3$), 1.44 (s, 3H, CH$_3$), 2.44 (s, 3H, CH$_3$Tol), 3.31 (dd, 1H, $^3J_{H-H}$=4.5 Hz, $^2J_{H-H}$=11.6 Hz, $^6$CH$_2$), 3.46 (dd, 1H, $^3J_{H-H}$=2.1 Hz, $^2J_{H-H}$=11.3 Hz, $^6$CH$_2$), 3.59 (qd, 1H, $^3J_{H-H}$=2.3 Hz, $^3J_{H-H}$=4.5 Hz, $^3J_{P-H}$=11.4 Hz, $^4$CH), 4.69 (dd, 1H, $^3J_{H-H}$=8.6 Hz, $^3J_{P-H}$=22.9 Hz, $^2$CH), 4.82 (ddd, 1H, $^3J_{H-H}$=8.1 Hz, $^2J_{P-H}$=23.0 Hz, $^1$CH), 5.17 (dd, 1H, $^3J_{H-H}$=4.0 Hz, $^3J_{H-H}$=2.1 Hz, $^3$CH), 7.04-7.47 (m, 9H, CH$_{Ar}$).
MS HR$^+$ (NBA): Theoretical mass 499.1192; Experimental mass 499.1182.

6-(1,2-dihydroxy-ethyl)-2-oxo-2-phenyl-2λ*5*-[1,2]oxaphosphinane-4,5-diol-3-tosyl In a Schott tube were introduced 1 g of tosylated phosphinosugar (1.8 mmol), and 10 ml of a 1N hydrochloric acid solution. The tube was closed by means of a septum and was heated at 80° C. for 12 hours.

The reaction medium was then brought back to room temperature, then evaporated using a vane pump. After two coevaporations with ethanol, a powdered white solid was collected corresponding to the pure deprotected compound.

3.7

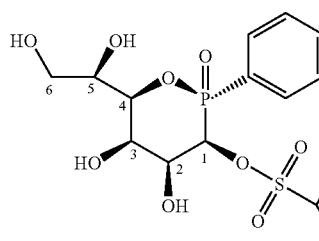

M (g/mol)=458.43
$C_{19}H_{23}O_9PS$
White solid
1 diastereomer 3.7
Yield=100%
$^1$H NMR (400.13 MHz, DMSO): δ 2.72 (s, 3H, CH$_3$Tol), 3.31 (dd, 1H, $^3J_{H-H}$=4.5 Hz, $^2J_{H-H}$=11.6 Hz, $^6$CH$_2$), 3.46 (dd, 1H, $^3J_{H-H}$=2.1 Hz, $^2J_{H-H}$=11.3 Hz, $^6$CH$_2$), 3.59 (qd, 1H, $^3J_{H-H}$=2.3 Hz, $^3J_{H-H}$=4.5 Hz, $^3J_{H-H}$=11.4 Hz, $^4$CH), 4.69 (dd, 1H, $^3J_{H-H}$=8.6 Hz, $^3J_{P-H}$=22.9 Hz, $^2$CH), 4.82 (ddd, 1H, $^3J_{H-H}$=3.8 Hz, $^3J_{H-H}$=8.1 Hz, $^2J_{P-H}$=23.0 Hz, $^1$CH), 5.17 (q, 1H, $^3J_{H-H}$=4.0 Hz, $^3J_{H-H}$=2.1 Hz, $^3$CH), 7.04-7.47 (m, 9H, CH$_{Ar}$).
MS HR$^+$(NBA): Theoretical mass 458.1992; Experimental mass 458.2003.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinin-3-mesyl In a Schlenk tube that had been previously deoxygenated and under nitrogen atmosphere were introduced 1 g of protected phosphinosugar 3.3a (2.4 mmol) and 3 of distilled pyridine (28 mmol, 12 eq.). The medium was then cooled to 0° C. prior to adding 2 ml of distilled mesyl chloride (0.024 mol, 10 eq.). The medium was stirred at 0° C. for 1 hour and then it was allowed to warm to room temperature. Stirring was continued for 24 hours.

The reaction medium was taken up in chloroform. This organic phase was then washed with a sodium hydrogenocarbonate saturated solution, dried, then evaporated under reduced pressure using a vane pump so as to remove the pyridine traces. The product was obtained in a pure form as a white solid.

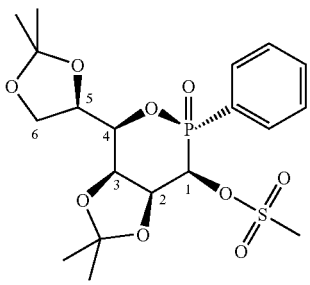

3.8

M (g/mol)=496.05
C$_{10}$H$_{27}$O$_9$PS
White solid (1.13 g)
1 diastereomer 3.8
Yield=100%
$^1$H NMR (400.13 MHz, CDCl$_3$): δ 1.29 (s, 3H, CH$_3$), 1.35 (s, 3H, CH$_3$), 1.38 (s, 3H, CH$_3$), 1.53 (s, 3H, CH$_3$), 2.91 (s, 3H, CH$_3$Ms), 3.85 (dd, 1H, $^3$J$_{H-H}$=8.8 Hz, $^3$J$_{H-H}$=4.5 Hz, $^5$CH), 3.90 (t, 1H, $^3$J$_{H-H}$=6.4 Hz, $^3$CH), 4.27 (dd, 1H, $^3$J$_{H-H}$=6.3 Hz, $^3$J$_{H-H}$11.6 Hz, $^4$CH), 4.68 (dd, 2H, $^3$J$_{H-H}$=8.1 Hz, $^2$J$_{H-H}$=36.1 Hz, $^6$CH$_2$), 5.05 (ddd, 1H, $^3$J$_{H-H}$=3.6 Hz, $^3$J$_{H-H}$=8.2 Hz, $^3$J$_{P-H}$=22.9 Hz, $^2$CH), 5.67 (d, 1H, $^2$J$_{P-H}$=8.0 Hz, $^1$CH), 7.59-7.68 (m, 5H, CH$_{Ar}$).
MS HR$^+$ (NBA): Theoretical mass 463.1192; Experimental mass 463.1175.

4-(2,2-Dimethyl-[1,3]dioxolan-4-yl)-2,2-dimethyl-2-oxo-2-diethoxymethyl-tetrahydro-6λ*5*-[1,3]dioxolo[4,5-d][1,2]oxaphosphinan-3-tosyl In a Schlenk tube that had been previously deoxygenated and under nitrogen atmosphere were introduced 0.5 g of protected phosphinosugar 3.19a (1.2 mmol) and 3 ml of distilled pyridine (0.007 mol, 6 eq.). The medium was then cooled to 0° C. prior to adding 1.2 g of freshly recrystallized tosyl chloride (0.006 mol, 5 eq.). After stirring at 0° C. for 1 hour, the medium was allowed to warm to room temperature. Stirring was continued for 24 hours.

The reaction medium was taken up in chloroform. The organic phase was then washed with a sodium hydrogenocarbonate saturated solution, then evaporated under reduced pressure using a vane pump so as to remove the pyridine traces. The oily residue obtained was then purified on a silica gel column (diethyl ether/ethyl acetate)

3.21

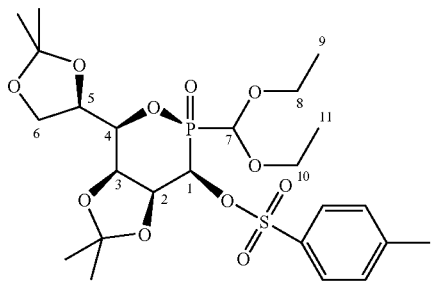

M (g/mol)=564.23
C$_{24}$H$_{37}$O$_{11}$PS
White solid (0.62 g)
1 diastereomer 3.21
Yield=98%
$^1$H NMR (400.13 MHz, CDCl$_3$): δ 1.17 (t, 3H, $^3$J$_{H-H}$=7.0 Hz, $^9$CH$_3$), 1.19 (t, 3H, $^3$J$_{H-H}$=7.0 Hz, $^{11}$CH$_3$), 1.23 (s, 3H, CH$_3$), 1.28 (s, 3H, CH$_3$), 1.34 (s, 3H, CH$_3$), 1.48 (s, 3H, CH$_3$), 2.38 (s, 3H, CH$_3$Tol), 3.49-3.77 (m, 4H, $^{8,10}$CH$_2$), 4.03 (ABX, 2H, $^6$CH$_2$), 4.16 (qd, 1H, $^3$J$_{H-H}$=1.6 Hz, $^3$J$_{H-H}$=3.0 Hz, $^3$J$_{P-H}$=8.4 Hz, $^4$CH), 4.26 (m, 1H, $^3$CH), 4.47 (dl, 1H, $^3$J$_{H-H}$=8.2 Hz, $^5$CH), 4.66 (d, 1H, $^2$J$_{P-H}$=9.9 Hz, $^1$CH), 4.82 (ddd, 1H, $^3$J$_{H-H}$=2.6 Hz, $^3$J$_{H-H}$=7.5 Hz, $^3$J$_{P-H}$=20.4 Hz, $^2$CH), 5.30 (d, 1H, $^2$J$_{P-H}$=2.7 Hz, $^7$CH), 5.28 (2s, 2H, CH$_{Ar}$Tol), 7.82 (2s, 2H, CH$_{Ar}$Tol).
MS HR$^+$ (NBA): Theoretical mass 565.1872; Experimental mass 565.1869.

6-(1,2-dihydroxy-ethyl)-2-oxo-2-hydrogeno-2A*5*-[1,2]oxaphosphinane-4,5-diol-3-tosyl In a Schott tube were introduced 1 g of protected tosylated phosphinosugar (1.8 mmol) and 10 ml of a 1N hydrochloric acid solution. The tube was closed by means of a septum and was heated at 80° C. for 2 hours.

The reaction medium was then brought back to room temperature, then evaporated using a vane pump. After two coevaporations with ethanol, a powdered white solid was collected corresponding to the pure deprotected compound.

3.22

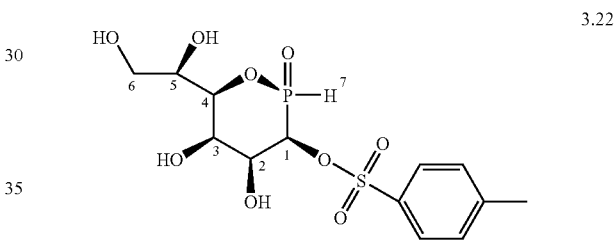

M (g/mol)=382.33
C$_{13}$H$_{19}$O$_9$PS
White solid (0.65 g)
1 diastereomer 3.22
Yield=100%
$^1$H NMR (400.13 MHz, DMSO): δ 2.35 (s, 3H, CH$_3$Tol), 3.40 (dd, 1H, $^3$J$_{H-H}$=5.8 Hz, $^3$J$_{P-H}$=11.4 Hz, $^5$CH), 3.62 (dd, 1H, $^3$J$_{H-H}$=2.8 Hz, $^3$J$_{P-H}$=11.4 Hz, $^4$C), 3.75 (m, 2H, $^6$CH$_2$), 4.02 (dd, 1H, $^3$J$_{P-H}$=7.6 Hz, $^3$J$_{H-H}$=1.3 Hz, $^1$CH), 4.11 (dd, 1H, $^3$J$_{P-H}$=3.8 Hz, $^3$CH), 4.57 (ddd, 1H, $^3$J$_{H-H}$=5.4 Hz, $^3$J$_{H-H}$=7.8 Hz, $^3$J$_{P-H}$=16.9 Hz, $^2$CH), 7.01 (d, 1H, $^1$J$_{P-H}$=558.0 Hz, P—H), 7.21 (d, 2H, CH$_{Ar}$Tol), 7.53 (d, 2H, CH$_{Ar}$Tol).
MS HR$^+$ (NBA): Theoretical mass 383.1245; Experimental mass 383.1315.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-imidate In a Schlenk tube that had been previously deoxygenated and under nitrogen atmosphere, were introduced 1 g of protected phosphinosugar 3.3a (2.6 mmol), 10 ml of dichloromethane and 2.6 ml of trichloroacetonitrile (25.9 mmol, 9.5 eq.). 75 mg of sodium hydride (3.1 mmol, 1.2 eq.) were then added and the medium was stirred for 15 hours at room temperature.

The reaction medium was then filtered on Celite. The obtained filtrate was evaporated under reduced pressure to produce a slightly coloured oil.

This oil was purified on a silica gel column. The eluent used was a hexane/ethyl acetate system.

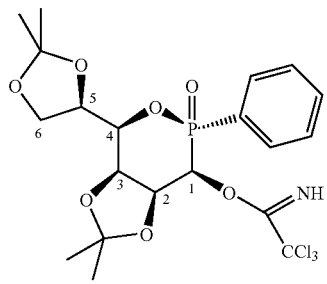

3.57

M (g/mol)=425.42
C$_{20}$H$_{28}$NO$_7$PCl$_3$
Yield=81%
Yellow solid
1 diastereomer 3.57

$^1$H NMR (400.13 MHz, CDCl$_3$): δ 1.21 (s, 3H, CH$_3$), 1.24 (s, 3H, CH$_3$), 1.28 (s, 3H, CH$_3$), 1.42 (s, 3H, CH$_3$), 3.29 (sl, 1H, NH), 3.78 (dd, 1H, $^3J_{H-H}$=5.3 Hz, $^3J_{H-H}$=86. Hz, $^4$CH), 3.96 (m, 2H, $^6$CH$_2$), 4.18 (q, 1H, $^3J_{H-H}$=5.8 Hz, $^3J_{P-H}$=5.8 Hz, $^1$CH), 4.38 (m, 1H, $^5$CH), 4.46 (d, 1H, $^3J_{H-H}$=8,5 Hz, $^3$CH), 4.58 (ddd, 1H, $^3J_{H-H}$=3.3 Hz, $^3J_{H-H}$=8.1 Hz, $^3J_{P-H}$=25.3 Hz, $^2$CH), 7.45-7.78 (m, 5H, CH$_{Ar}$).

MS HR$^+$ (NBA): Theoretical mass 425.4221; Experimental mass 425.4229.

4-(2,2-Dimethyl-[1,3]dioxolan-4-yl)-2,2-dimethyl-2-oxo-2-diethoxymethyl-tetrahydro-6λ*5*-[1,3]dioxolo[4,5-d][1,2]oxaphosphinan-3-imidate In a Schlenk tube that had been previously deoxygenated and under nitrogen atmosphere, were introduced 1 g of protected phosphinosugar 3.19a (2.6 mmol), 10 ml of dichloromethane and 2.6 ml of trichloroacetonitrile (26 mmol, 10 eq.). 75 mg of sodium hydride (3.2 mmol, 1.2 eq.) were then added and the medium was stirred for 15 hours at room temperature.

The reaction medium was then filtered on Celite. The obtained filtrate was evaporated under reduced pressure to produce a slightly coloured oil.

This oil was purified on a silica gel column. The eluent used was a hexane/ethyl acetate system of from 100/0 to 0/100.

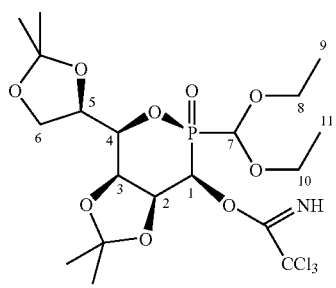

3.58

M (g/mol)=554.79
C$_{19}$H$_{31}$NPO$_9$Cl$_3$
Yield=62% (835 mg)
Colourless oil
1 diastereomer 3.58

$^1$H NMR (400.13 MHz, CDCl$_3$): δ 1.23 (t, 3H, $^9$CH$_3$), 1.26 (t, 3H, $^{11}$CH$_3$), 1.38 (s, 3H, CH$_3$), 1.40 (s, 3H, CH$_3$), 1.52 (s, 3H, CH$_3$), 1.63 (s, 3H, CH$_3$), 3.73 (m, 4H, $^{8\ 10}$CH$_2$), 4.12 (m, 3H, $^6$CH$_2$+$^5$CH), 4.31 (m, 1H, $^1$CH), 4.53 (d, 1H, $^3J_{H-H}$=7.4 Hz, $^4$CH), 4.81 (d, 1H, $^2J_{P-H}$=7.8 Hz, $^7$CH), 4.91 (ddd, 1H, $^3J_{H-H}$=2.7 Hz, $^3J_{H-H}$=7.4 Hz, $^3J_{H-H}$=21.1 Hz, $^2$CH), 5.67 (d, 1H, $^3J_{H-H}$=2.7 Hz, $^3$CH), 8.61 (sl, 1H, NH).

MS HR$^+$ m(NBA): Theoretical mass 554.7934; Experimental mass 554.8015.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-aminobenzyl In a Schlenk tube that had been previously deoxygenated and under nitrogen atmosphere were introduced 1 g of protected compound 3.24 (3 mmol), 10 ml of THF, 0.35 ml of methyl phenyl hydrogenophosphinate (3 mmol, 1 eq.) and potassium tert-butoxide (70 mg, 0.2 eq.). The medium was thus stirred at room temperature for 15 hours.

15 ml of 0.1N hydrochloric acid were then added to the reaction medium, then 15 ml of a sodium chloride saturated solution and 50 ml of chloroform. The aqueous phase was extracted with 2×50 ml of chloroform. The organic phases were combined, dried on magnesium sulfate and evaporated under reduced pressure. The thus obtained oily residue was then purified on a silica gel column using diethyl ether.

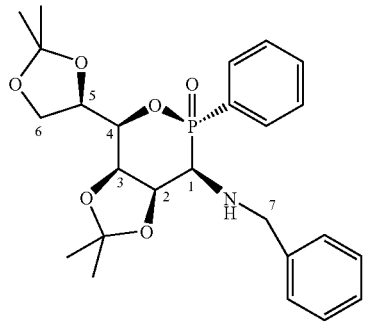

3.28

M (g/mol)=473.51
C$_{25}$H$_{32}$NO$_6$P
Colourless oil
1 diasporameter 3.28
Overall yield=73%

$^1$H NMR (400.13 MHz, CDCl$_3$): δ 1.35 (s, 3H, CH$_3$), 1.37 (s, 3H, CH$_3$), 1.40 (s, 3H, CH$_3$), 1.45 (s, 3H, CH$_3$), 3.35 (dd, 1H, $^3J_{H-H}$=4.3 Hz, $^2J_{P-H}$=7.6 Hz, $^1$CH), 3.94 (sl, 2H, $^7$CH$_2$), 4.14 (m, 2H, $^6$CH$_2$), 4.43 (m, 1H, $^3$CH), 4.49 (qd, 1H, $^3J_{H-H}$=1.8 Hz, $^3J_{H-H}$=7.6 Hz, $^4$CH), 4.58 (m, 1H, $^5$CH), 4.69 (ddd, 1H, $^3J_{P-H}$=21.2 Hz, $^3J_{H-H}$=4.3 Hz, $^3J_{H-H}$=6.6 Hz, $^2$CH), 7.23-7.97 (m, 5H, CH$_{Ar}$).

MS HR$^+$ (NBA): Theoretical mass 474.2046; Experimental mass 474.2058.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-aminophenyl In a Schlenk tube that had been previously deoxygenated and under nitrogen atmosphere were introduced 1 g of protected compound 3.25 (3 mmol), 10 ml of THF, 0.35 ml of methyl phenyl hydrogenophosphinate (3 mmol, 1 eq.) and potassium tert-butoxide (70 mg, 0.2 eq.). The medium was thus stirred at room temperature for 15 hours.

15 ml of 0.1N hydrochloric acid were then added to the reaction medium, as well as 15 mL of a sodium chloride saturated solution and 50 ml of chloroform. The aqueous phase was extracted again with 2×50 ml of chloroform. The organic phases were combined, dried on magnesium sulfate and evaporated under reduced pressure. The thus obtained oily residue was then purified on a silica gel column in a diethyl ether/hexane system.

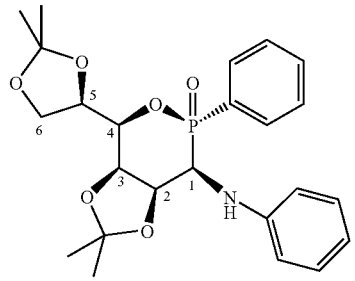

3.29 a et b

M (g/mol)=459.48
$C_{24}H_{30}NO_6P$
2 diastereomers 3.29a and b
de=80%
Overall yield=58%
Dia I Yield=90% White solid
$^1$H NMR (400.13 MHz, CDCl$_3$): δ 1.30 (s, 3H, CH$_3$), 1.33 (s, 3H, CH$_3$), 1.34 (s, 3H, CH$_3$), 1.52 (s, 3H, CH$_3$), 3.97 (dd, 1H, $^3J_{H-H}$=3.2 Hz, $^3J_{P-H}$=7.2 Hz, $^1$CH), 4.05 (m, 2H, $^6$CH$_2$), 4.40 (m, 2H, $^4$CH+$^5$CH), 4.46 (dl, 1H, $^3J_{H-H}$=7.1 Hz, $^3$CH), 4.77 (qd, 1H, $^2J_{P-H}$=23.0 Hz, $^3J_{H-H}$=3.3 Hz, $^3J_{H-H}$=7.2 Hz, $^2$CH), 6.69-6.73 (m, 5H, CH$_{ANI}$), 7.10-7.37 (m, 5H, CH$_{Ar}$).
MS HR$^+$ (NBA): Theoretical mass 459.1811; Experimental mass 459.1792.

Dia II Yield=10% White solid
$^1$H NMR (400.13 MHz, CDCl$_3$): δ 1.31 (s, 3H, CH$_3$), 1.35 (s, 3H, CH$_3$), 1.36 (s, 3H, CH$_3$), 1.60 (s, 3H, CH$_3$), 4.02 (dd, 1H, $^3J_{H-H}$=2.9 Hz, $^3J_{P-H}$=12.1 Hz, $^1$CH), 4.19 (ABX, 2H, $^6$CH$_2$), 4.39 (m, 2H, $^4$CH+$^5$CH), 4.53 (td, 1H, $^3J_{H-H}$=6.2 Hz, $^3$CH), 4.72 (qd, 1H, $^2J_{P-H}$=20.1 Hz, $^3J_{H-H}$=2.9 Hz, $^3J_{H-H}$=7.4 Hz, $^2$CH), 6.40-6.71 (m, 5H, CH$_{ANI}$), 7.04-7.36 (m, 5H, CH$_{Ar}$).
MS HR$^+$ (NBA): Theoretical mass 459.1811; Experimental mass 459.1791.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-aminotoluyl In a Schlenk tube that had been previously deoxygenated and under nitrogen atmosphere were introduced 1 g of protected compound 3.26 (3 mmol), 10 ml of THF, 0.35 ml of methyl phenyl hydrogenophosphinate (3 mmol, 1 eq.) and potassium tert-butoxide (70 mg, 0.2 eq.). The medium was thus stirred at room temperature for 15 hours.

15 ml of 0.1N hydrochloric acid were then added to the reaction medium, then 15 ml of a sodium chloride saturated solution and 50 ml of chloroform. The aqueous phase was extracted again with 2×50 ml of chloroform. The organic phases were combined, dried on magnesium sulfate, filtered and evaporated under reduced pressure. The thus obtained oily residue was then purified on a silica gel column using diethyl ether.

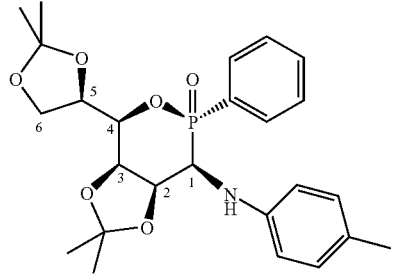

3.30 a et b

M (g/mol)=473.51
$C_{25}H_{32}NO_6P$
2 diastereomers 3.30 a and b
de=82%
Yield$_{global}$=51%
Dia I Yield=91% Colourless oil
$^1$H NMR (400.13 MHz, CDCl$_3$): δ 1.41 (s, 3H, CH$_3$), 1.45 (s, 3H, CH$_3$), 1.48 (s, 3H, CH$_3$), 1.62 (s, 3H, CH$_3$), 2.27 (s, 3H, CH$_3$Tol), 4.04 (dd, 1H, $^3J_{H-H}$=3.1 Hz, $^2J_{P-H}$=10.8 Hz, $^1$CH), 4.17 (m, 2H, $^6$CH$_2$), 4.49 (m, 2H, $^4$CH+$^5$CH), 4.56 (dl, 1H, $^3J_{H-H}$=4.6 Hz, $^3$CH), 4.90 (ddd, 1H, $^3J_{P-H}$=23.0 Hz, $^3J_{H-H}$=3.1 Hz, $^3J_{H-H}$=7.0 Hz, $^2$CH), 6.67 (d, 2H, $^3J_{H-H}$=8.4 Hz, CH$_{Tol}$), 7.03 (d, 2H, $^3J_{H-H}$=8.3 Hz, CH$_{Tol}$), 7.50-7.70 (m, 3H, CH$_{Ar}$), 7.95-8.05 (m, 2H, CH$_{Ar}$).
MS HR$^+$ (NBA): Theoretical mass 474.2046; Experimental mass 474.2055.

Dia II Yield=9% White solid
$^1$H NMR (400.13 MHz, CDCl$_3$): δ 1.36 (s, 3H, CH$_3$), 1.42 (s, 3H, CH$_3$), 1.49 (s, 3H, CH$_3$), 1.70 (s, 3H, CH$_3$), 2.23 (s, 3H, CH$_{3Tol}$), 4.07 (dd, 1H, $^3J_{H-H}$=2.9 Hz, $^2J_{P-H}$=14.3 Hz, $^1$CH), 4.27 (ABX, 2H, $^6$CH$_2$), 4.56 (m, 2H, $^4$CH+$^5$CH), 4.65 (dt, 1H, $^3J_{H-H}$=6.4 Hz, $^3$CH), 4.83 (qd, 1H, $^3J_{P-H}$=30.1 Hz, $^3J_{H-H}$=2.9 Hz, $^3J_{H-H}$=7.4 Hz, $^2$CH), 6.68 (d, 2H, $^3J_{H-H}$=8.4 Hz, CH$_{Tol}$), 7.04 (d, 2H, $^3J_{H-H}$=8.3 Hz, CH$_{Tol}$), 7.48-7.52 (m, 3H, CH$_{Ar}$), 7.95-8.05 (m, 2H, CH$_{Ar}$).
MS HR$^+$ (NBA): Theoretical mass 474.1875; Experimental mass 474.1886.

4-(2,2-Dimethyl-[1,3]dioxolan-4-yl)-2,2-dimethyl-2-oxo-2-thienyl-tetrahydro-6λ*5*-[1,3]dioxolo[4,5-d][1,2]oxaphosphinan-3-aminotoluyl This compound was obtained similarly to compound 3.30, starting from 2,3:5,6-Di-O-isopropylidene-N-p-tolyl-D-mannosylamine 3.26 and ethyl 2-thienylhydrogenophosphinate 3.15.

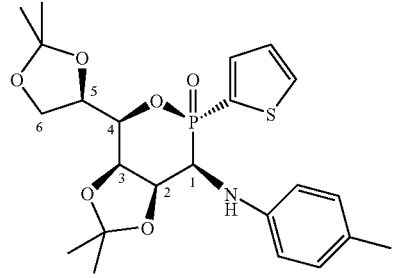

3.71

M(g/mol)=479.54
$C_{23}H_{30}NO_6PS$
2 diastereomers

Yield$_{(overall)}$=51%
Dia I $^{31}$P RMN (161.97 MHz, CDCl$_3$): δ 29.6
Dia II $^{31}$P RMN (161.97 MHz, CDCl$_3$): δ 26.3

6-(1,2-Dihydroxy-ethyl)-2-oxo-2-thienyl-2λ*5*-[1,2]oxaphosphinane-4,5-diol-3-aminotolyl (3.76)

This compound was obtained by deprotection of compound 3.71, similarly to deprotected compounds 3.20 or 3.31.

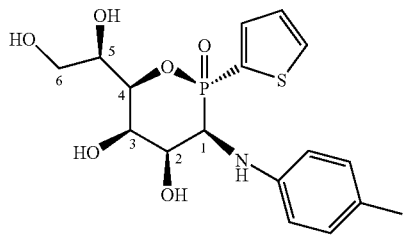 [SMILES: Cc1ccc(N[C@H]2[C@@H](O)[C@@H](O)[C@@H]([C@H](O)CO)O[P@@]2(=O)c2cccs2)cc1]

M(g/mol)=399.41
C$_{17}$H$_{22}$NO$_6$PS
Yield$_{(overall)}$=88%
$^{31}$P RMN (161.97 MHz, CDCl$_3$): δ 29.2

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-aminonaphthyl This compound was obtained similarly to compounds 3.28 to 3.30, starting from sugar 3.27 (2,3:5,6-di-O-isopropylidene-N-naphtyl-D-mannosylamine) and methyl phenylhydrogenophosphinate.

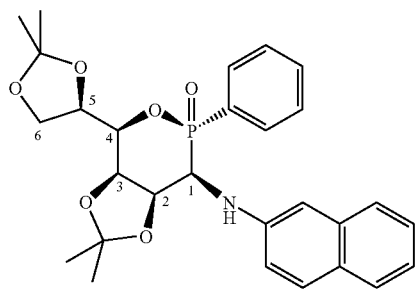

3.64

M(g/mol)=509.54
C$_{28}$H$_{32}$NO$_6$P
2 diastereomers
Yield$_{global}$=56%
Dia I $^{31}$P RMN (161.97 MHz, CDCl$_3$): δ 36.5
$^{1}$H RMN (400.13 MHz, CDCl$_3$): δ 1.31 (s, 3H, CH$_3$), 1.36 (s, 3H, CH$_3$), 1.41 (s, 3H, CH$_3$), 1.51 (s, 3H, CH$_3$), 3.71 (dd, 1H, $^{3}J_{H-H}$=10.8 Hz, $^{2}J_{P-H}$=13.7 Hz, $^{1}$CH), 4.11 (m, 2H, $^{6}$CH$_2$), 4.45 (m, 2H, $^{4}$CH+$^{5}$CH), 4.88 (ddd, 1H, $^{3}J_{P-H}$=22.8 Hz, $^{3}J_{H-H}$=3.3 Hz, $^{3}J_{H-H}$=7.1 Hz, $^{2}$CH), 5.12 (dd, 2H, $^{3}J_{H-H}$=3.1 Hz, $^{3}J_{H-H}$=12.7 Hz, $^{3}$CH), 6.81-7.94 (m, 12H, CH$_{Ar}$).
MS Q-TOF: m/z (%) 510.25 [M+H$^+$] (85%), 511.26 [M+2H$^+$] (10%).
Dia II $^{31}$P RMN (161.97 MHz, CDCl$_3$): δ 33.3

6-(1,2-dihydroxy-ethyl)-2-oxo-2-phenyl-2λ*5*-[1,2]oxaphosphinane-4,5-diol-3-aminotolyl In a Schott tube were introduced 1 g of protected phosphinosugar 3.30a (0.0021 mol), and 10 ml of a 1N hydrochloric acid solution. The tube was closed by means of a septum and was heated at 80° C. for 1 hour.

The reaction medium was then brought back to room temperature, then evaporated using a vane pump under high vacuum. After two coevaporations with ethanol a powdered white solid was collected corresponding to the pure deprotected compound.

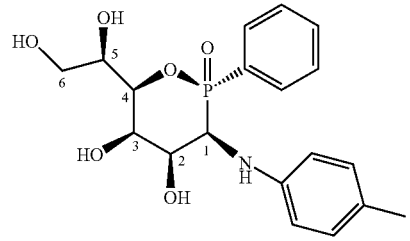

3.31

M (g/mol)=393.38
C$_{19}$H$_{24}$NO$_6$P
1 diastereomer 3.31
Yield=71%
$^{1}$H NMR (400.13 MHz, CDCl$_3$): δ 2.03 (s, 3H, CH$_3$Tol), 3.55 (sl, 1H, NH), 4.05-4.19 (m, 3H, $^{1}$CH+$^{4}$CH+$^{2}$CH), 4.81 (ABX, 2H, $^{6}$CH$_2$), 5.30 (AB, 1H, $^{3}$CH), 6.33 (d, 2H, $^{3}J_{H-H}$=7.9 Hz, CH$_{Tol}$), 6.64 (d, 2H, $^{3}J_{H-H}$=7.6 Hz, CH$_{Tol}$), 7.47-7.83 (m, 5H, CH$_{Ar}$).
MS HR$^+$ (NBA): Theoretical mass 394.1420; Experimental mass 394.1422.
$^{31}$P RMN (161.97 MHz, CDCl$_3$): δ 33.6

4-(2,2-Dimethyl-[1,3]dioxolan-4-yl)-2,2-dimethyl-2-oxo-2-phenylpropyl-tetrahydro-6λ*5*-[1,3]dioxolo[4,5-d][1,2]oxaphosphinan-3-aminotoluyl This compound was obtained similarly to compound 3.30 starting from 2,3:5,6-Di-O-isopropylidene-N-p-tolyl-D-mannosylamine 3.26 and ethyl phenylpropylhydrogenophosphinate 3.23.

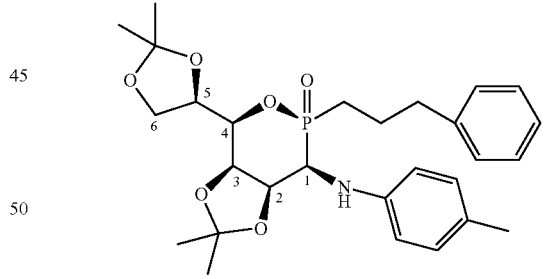

M(g/mol)=515.59
C$_{28}$H$_{38}$NO$_6$P
3 diastereomers
Yield$_{(overall)}$=57%
Dia I $^{31}$P RMN (161.97 MHz, CDCl$_3$): δ 30.8
Dia II $^{31}$P RMN (161.97 MHz, CDCl$_3$): δ 32.3
Dia III $^{31}$P RMN (161.97 MHz, CDCl$_3$): δ 38.6

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinin-3-amino In a Schlenk tube that had been previously deoxygenated and under nitrogen atmosphere were introduced 1 g of phosphinosugar 3.28 (0.002 mol), 10 ml of ethanol, and 1 g of palladium tetrakis(triphenylphosphine). The medium was thus stirred at room temperature for 24 hours under hydrogen atmosphere.

The reaction medium was then filtered on Celite so as to remove palladium. The obtained filtrate was evaporated under reduced pressure to produce a slightly coloured oil.

This oil was purified on a silica gel column, the expected product being only produced when using ethanol as eluent.

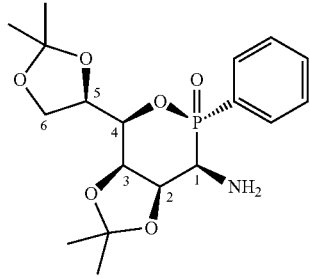

3.32

M (g/mol)=383.38
$C_{18}H_{26}NO_6P$
1 diasporameter 3.32
Colourless oil
Yield=87%
$^1$H NMR (400.13 MHz, CDCl$_3$): δ 1.38 (s, 3H, CH$_3$), 1.41 (s, 3H, CH$_3$), 1.44 (s, 3H, CH$_3$), 1.50 (s, 3H, CH$_3$), 1.86 (sl, 2H, NH$_2$), 3.49 (dd, 1H, $^2J_{P-H}$=5.2 Hz, $^3J_{H-H}$=6.4 Hz, $^1$CH), 4.11 (m, 2H, $^6$CH$_2$), 4.39-4.58 (m, 4H, $^3$CH+$^5$CH+$^2$CH+$^4$CH), 7.39-7.87 (m, 5H, CH$_{Ar}$).
MS HR$^+$ (NBA): Theoretical mass 384.1576; Experimental mass 384.1567.

6-(1,2-dihydroxy-ethyl)-2-oxo-2-phenyl-2λ*5*-[1,2]oxaphosphinane-4,5-diol-3-amino In a Schott tube were introduced 1 g of protected amine phosphinosugar 3.32 (0.0024 mol), and 20 ml of a 1N hydrochloric acid solution. The tube was closed by means of a septum and was heated at 80° C. for 2 hours.

The reaction medium was then brought back to room temperature, then evaporated using a vane pump under high vacuum. After two coevaporations with ethanol a yellow powdered solid was collected, corresponding to the pure deprotected amine compound.

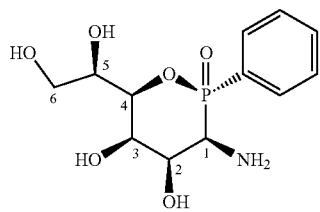

3.33

M (g/mol)=303.25
$C_{12}H_{18}NO_6P$
1 diasporameter 3.33
Yield=96%
Yellow solid $^1$H NMR (400.13 MHz, DMSO): δ 3.25 (dd, 1H, $^3J_{H-H}$=4.8 Hz, $^3J_{P-H}$=11.3 Hz, $^4$CH), 3.42 (AB, 1H, $^5$CH), 3.59 (dd, 1H, $^3J_{H-H}$=8.8 Hz, $^2J_{P-H}$=22.7 Hz, $^1$CH), 3.96 (AB, 1H, $^2$CH), 4.14-4.28 (m, 3H, $^6$CH$_2$+$^3$CH), 7.04-7.63 (m, 5H, CH$_{Ar}$).
MS HR$^+$ (NBA): Theoretical mass 303.3288; Experimental mass 303.3294

4-(2,2-Dimethyl-[1,3]dioxolan-4-yl)-2,2-dimethyl-2-oxo-2-diethoxymethyl-tetrahydro-6λ*5*-[1,3]dioxolo[4,5-d][1,2]oxaphosphinan-3-aminophenyl In a Schlenk tube that had been previously deoxygenated and under nitrogen atmosphere were introduced 1 g of protected mannose 3.25 (3 mmol), 0.6 g of ethyl diethoxyphosphinate (3 mmol, 1 eq.), 70 mg of potassium tert-butoxide (0.6 mmol, 0.2 eq.) and 10 ml of anhydrous THF. This medium was then stirred at room temperature for 15 hours.

To the medium were added 15 ml of a 0.1N hydrochloric acid solution, 15 ml of a sodium chloride saturated solution. The thus obtained aqueous phase was extracted three times with chloroform. The organic phases were then combined, dryed on magnesium sulfate and then evaporated under reduced pressure to produce a coloured oil. This residue was then purified on a silica gel column. The employed eluent system was DCM/AcOEt according to a gradient ranging from 100/0 to 80/20.

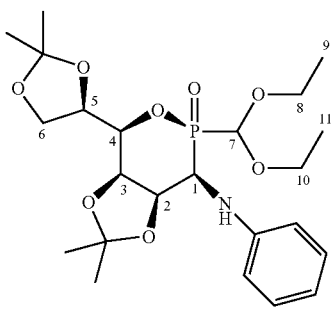

3.35 a et b

M (g/mol)=486.52
$C_{23}H_{35}O_8NP$
White solid
2 diastereomers 3.35 a and b
de=81%
Overall yield=46%
Dia I Yield=90%
$^1$H NMR (400.13 MHz, CDCl$_3$): δ 1.22 (t, 3H, $^9$CH$_3$), 1.25 (t, 3H, $^{10}$CH$_3$), 1.34 (s, 3H, CH$_3$), 1.39 (s, 3H, CH$_3$), 1.41 (s, 3H, CH$_3$), 1.43 (s, 3H, CH$_3$), 3.83 (ABX, 4H, $^{8,10}$CH$_2$), 4.13 (dd, 1H, $^3J_{H-H}$=3.6 Hz, $^2J_{P-H}$=10.6 Hz, $^1$CH), 4.15 (d, 2H, $^3J_{H-H}$=1.8 Hz, $^6$CH$_2$), 4.35 (ddd, 1H, $^3J_{H-H}$=7.8 Hz, $^3J_{H-H}$=6.2 Hz, $^3J_{P-H}$=1.5 Hz, $^4$CH), 4.41 (dt, 1H, $^3J_{H-H}$=8.0 Hz, $^3J_{H-H}$=4.9 Hz, $^3J_{P-H}$=5.1 Hz, $^5$CH), 4.44 (dt, 1H, $^3J_{H-H}$=1.6 Hz, $^3J_{P-H}$=7.0 Hz, $^4J_{P-H}$=6.4 Hz, $^3$CH), 4.84 (ddd, 1H, $^3J_{H-H}$=3.7 Hz, $^3J_{H-H}$=7.0 Hz, $^3J_{P-H}$=23.2 Hz, $^2$CH), 4.95 (d, 1H, $^2J_{P-H}$=10.0 Hz, $^7$CH), 6.78-7.01 (m, 3H, CH$_{Ar}$), 7.21-7.47 (m, 2H, CH$_{Ar}$).
MS HR$^+$ (NBA): Theoretical mass 485.2179; Experimental mass 485.2184.

4-(2,2-Dimethyl-[1,3]dioxolan-4-yl)-2,2-dimethyl-2-oxo-2-diethoxymethyl-tetrahydro-6λ*5*-[1,3]dioxolo[4,5-d][1,2]oxaphosphinan-3-aminotoluyl In a Schlenk tube that had been previously deoxygenated and under nitrogen atmosphere were introduced 2 g of protected mannose 3.26 (5.7 mmol), 1.2 g of ethyl diethoxyphosphinate (5.7 mmol, 1 eq.), 130 mg of potassium tert-butoxide (1.1 mmol, 0.2 eq.) and 15 ml of anhydrous THF. This medium was then stirred at room temperature for 15 hours.

To the medium were added 15 ml of a 0.1N hydrochloric acid solution, 15 ml of a sodium chloride saturated solution. The thus obtained aqueous phase was extracted three times with chloroform. The organic phases were then combined, dried on magnesium sulfate and then evaporated under reduced pressure to produce a coloured oil. This residue was then purified on a silica gel column. The employed eluent system was DCM/AcOEt according to a gradient ranging from 100/0 to 80/20.

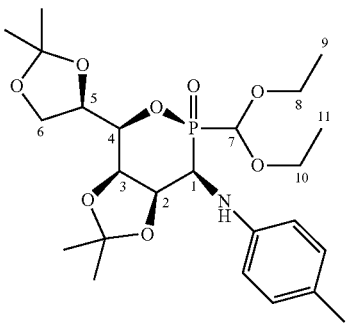

3.36 a et b

M (g/mol)=499.52

$C_{24}H_{37}O_8NP$

White solid 2 diastereomers 3.36 a and b de=33%

Overall yield=51%

Dia I Yield=67%

$^1$H NMR (400.13 MHz, CDCl$_3$): δ 1.23 (t, 3H, $^9$CH$_3$), 1.26 (t, 3H, $^{11}$CH$_3$), 1.37 (s, 3H, CH$_3$), 1.40 (s, 3H, CH$_3$), 1.42 (s, 3H, CH$_3$), 1.44 (s, 3H, CH$_3$), 2.27 (s, 3H, CH$_{3Tol}$), 3.80 (ABX, 4H, $^{8,10}$CH$_2$), 4.15 (dd, 1H, $^3J_{H-H}$=3.6 Hz, $^2J_{P-H}$=7.8 Hz, $^1$CH), 4.18 (d, 2H, $^3J_{H-H}$=4.9 Hz, $^6$CH$_2$), 4.31 (ddd, 1H, $^3J_{H-H}$=7.3 Hz, $^3J_{H-H}$=6.6 Hz, $^3J_{P-H}$=1.8 Hz, $^4$CH), 4.40 (AB, 1H, $^5$CH), 4.45 (dl, 1H, $^3J_{H-H}$=6.8 Hz, $^3$CH), 4.85 (ddd, 1H, $^3J_{H-H}$=3.6 Hz, $^3J_{H-H}$=7.2 Hz, $^3J_{P-H}$=23.7 Hz, $^2$CH), 4.94 (d, 1H, $^2J_{P-H}$=9.8 Hz, $^7$CH), 6.71 (d, 2H, CH$_{Ar}$Tol), 7.03 (d, 2H, CH$_{Ar}$Tol).

MS HR$^+$ (NBA): Theoretical mass 499.2413; Experimental mass 499.2418.

Dia II Yield=33%

$^1$H NMR (400.13 MHz, CDCl$_3$): δ 1.21 (t, 3H, $^9$CH$_3$), 1.34 (t, 3H, $^{11}$CH$_3$), 1.38 (s, 3H, CH$_3$), 1.39 (s, 3H, CH$_3$), 1.43 (s, 3H, CH$_3$), 1.60 (s, 3H, CH$_3$), 2.27 (s, 3H, CH$_3$Tol), 3.77 (m, 4H, $^{8,10}$CH$_2$), 4.15 (d, 2H, $^3J_{H-H}$=2.8 Hz, $^6$CH$_2$), 4.19 (dd, 1H, $^3J_{H-H}$=4.1 Hz, $^2J_{P-H}$=17.0 Hz, $^1$CH), 4.41-4.48 (m, 2H, $^3$CH+$^5$CH), 4.58 (ddd, 1H, $^3J_{H-H}$=2.7 Hz, $^3J_{H-H}$=1.5 Hz, $^3J_{P-H}$=8.0 Hz, $^4$CH), 4.74 (ddd, 1H, $^3J_{H-H}$=4.1 Hz, $^3J_{H-H}$=6.8 Hz, $^3J_{P-H}$=17.8 Hz, $^2$CH), 4.87 (d, 1H, $^2J_{P-H}$=4.8 Hz, $^7$CH), 6.61 (d, 2H, CH$_{Ar}$Tol), 7.03 (d, 2H, CH$_{Ar}$Tol).

MS HR$^+$ (NBA): Theoretical mass 499.2335; Experimental mass 499.2326.

General Procedure for Aromatic Nucleophilic Substitutions Using Compound 3.3 as Starting Material In a 50 ml two-necked flask that had been previously deoxygenated and under nitrogen atmosphere were introduced 500 mg of phosphinosugar 3.3a (1.20 mmol), 10 ml of anhydrous DMF. To this suspension were then added 40 mg of sodium hydride (1.2 eq.), in a single step and at room temperature. An oil can arranged on the assembly enabled to observe the hydrogen evolution. Once this evolution was over, the medium was gelled and aryl halide (1 eq.) was added thereto.

The medium was then stirred at room temperature for 4 hours.

The clear, homogenous and coloured reaction medium was then evaporated under reduced pressure. The residue obtained was taken up in 50 ml of chloroform, this organic phase was then washed with 25 ml of a sodium chloride saturated solution.

The organic phase was dried, filtered then evaporated to give a yellow oily residue.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-oxy-p-nitrophenyl Chromatography on a silica gel ChromatographyCH$_2$Cl$_2$/AcOEt from 100/0 to 0/100)

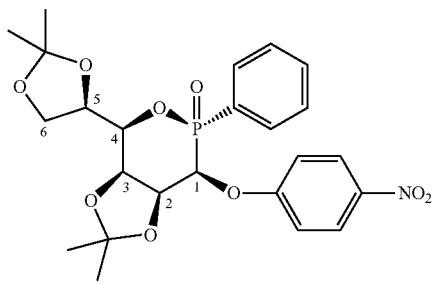

3.9a

M (g/mol)=505.47

$C_{24}H_{28}NO_9P$

Yield=90%

White solid 1 diastereomer 3.9a $^1$H NMR (400.13 MHz, DMSO): δ 1.43 (s, 6H, 2 CH$_3$), 1.49 (s, 3H, CH$_3$), 1.77 (s, 3H, CH$_3$), 1.60 (s, 3H, CH$_3$), 4.21 (d, 2H, $^3J_{H-H}$=5.2 Hz, $^6$CH$_2$), 4.33 (dl, 1H, $^3J_{P-H}$=9.3 Hz, $^1$CH), 4.54 (q, 1H, $^3J_{H-H}$=5.5 Hz, $^3J_{P-H}$=11.7 Hz, $^4$CH), 4.78 (m, 2H, $^5$CH+$^3$CH), 5.01 (ddd, 1H, $^3J_{H-H}$=3.3 Hz, $^3J_{H-H}$=7.8 Hz, $^3J_{P-H}$=22.4 Hz, $^2$CH), 6.97 (dl, 2H, CH$_{Ar}$), 7.43-7.62 (m, 3H, CH$_{Ar}$), 7.73-7.81 (m, 2H, CH$_{Ar}$), 8.09 (dl, 2H, CH$_{Ar}$).

MS HR$^+$ (NBA): Theoretical mass 506.1580; Experimental mass 506.1591.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-oxy-3,4-difluorophenyl Chromatography on a silica gel column (gradient CH$_2$Cl$_2$/AcOEt from 100/0 to 50/50)

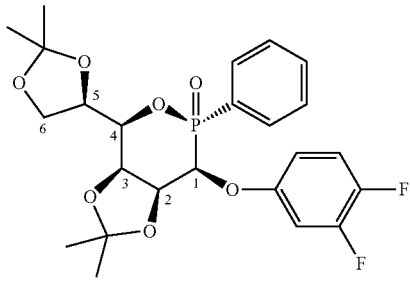

3.9c

M (g/mol)=496.45
C$_{24}$H$_{27}$F$_2$O$_7$P
Yield=88%
White solid
1 diastereomer 3.9c
$^1$H NMR (400.13 MHz, CDCl$_3$): δ 1.41 (s, 3H, CH$_3$), 1.43 (s, 3H, CH$_3$), 1.47 (s, 3H, CH$_3$), 1.70 (s, 3H, CH$_3$), 4.06 (d, 1H, $^3J_{H-H}$=3.0 Hz, $^3$CH), 4.17 (m, 2H, $^6$CH$_2$+$^1$CH), 4.47 (dd, 1H, $^3J_{H-H}$=6.1 Hz, $^3J_{P-H}$=11.6 Hz, $^4$CH), 4.66 (AB, 1H, $^5$CH), 4.82 (ddd, 1H, $^3J_{H-H}$=1.9 Hz, $^3J_{H-H}$=4.2 Hz, $^3J_{P-H}$=24.0 Hz, $^2$CH), 7.52-7.92 (m, 8H, CH$_{Ar}$).
MS HR$^+$ (NBA): Theoretical mass 496.3953; Experimental mass 496.3962.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-oxy-3,4-dinitrophenyl Chromatography on a silica gel column (gradient CH$_2$Cl$_2$/AcOEt from 100/0 to 0/100)

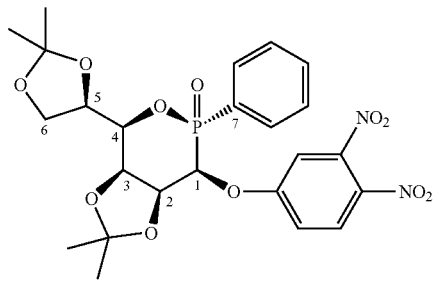

3.9b

M (g/mol)=550.46
C$_{24}$H$_{27}$N$_2$O$_{11}$P
1 diastereomer 3.9b
Yield=91%
White solid
$^1$H NMR (400.13 MHz, CDCl$_3$): δ 1.25 (s, 3H, CH$_3$), 1.35 (s, 3H, CH$_3$), 1.45 (s, 3H, CH$_3$), 1.61 (s, 3H, CH$_3$), 3.99 (m, 2H, $^6$CH$_2$), 4.33 (d, 1H, $^3J_{P-H}$=5.9 Hz, $^1$CH), 4.54 (ls, 1H, $^4$CH), 4.86 (d, 1H, $^3J_{H-H}$=6.8 Hz, $^5$CH), 5.28 (dd, 1H, $^3J_{H-H}$=6.9 Hz, $^3J_{P-H}$=23.0 Hz, $^2$CH), 5.01 (sl, 1H, $^3$CH), 7.39-8.43 (m, 8H, CH$_{Ar}$).
MS HR$^+$ (NBA): Theoretical mass 551.1431; Experimental mass 551.1432.

4-(2,2-Dimethyl-[1,3]dioxolan-4-yl)-2,2-dimethyl-2-oxo-2-phenyl-tetrahydro-6λ*5*-[1,3]dioxolo[4,5-d][1,2]oxaphosphinan-3-oxy-p-aminophenyl In a 50 ml two-necked flask, that had been previously deoxygenated and under nitrogen atmosphere were introduced 500 mg of nitrated compounds 3.9a, 500 mg of palladium on carbon, and 20 ml of absol. ethanol. A partial vacuum was then created in the assembly prior to introducing hydrogen. The medium was stirred at room temperature for 6 hours. The reaction developpement was monitored by NMR $^{31}$P.
The medium was then filtered on Celite so as to remove the palladium. The filtrate obtained was then evaporated under reduced pressure, to give an oily residue purified by chromatography on a silica gel column. Purification: Chromatography on a silica gel column (gradient CH$_2$Cl$_2$/AcOEt from 80/20 to 0/100).

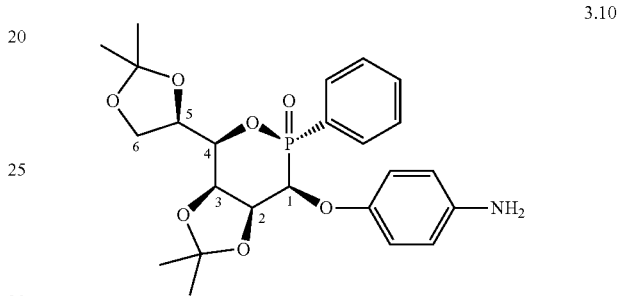

3.10

M (g/mol)=474.50
C$_{25}$H$_{31}$O$_7$P
1 diastereomer 3.10
Yield=96%
White solid
$^1$H NMR (400.13 MHz, CDCl$_3$): δ 1.34 (s, 6H, CH$_3$), 1.40 (s, 3H, CH$_3$), 1.69 (s, 3H, CH$_3$), 1.87 (sl, 2H, NH$_2$), 4.11 (d, 2H, $^3J_{H-H}$=5.3 Hz, $^6$CH$_2$), 4.24 (dl, 1H, $^3J_{P-H}$=7.1 Hz, $^1$CH), 4.46 (m, 4H, $^5$CH), 4.65 (d, 1H, $^3J_{H-H}$=3.3 Hz, $^4$CH),), 4.68 (dl, 1H, $^3J_{H-H}$=7.2 Hz, $^3$CH), 4.96 (ddd, 1H, $^3J_{H-H}$=3.2 Hz, $^3J_{H-H}$=7.8 Hz, $^3J_{H-H}$=22.3 Hz, $^2$CH), 6.87 (d, 2H, CH$_{Ar}$), 7.38-7.48 (m, 3H, CH$_{Ar}$), 7.68 (d, 2H, CH$_{Ar}$), 7.98 (d, 2H, CH$_{Ar}$).
MS HR$^+$ (NBA): Theoretical mass 476.1838; Experimental mass 476.1848.

4,5-bis-benzyloxy-6-benzyloxymethyl-2-octyl-2-oxo-2θ-[1,2]oxaphosphinan-3-ol (3.69)

This compound was obtained similarly to compound 3.3, starting from 2,3,5-tri-O-benzyl-D-arabinofuranose 3.45 and ethyl octylhydrogenophosphinate 3.13.

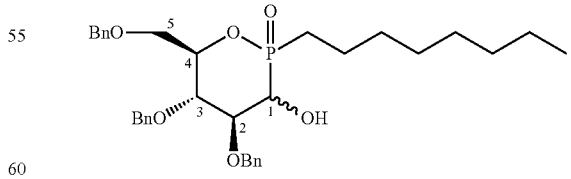

M(g/mol)=580.71
C$_{34}$H$_{45}$O$_6$P
3 diastereomers
Yield$_{(overall)}$=42%
Dia I $^{31}$P RMN (161.97 MHz, CDCl$_3$): δ 47.4
Dia II $^{31}$P RMN (161.97 MHz, CDCl$_3$): δ 48.1

4,5-bis-benzyloxy-6-benzyloxymethyl-2-phenylpropyl-2-oxo-2λ⁵-[1,2]oxaphosphinan-3-ol (3.70)

This compound was obtained similarly to compound 3.3, starting from 2,3,5-tri-O-benzyl-D-arabinofuranose 3.45 and ethyl phenylpropylhydrogenophosphinate 3.23.

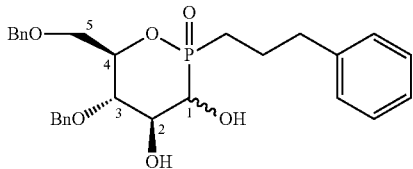 [SMILES: O=P1(CCCc2ccccc2)O[C@H](COCc2ccccc2)[C@@H](OCc2ccccc2)[C@H](O)C1O]

M(g/mol)=586.67
$C_{35}H_{39}O_6P$
2 diastereomers
Yield$_{(overall)}$=39%
Dia I $^{31}$P RMN (161.97 MHz, CDCl₃): δ 45.6
Dia II $^{31}$P RMN (161.97 MHz, CDCl₃): δ 46.8

4-(2,2-Dimethyl-[1,3]dioxolan-4-yl)-2,2-dimethyl-2-oxo-2-[3-methoxyphenyl]-tetrahydro-6λ*5*-[1,3]dioxolo[4,5-d][1,2]oxaphosphinan-3-ol (3.74)

This compound was obtained similarly to compound 3.3, starting from 2,3,5-tri-O-benzyl-D-arabinofuranose 3.45 and ethyl m-methoxyphenylhydrogenophosphinate 3.59.

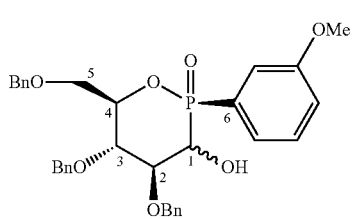

M(g/mol)=574.21
$C_{33}H_{35}O_7P$
4 diastereomers
Yield=31% $^{31}$P RMN (101.25 MHz, CDCl₃): δ 36.5
$^1$H RMN (400.13 MHz, CDCl₃): δ1.38 (s, 3H, CH₃), 1.40 (s, 3H, CH₃), 1.44 (s, 3H, CH₃), 1.67 (s, 3H, CH₃), 2.40 (s, 3H, CH₃), 3.48 (dd, $^3J_{HH}$=11.47 Hz, $^3J_{PH}$=3.87 Hz, 1H, OH), 4.01 (dd, $^3J_{HH}$=4.11 Hz, $^3J_{HH}$=11.47 Hz, 1H, $^1$CH), 4.10 (ddd, $^3J_{HH}$=1.21 Hz, $^3J_{HH}$=6.91 Hz, $^3J_{PH}$=2.36 Hz, 1H, $^4$CH), 4.11 (dd, $^2J_{HH}$=9.00 Hz, $^3J_{HH}$=5.08 Hz, 1H, $^6$CH), 4.13 (dd, $^2J_{HH}$=9.00 Hz, $^3J_{HH}$=5.86 Hz, 1H, $^6$CH), 4.43 (ddd, $^3J_{HH}$=5.86 Hz, $^3J_{HH}$=5.08 Hz, $^3J_{HH}$=6.91 Hz, 1H, $^5$CH), 4.62 (ddd, $^3J_{HH}$=7.94 Hz, $^3J_{HH}$=1.21 Hz, $^4J_{PH}$=1.08 Hz, 1H, $^3$CH), 4.81 (ddd, $^3J_{PH}$=24.59 Hz, $^3J_{HH}$=4.11 Hz, $^3J_{HH}$=7.54 Hz, 1H, $^2$CH), 7.29 (dd, $^3J_{HH}$=2.92 Hz, $^4$J=7.16 Hz, 2H, CH$_{Arom}$), 7.69 (dd, $^3J_{HH}$=10.08 Hz, $^4$J=12.00 Hz, 2H, CH$_{Arom}$)

4,5-bis-benzyloxy-6-benzyloxymethyl-2-thienyl-2-oxo-2λ⁵-[1,2]oxaphosphinan-3-ol

This compound was obtained similarly to compound 3.3, starting from 2,3,5-tri-O-benzyl-D-arabinofuranose 3.45 and ethyl 2-thienylhydrogenophosphinate 3.15.

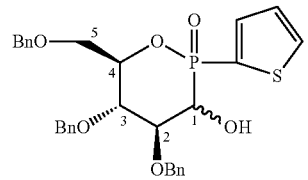

3.72

M(g/mol)=550.62
$C_{30}H_{35}O_6PS$
4 diastereomers
Yield$_{(overall)}$=53%
Dia I $^{31}$P RMN (161.97 MHz, CDCl₃): δ 32.6
MS FAB⁺ (NBA): m/z(%) 551.21[M+H⁺](80%); 552.22 [M+2H⁺]$^1$(15%), 1101.37 [2M+H⁺] (15%).
Dia II $^{31}$P RMN (161.97 MHz, CDCl₃): δ 28.4
Dia III $^{31}$P RMN (161.97 MHz, CDCl₃): δ 29.3
Dia IV $^{31}$P RMN (161.97 MHz, CDCl₃): δ 30.4

4,5-bis-benzyloxy-6-benzyloxymethyl-2-phenyl-2-oxo-2λ⁵-[1,2]oxaphosphinan-3-ol (3.75)

This compound was obtained similarly to compound 3.3, starting from 2,3,5-tri-O-benzyl-D-xylofuranose (synthesized as described in Desvergnes S., Py S., Vallée Y., *J. Org. Chem.*, 2005. 70, 1459-1462) and methyl phenylhydrogenophosphinate 3.4.

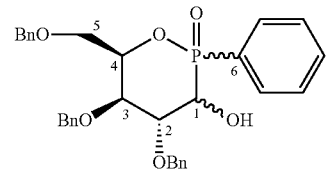

M(g/mol)=544.59
$C_{32}H_{33}O_6P$
4 diastereomers
Yield$_{(overall)}$=67%
Dia I $^{31}$P RMN (161.97 MHz, CDCl₃): δ 35.4
$^1$H RMN (400.13 MHz, CDCl₃): δ 3.71 (m, 2H, $^5$CH₂), 3.80 (q, 1H, $^3J_{P-H}$=9.9 Hz, $^3J_{H-H}$=6.8 Hz, $^1$CH), 4.12 (q, 1H, $^3J_{P-H}$=22.0 Hz, $^3J_{H-H}$=3.5 Hz, $^3J_{H-H}$=5.1 Hz, $^2$CH), 4.39-4.54 (m, 6H, CH₂OBn), 4.61 (dd, 1H, $^3J_{P-H}$=13.5 Hz, $^3J_{H-H}$=3.3 Hz, $^4$CH), 4.73 (td, 1H, $^3J_{H-H}$=6.6 Hz, $^3$CH), 6.83-7.88 (m, 20H, CH$_{Ar}$).
Dia II $^{31}$P RMN (161.97 MHz, CDCl₃): δ 33.2
$^1$H RMN (400.13 MHz, CDCl₃): δ 3.08 (dl, 1H, $^3J_{P-H}$=10.9 Hz, $^1$CH), 3.49 (m, 2H, $^5$CH₂), 3.74 (dl, 1H, $^3J_{H-H}$=4.6 Hz, $^3$CH), 4.00 (td, 1H, $^3J_{H-H}$=4.3 Hz, $^3J_{P-H}$=24.8 Hz, $^2$CH), 4.36-4.64 (m, 6H, CH₂OBn), 5.01 (q, 1H, $^4$CH), 6.83-7.88 (m, 20H, CH$_{Ar}$).

4,5-bis-benzyloxy-6-benzyloxymethyl-2-(p-methoxy)phenyl-2-oxo-2λ⁵-[1,2]oxaphosphinan-3-aminobenzyl This compound was obtained similarly to compound 3.3, starting from 2,3,5-tri-O-benzyl-N-benzyl-D-arabinosylamine 3.78 and ethyl p-methoxyphenylhydrogenophosphinate 3.49.

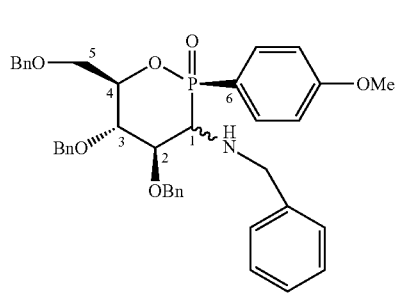

3.73

M(g/mol)=663.76
$C_{40}H_{42}NO_6P$
3 diastereomers
Yield$_{global}$=74%
Dia I $^{31}$P RMN (161.97 MHz, CDCl$_3$): δ 38.2
Dia II $^{31}$P RMN (161.97 MHz, CDCl$_3$): δ 37.3
Dia III $^{31}$P RMN (161.97 MHz, CDCl$_3$): δ 32.5

4,5-bis-benzyloxy-6-benzyloxymethyl-phenyl-2-oxo-2λ$^5$-[1,2]oxaphosphinan-3-aminobenzyl This compound was obtained similarly to compound 3.3, starting from 2,3,5-tri-O-benzyl-N-benzyl-D-arabinosylamine 3.78 and ethyl phenylhydrogenophosphinate 3.4.

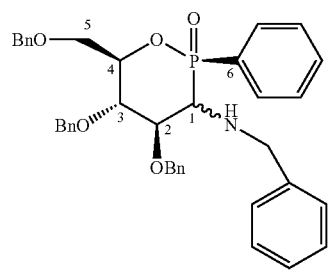

3.79

M(g/mol)=633.46
$C_{39}H_{40}NO_6P$
2 diastereomers
Yield$_{global}$=67%
Dia I $^{31}$P RMN (161.97 MHz, CDCl$_3$): δ 37.1
Dia II $^{31}$P RMN (161.97 MHz, CDCl$_3$): δ 32.7

4,5-bis-benzyloxy-6-benzyloxymethyl-2-diethoxymethyl-2-oxo-2λ$^5$-[1,2]oxaphosphinan-3-ol In a Schlenk tube that had been previously deoxygenated and under nitrogen atmosphere were introduced 500 mg of protected arabinose 3.45 (1.2 mmol), 10 ml of anhydrous THF, 30 mg of t-BuOK (0.24 mmol, 0.2 eq.) and 240 mg of ethyl diethoxymethylphosphinate (1.2 mmol, 1 eq.). The medium was stirred at room temperature for 15 hours, the developpement of the reaction being monitored by NMR $^{31}$P.

When the conversion rate attained 100%, 25 ml of a 0.1N hydrochloric acid solution were added, as well as 25 ml of a sodium chloride saturated solution. The organic phase thus obtained was then extrated three times with 50 ml of chloroform. The organic phases were then dryed on magnesium sulfate and evaporated under reduced pressure.

The oily residue was dried under a higher vacuum, and was then directly transferred to the deprotection step. This mixture was made of a mixture of 3 diastereomers (5/4/1)

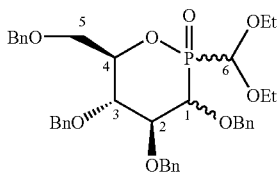

3.46

M (g/mol)=660.75
$C_{38}H_{45}O_8P$
3 diastereomers
Yield=62%
colourless oil 4,5-bis-benzyloxy-6-benzyloxymethyl-2-hydro-2-oxo-2X$^5$-[1,2]oxaphosphinan-3-ol In a Schott tube were introduced the mixture of diastereomers 3.46 and 10 ml of a 0.1N hydrochloric acid solution. The tube was closed and the medium was heated under stirring at 80° C. for one hour. The reaction developpement was monitored by decoupled NMR 31$^P$ so as to observe the presence of P—H type bonds characterized by coupling constants of about 600 Hz.

The medium was then evaporated under high vacuum until a white solid was obtained. This solid corresponded to a mixture containing only two diastereomers and was directly used in the next step without further purification.

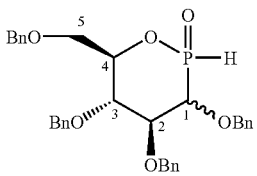

3.47

M (g/mol)=558.62
$C_{33}H_{35}O_6P$
Yield=100%
3 diastereomers
colourless oil

General Procedure for Pallado-Catalyzed Arylations on Compound 3.47

In a three-necked flask provided with a cooler under nitrogen, were successively introduced 500 mg of diastereomer mixture 3.47 (0.9 mmol), 125 mg of tetrakis(triphenylphosphine)palladium (0.09 mmol, 0.1 eq.), 5 ml of anhydrous toluene, aryl halide (0.9 mmol, 1 eq.) and 365 μl of triethylamine (2.7 mmol, 3 eq.). The reaction medium was heated to 70° C. for 4 h under magnetic stirring.

The reaction medium was filtered on Celite, the filtrate thus obtained was evaporated under reduced pressure. The oily residue was then purified on a silica gel column (gradient CH$_2$Cl$_2$/AcOEt from 100/0 to 0/100).

4,5-bis-benzyloxy-6-benzyloxymethyl-2-phenyl-2-oxo-2λ$^5$-[1,2]oxaphosphinan-3-ol Chromatography on a silica gel column (gradient CH$_2$Cl$_2$/AcOEt from 100/0 to 50/50)

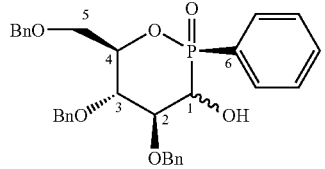

3.48a

M (g/mol)=544.59
C$_{32}$H$_{33}$O$_6$P
2 diastereomers 3.48 a and b
Yield$_{global}$=60%
de=60%
White solid
Dia I Yield=81%
$^1$H NMR (400.13 MHz, CDCl$_3$): δ 3.68 (dd, 1H, $^3J_{H-H}$=1.9 Hz, $^2J_{H-H}$=11.1 Hz, $^5$CH$_{2a}$), 3.86-3.91 (m, 2H, $^5$CH$_{2b}$+$^4$CH), 3.94 (dl, 1H, $^2J_{P-H}$=9.6 Hz, $^1$CH), 4.11 (m, 1H, $^3$CH), 4.44-4.63 (m, 4H, 2 CH$_2$OBn), 4.80-4.84 (m, 2H, CH$_2$OBn), 4.89 (dd, 1H, $^3J_{P-H}$=11.3 Hz, $^3J_{H-H}$=4.7 Hz, $^2$CH), 7.12-7.74 (m, 20H, CH$_{Ar}$).
MS HR$^+$ (NBA): Theoretical mass 545.2093; Experimental mass 545.2104.
Dia II Yield=19%
$^1$H NMR (400.13 MHz, CDCl$_3$): δ 3.68 (dd, 1H, $^3J_{H-H}$=1.7 Hz, $^3J_{H-H}$=11.2 Hz, $^5$CH$_{2a}$), 3.90 (td, 1H, $^3J_{H-H}$=2.8 Hz, $^3J_{P-H}$=11.2 Hz, $^5$CH$_{2b}$), 4.19 (d, 1H, $^3J_{H-H}$=9.8 Hz, $^4$CH), 4.26 (dd, 1H, $^3J_{H-H}$=2.4 Hz, $^3J_{P-H}$=9.5 Hz, $^3$CH), 4.34 (t, 1H, $^3J_{H-H}$=2.7 Hz, $^1$CH), 4.45-4.67 (m, 6H, 3CH$_2$OBn), 4.83 (d, 1H, $^2J_{P-H}$=10.7 Hz, $^2$CH), 7.13-7.91 (m, 20H, CH$_{Ar}$).
MS HR$^+$ (NBA): Theoretical mass 545.2093; Experimental mass 545.2112.

4,5-bis-benzyloxy-6-benzyloxymethyl-2-(3,5-fluoro)phenyl-2-oxo-2λ$^5$-[1,2]oxaphosphinan-3-ol Chromatography on a silica gel column (gradient CH$_2$Cl$_2$/AcOEt from 100/0 to 50/50)

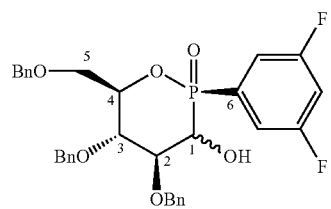

3.50

M (g/mol)=580.57
C$_{32}$H$_{31}$F$_2$O$_6$P
2 diastereomers 3.50 a and b
de=98%
Yield=69%
White solid
$^1$H NMR (400.13 MHz, CDCl$_3$): δ 3.67 (dd, 1H, $^3J_{H-H}$=1.9 Hz, $^3J_{P-H}$=11.2 Hz, $^5$CH$_{2a}$), 3.82-3.91 (m, 3H, $^3$CH+$^5$CH$_{2b}$+$^4$CH), 4.08 (td, 1H, $^3J_{H-H}$=2.9 Hz, $^3J_{P-H}$=9.4 Hz, $^1$CH), 4.41-4.57 (m, 4H, 2CH$_2$OBn), 4.79-4.82 (m, 2H, CH$_2$OBn), 4.85 (t, 1H, $^2J_{P-H}$=10.9 Hz, $^2$CH), 6.93-7.28 (m, 18H, CH$_{Ar}$).

MS HR$^+$ (NBA): Theoretical mass 581.1905; Experimental mass 581.1929.

4,5-bis-benzyloxy-6-benzyloxymethyl-2-(p-methoxy)phenyl-2-oxo-2λ$^5$-[1,2]oxaphosphinan-3-ol Chromatography on a silica gel column (gradient CH$_2$Cl$_2$/AcOEt from 100/0 to 50/50)

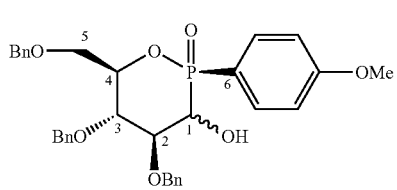

3.51a et b

M (g/mol)=574.62
C$_{33}$H$_{35}$O$_7$P
2 diastereomers 3.51 a and b
de=72%
Yield$_{global}$=67%
White solid
Dia I Yield=86%
$^1$H NMR (400.13 MHz, CDCl$_3$): δ 3.68 (dd, 1H, $^3J_{H-H}$=2.1 Hz, $^3J_{P-H}$=11.1 Hz, $^5$CH$_{2a}$), 3.78 (s, 3H, CH$_3$Anisole), 3.86-3.91 (m, 3H, $^5$CH$_{2b}$+$^1$CH+$^4$CH), 4.04 (dd, 1H, $^3J_{H-H}$=9.1 Hz, $^3J_{P-H}$=25.5 Hz, $^3$CH), 4.45-4.60 (m, 4H, 2CH$_2$OBn), 4.89 (s, 2H, CH$_2$OBn), 4.91 (d, 1H, $^2J_{P-H}$=12.1 Hz, $^2$CH), 6.89-7.51 (m, 19H, CH$_{Ar}$).
MS HR$^+$ (NBA): Theoretical mass 574.5963; Experimental mass 574.5969.
Dia II Yield=14%
$^1$H NMR (400.13 MHz, CDCl$_3$): δ 3.62 (dd, 1H, $^3J_{H-H}$=1.8 Hz, $^3J_{H-H}$=10.9 Hz, $^5$CH$_{2a}$), 3.76 (s, 3H, CH$_3$ Anisole), 3.89 (td, 1H, $^3J_{H-H}$=2.6 Hz, $^3J_{H-H}$=13.4 Hz, $^5$CH$_{2b}$), 4.13 (dl, 1H, $^3J_{H-H}$=9.6 Hz, $^4$CH), 4.23 (dd, 1H, $^3J_{H-H}$=2.7 Hz, $^3J_{P-H}$=7.3 Hz, $^1$CH), 4.29 (t, 1H, $^3J_{H-H}$=2.9 Hz, $^3$CH), 4.41-4.71 (m, 6H, 2CH$_2$OBn), 4.81 (dl, 1H, $^3J_{P-H}$=10.8 Hz, $^2$CH), 6.88-7.65 (m, 19H, CH$_{Ar}$).
MS HR$^+$ (NBA): Theoretical mass 574.5963; Experimental mass 574.5976.

4,5-bis-benzyloxy-6-benzyloxymethyl-2-(p-nitro)phenyl-2-oxo-2λ$^5$-[1,2]oxaphosphinan-3-ol Chromatography on a silica gel column (gradient CH$_2$Cl$_2$/AcOEt from 100/0 to 50/50)

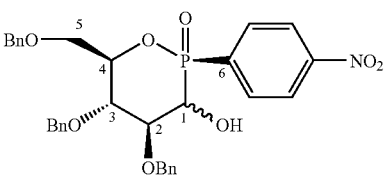

3.52

M (g/mol)=589.59
C$_{32}$H$_{32}$NO$_8$F
2 diastereomers 3.52 a and b
de=97%
Yield=67%
White solid $^1$H NMR (400.13 MHz, CDCl$_3$): δ 3.38-3.64 (m, 4H, $^5$CH$_2$+$^3$CH+$^4$CH), 3.81 (d, 1H, $^3$J$_{P-H}$=10.2 Hz, $^1$CH), 4.46-4.57 (m, 4H, 2CH$_2$OBn), 4.83 (s, 2H, CH$_2$OBn), 4.84 (d, 1H, $^2$J$_{P-H}$=10.8 Hz, $^2$CH), 7.12-7.96 (m, 15H, CH$_{Ar}$), 7.98 (dt, 2H, CH o nitro), 8.27 (d, 2H, CH m nitro).

MS FAB$^+$ (NBA): m/z (%) 590 [M+H$^+$] (80%); 545 [C$_{33}$H$_{34}$O$_6$P+H$^+$] (20%).

MS HR$^+$ (NBA): Theoretical mass 589.1674; Experimental mass 589.1688.

Compound 3.54

In a Schlenk tube that had been previously deoxygenated and under nitrogen atmosphere were introduced 180 mg of phosphinosugar 3.19a (0.44 mmol, 1 eq.), 292 mg of mannose trichloroacetamidate 3.53 (0.7 mmol, 1.6 eq.) and 10 ml dichloromethane. The medium was then brought to 0° C. prior to adding 0.1 ml of BF$_3$ etherate (0.65 mmol, 1.62 eq.). Temperature was maintained at 0° C. for 30 minutes then warmed to 25° C. and the mixture was stirred for another 30 minutes.

The medium was placed in an ice bath, then a sodium hydrogenocarbonate saturated solution was added under vigourous stirring. The thus obtained aqueous phase was extracted with diethyl ether. The organic phases were combined, dryed on sodium sulfate and then evaporated under reduced pressure. The oily residue obtained was taken up in a mixture of ethyl acetate and hexane, and stored at 4° C. overnight. The disaccharide did precipitate as a powdered white solid.

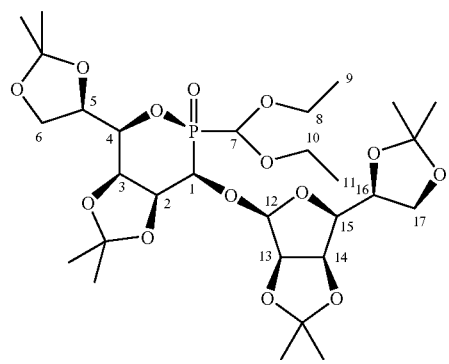

3.54

M (g/mol)=652.68
C$_{29}$H$_{49}$O$_{14}$P
Yield=53%
White solid $^1$H NMR (400.13 MHz, CDCl$_3$): δ 1.25 (t, 3H, $^9$CH$_3$), 1.26 (t, 3H, $^{11}$CH$_3$), 1.30-1.47 (8s, 24H, 8CH$_3$), 3.76-3.93 (m, 4H, $^{8,10}$CH$_2$), 4.05-4.09 (m, 3H, $^6$CH$_2$+$^{14}$CH), 4.14 (dd, 1H, $^3$J$_{H-H}$=3.7 Hz, $^3$J$_{H-H}$=8.7 Hz, $^{13}$CH), 4.23-4.28 (m, 1H, $^5$CH), 4.32 (q, 1H, $^3$J$_{H-H}$=1.5 Hz, $^3$J$_{P-H}$=2.8 Hz, $^4$CH), 4.33-4.36 (m, 2H, $^{17}$CH$_2$), 4.60-4.69 (m, 3H, $^1$CH+$^3$CH), 4.69 (d, 1H, $^3$J$_{H-H}$=5.9 Hz, $^{15}$CH), 4.87 (dd, 1H, $^3$J$_{H-H}$=3.2 Hz, $^3$J$_{H-H}$=6.0 Hz, $^{16}$CH), 4.91 (d, 2H, $^3$J$_{P-H}$=7.9 Hz, $^7$CH), 5.08 (ddd, 1H, $^3$J$_{H-H}$=2.8 Hz, $^3$J$_{H-H}$=7.8 Hz, $^3$J$_{P-H}$=22.6 Hz, $^2$CH), 5.24 (s, 1H, $^{12}$CH).

Compound 3.55

In a Schlenk tube that had been previously deoxygenated and under nitrogen atmosphere were introduced 180 mg of phosphinosugar 3.3a (0.46 mmol, 1 eq.), 300 mg of mannose trichloroacetamidate (0.75 mmol, 1.6 eq.) and 10 ml dichloromethane. The medium was then brought to 0° C. prior to adding 0.1 ml of BF$_3$ etherate (0.75 mmol, 1.62 eq.). Temperature was maintained at 0° C. for 30 minutes then warmed to 25° C. and the mixture was stirred for another 30 minutes.

The medium was placed in an ice bath, then a sodium hydrogenocarbonate saturated solution was added under vigourous stirring. The thus obtained aqueous phase was extracted with diethyl ether. The organic phases were combined, dryed on sodium sulfate and then evaporated under reduced pressure. The oily residue obtained was taken up in a mixture of ethyl acetate and hexane, and stored at 4° C. overnight. The disaccharide did precipitate as a powdered white solid.

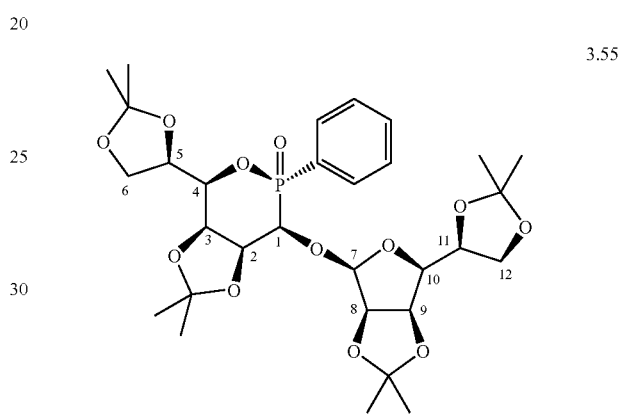

3.55

M (g/mol)=626.23
C$_{30}$H$_{43}$O$_{12}$P
Yield=70% (205 mg)
White solid $^1$H NMR (400.13 MHz, CDCl$_3$): δ 1.28- 1.69 (8s, 24H, 8CH$_3$), 3.24 (dd, 1H, $^3$J$_{H-H}$=8.3 Hz, $^3$J$_{H-H}$=5.7 Hz, $^{10}$CH), 3.33 (dd, 1H, $^3$J$_{H-H}$=3.0 Hz, $^3$J$_{H-H}$=7.7 Hz, $^9$CH), 3.57 (dd, 2H, $^3$J$_{H-H}$=8.3 Hz, $^3$J$_{H-H}$=6.4 Hz, $^{12}$CH$_2$), 4.05 (ddd, 2H, $^3$J$_{H-H}$=5.0 Hz, $^3$J$_{H-H}$=8.9 Hz, $^2$J$_{P-H}$=49.0 Hz, $^6$CH$_2$), 4.11 (m, 1H, $^{11}$CH), 4.39 (q, 1H, $^3$J$_{H-H}$=5.1 Hz, $^5$CH), 4.52 (dt, 1H, $^4$CH), 4.60 (t, 1H, $^1$CH), 4.69 (s, 1H, $^9$CH), 4.81 (d, 1H, $^3$J$_{H-H}$=2.9 Hz, $^3$CH), 5.18 (ddd, 1H, $^3$J$_{H-H}$=3.6 Hz, $^3$J$_{H-H}$=8.2 Hz, $^3$J$_{P-H}$=22.9 Hz, $^2$CH), 5.31 (s, 1H, $^7$CH), 7.49-7.92 (m, 5H, CH$_{Ar}$).

MS HR$^+$ (NBA): Theoretical mass 627.2570; Experimental mass 627.2521.

Compound 3.56

In a 100 mL flask were introduced 500 mg of dissacharide 3.55 (5.2 mmol) and 1.0 g of Amberlyst 15 sulfonic resin. 25 mL of anhydrous methanol were added thereto and the mixture was allowed to be gently stirred at 55° C. until complete deprotection (monitored by NMR $^{31}$P).

Filtration was performed on cotton and methanol was evaporated. The solid obtained was then dried by means of a dessicator.

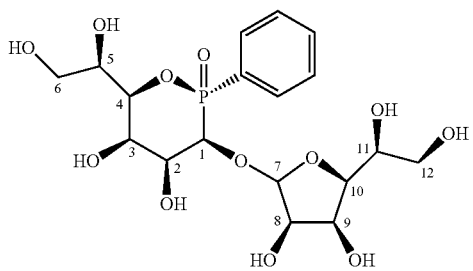

3.56

Results and analysis
M (g/mol)=466.38
$C_{18}H_{27}O_{12}P$
Yield=70% (205 mg)
White solid
$^1$H NMR (400.13 MHz, CDCl$_3$): δ 3.33 (q, 2H, CH$_2$), 3.59-3.91 (m, 10H, CH), 4.07 (ddd, 1H, $^3J_{H-H}$=8.8 Hz, $^3J_{H-H}$=11.6 Hz, $^3J_{P-H}$=20.2 Hz, $^2$CH), 4.19 (dd, 1H, $^3J_{H-H}$=1.0 Hz, $^3J_{P-H}$=11.3 Hz, CH), 4.25 (t, 1H, $^3J_{H-H}$=8.0 Hz, CH), 7.56-7.70 (m, 3H, CH$_{Ar}$), 7.84-7.92 (m, 2H, CH$_{Ar}$).

MS FAB$^+$ (NBA): m/z (%) 467 [M+H$^+$] (80%); 385 [$C_{12}H_{16}O_7P$+H$^+$] (20%).

B) Bio-Assays

The biologic activities of compounds of both families, derived from D-mannose and from D-arabinose, represented by the general formulas (19) and (20), as well as their deprotected analogues, were evaluated in vitro on (i) three types of astrocyte cell lines (a) to c)), one of which was derived from a rat glioblastoma, that is to say from a primitive malignant cancerous tumor extracted from glial cells of the central nervous system and (ii) a group of 5 human tumor cell lines (d)).

a) Spontaneously converted astrocytes collected from the cortex of a newborn rat (see Bochelen D., Langley K., Adamczyk M., Kupfberg, Hor F., Vincendon G., Mersel M., J. Neurosci. Res., 2000, 62, 99-111), that is to say from normal glial cells maintained in culture and that became able to divide to infinity. These cells are not able to induce tumors after implantation in the rat but did avoid the cell cycle regulation. This cell line was maintained in culture in culture flasks in the presence of 5 mL of culture medium MH5 comprising 70% of MEM and 30% of a Hanks solution. This medium was supplemented with 5% of foetal calf serum. The culture medium was changed every three days. Cells were incubated at 37° C. in an air/CO$_2$ atmosphere (95/5). For the experiments, a replanting was effected after removal of the culture medium, cells were treated for 4 to 5 minutes with trypsine (0.1%). The cell suspension was then placed in 5 mL of fresh medium, 50 µL of this solution were collected to perform the cell counting. Once the expected dilution had been obtained, the 96-well culture plates were seeded, the culture volume being 200 µL.

b) Astrocyte primary cultures from the cortex of a newborn rat for testing the so called "healthy cells". This primary culture was conducted based on the brain tissue removed from the cortex of a newborn rat. After homogeneization, trypsinization and centrifugation, cells were distributed in 24-well plates for about 3 weeks. Oligodendrocytes were then removed by stirring the culture plates for 30 minutes and by changing the supernatant with fresh medium.

c) C6 Cells from glioblastomas of rats. This is the cancerous cell model used. This line (Werthle M, Bochelen D, Adamczyk M, Kupferberg A, Poulet P, Chambron J, Lutz P, Privat A, Mersel M. Cancer Res. 1994 Feb. 15; 54(4):998-1003) that is well known to those skilled in the art, was a cell line derived from a rat cortex glioblastoma, where the tumor was induced by using N-nitrosomethylurea. These cells represent excellent tumor cell mimetics, with a high metabolism, hence a reduced division time. This cell line has a division time ranging from 10 to 12 hours. These remarkable particularities are its capacity to redifferenciate in astrocyte cells if the cyclic AMP rate is high and to induce tumors de novo in the rat. These cells were cultured in MEM (Minimum Essential Medium), in the presence of 5% of foetal calf serum. Incubation was conducted at 37° C. in a 5% CO$_2$ humidity atmosphere.

d) Human tumor cell lines from a variety of human cancer pathologies (carcinomas of colon, breast, prostate, liver and melanomes).

1. Material and Methods

The cells were seeded in 96-well plates with 2000 cells per well in 200 µL of MEM/HANKS (70/30) in the presence of 5% of foetal calf serum. The compounds were added 24 hours after seeding. Dissolved in ethanol, these compounds were diluted in culture medium, so that the amount of ethanol be equal in all the wells and does not exceed 0.3% of the final volume. The concentration range used did vary from 50 µM to 24 nM by conducting ½ to ½ serial dilutions. It was controlled that the tested compounds remain stable in the culture medium and do not decompose over the time. Control wells were prepared, that did not contain any compound but that did comprise the same amount of ethanol.

2. Effect Quantification

The activity evaluation of the test compounds was effected by measuring the cell viability in the culture wells, by means of a so called "neutral red assay" that did consist in contacting the cells with this dye, the accumulation of which in cell acidic compartments does express the health status of the latter. The neutral red test makes it thus possible to know the cytotoxic effect of a compound. The dye was used from a 0.33% stock solution in PBS. 20 µL of such solution were added to each culture well containing 300 µL of culture medium and the plates were incubated at 37° C. for three hours.

The supernatant of each well was then removed by succion. Because of their adherence, the cells remained fixed onto the well bottom, and a washing was hence performed with 200 µL of a PBS solution, so as to remove the non absorbed dye. The wells were evacuated again, and the cells were lyzed, thus salting out the dye in the well, this procedure being effected with a solution made of ethanol, water and acetic acid (50/49/1). The colour intensity obtained directly indicated the cell viability. It was quantified by measuring the absorbance at 570 nm. This measure was effected on a 96-well plate reader, of BIO-RAD Microplate reader 550 type, providing an optical density value (OD) for each well of culture.

Each 96-well plate comprised at least one series of 12 wells not treated with a compound (1), that were hence used as controls.

Thereafter IC$_{50}$ values were therefore determined by establishing the OD well X/OD control ratio, thus directly providing the percentage of living cells in the medium.

3. Results a) Cytotoxicity on the Spontaneously Converted Astrocytes (Qualitative Assay)

These assays conducted on compounds 3.28, 3.8, 3.5. 3.19a, 3.6 and 3.7. made it possible to demonstrate their cytotoxic activity on astrocyte type cells that were spontaneously converted collected from the cortex of newborn rats. The effect was evaluated by simple microscopic observation of the culture plates. This evaluation consisted in observing each day and for four days, at concentrations ranging from 50 µM to 400 nM. The evaluated compounds did present an activity at a very low concentration. An activity could be observed after 72 h to 96 h (days 3 and 4) for the whole evaluated compounds.

b) Cytotoxicity on the C6 Cell Line (Quantitative Assay)

The quantitative evaluation of the cytotoxicity of the compounds of the invention against modified cells that are said to be "cancerous" was conducted on the C6 cell line. Plates were seeded at a cell density of 2000 cells per well. This density enabled to obtain a 80% confluence after a 4 day-culture for non treated cells.

The $IC_{50}$ values that were determined by evaluating the cell viability, after incorporating the neutral red are presented in Table 1 hereafter. The values obtained, within the nano-molar and/or micromolar range, did demonstrate that the test compounds have an activity on the C6 cell ability to accumulate neutral red, that is to say on their viability. It should be noted that compounds 3.57, 3.30a and 3.51a when highly concentrated made it possible to reach a total mortality that confirms their cytotoxic capacity.

TABLE 1

| Compound | $IC_{50}$ (*) |
|---|---|
| 3.6 | 1.5 µM |
| 3.9a | 0.4 to 1 µM |
| 3.52 | 0.1 to 5 µM |
| 3.28 | 0.8 to 5 µM |
| 3.20a | 0.4 to 5 µM |
| 3.51a | 0.1 to 5 µM |
| 3.57 | 0.1 to 5 µM |
| 3.30a | 0.5 to 5 µM |
| 3.48a | 1 to 2 µM |
| 3.79 | 1 to 3 µM |
| 3.73 | 3 to 5 µM |

(*) Measures conducted on day 2 or 3.

The most active compounds are the compounds 3.30a, 3.51a and 3.57, the structures of which are given below as a reminder:

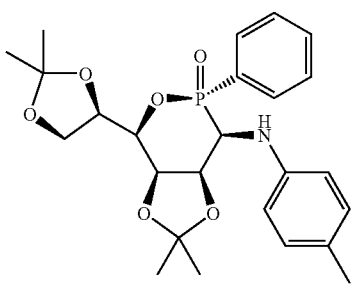

3.30a

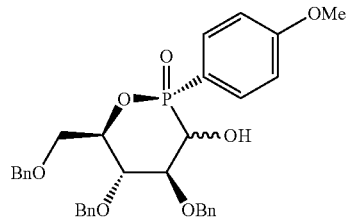

3.51a

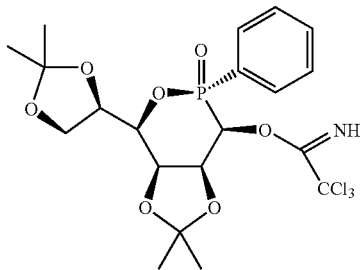

3.57

The results obtained seem to indicate that the following characteristics individually favor the activity: the presence of an aromatic ring on the phosphorus atom, a substitution of the heteroatom at the C1 position in a of the phosphorus atom in mannose derivatives, and a protection of the hydroxyl groups at the non anomeric position.

c) Cytotoxicity on the Non Modified Astrocytes (Quantitative Assay)

Cytotoxicity evaluation assays against the so called "healthy cells" were conducted on astrocyte primary cultures collected from the cortex of newborn rats, mimetizing the physiology of a so called "healthy cell", i.e. a non cancerous cell.

These cells being unmodified, their division time was very long (about 50 hours). It was thus necessary to choose a higher initial seeding concentration (5000 cells per well). The compounds (1) were introduced only after 96 hours so as to allow the cells to adhere to the well walls and to divide once or twice. The concentration range for the test compounds (1) varied from 50 µM to 24 nm as for the C6 cells. Controls were carried out the second day following the introduction of the compounds (1). Two plates were made available for each measurement.

FIG. 1 shows the effect of compounds 3.57, 3.30a and 3.51a, that presented an activity on the glioblastomas of rats against the so called "healthy cells". The control effected on the second day following the addition of the three test compounds did not show any significative effect of these compounds on the healthy cells. The viability percentages obtained only corresponded to variations around 100%, no value being greater than 20% of cell death. Similar assays were conducted on the compounds 3.30b, 3.52, 3.6 and 3.28 and also concluded for the absence of cytotoxicity on the same healthy cells.

To conclude, the tests that were performed on the so called healthy cells did not show any toxicity in vitro for several compounds of formula (1) according to the invention during the first two days of contact at concentrations up to 50 µM.

d) Cytotoxicity on Human Tumor Cell Lines

It has been shown that neoplastic transformation is often associated with characteristic changes in the expression of the blood group oligosaccharides, and their amounts usually increase during tumor progression and acquiring of malignant phenotype (Hakomori, 1996). Typical tumor-associated carbohydrate antigens are two carbohydrate structures named sialyl Lea [Sia α2-3 Gal β1-4 (Fuc α1-4) GlcNAc] and sialyl Lex [Sia α2-3 Gal β1-4 (Fuc α1-3) GlcNAc]. Low amounts of sialyl Lea antigen are also present on normal epithelial cells (Atkinson et al., 1982; Arends et al., 1983). Because these compounds may mimic the transition state involved in glycosylation reactions, the effect of oxaphosphinanes on cell glycosylation patterns were first investigated. After 72 hrs of treatment with one of the lead structure (compound 3.79), it

The invention claimed is:

1. A compound having the following general formula:

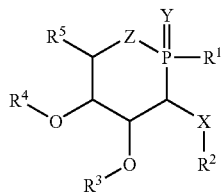

(1)

wherein:

Y represents an oxygen or a sulfur atom,

Z represents O or S, $R^1$ represents a hydrogen atom, an optionally substituted alkyl group or an aryl group, X represents an oxygen, a sulfur, a NH or $NR^7$ group, wherein $R^7$ is an optionally substituted alkyl group or an aryl group, and $R^2$ represents an aryl group, an optionally substituted alkyl group, a hydrogen atom, a trichloroacetimidate group (—C(=NH)CCl$_3$), an acyl, formyl, sulfonyl, sulfinyl, tert-butyldiphenylsilyl, allyl group, a saccharyl, ester, amide, thioamide, sulfonamide group, or X—$R^2$ represents a P(O)$R^{2'}R^{6'}$ group, wherein $R^{2'}$ and $R^{6'}$ represent independently from each other an aryl group, an optionally substituted alkyl group, OH, an alkoxy or an aryloxy group, $R^3$ and $R^4$ represent, independently from each other an aryl group, an optionally substituted alkyl group, a hydrogen atom, a trichloroacetimidate group, an acyl, formyl, sulfonyl, sulfinyl, tert-butyldiphenylsilyl group, an allyl, ester, amide, thioamide, sulfonamide group, or $R^3$ and $R^4$ taken together form a divalent radical of formula —$R^3$—$R^4$—, wherein —$R^3$—$R^4$— represents an isopropylidene, benzylidene, diphenyl methylidene, cyclohexyl methylidene group, and their substituted analogues, or a linear alkylene group, $R^5$ represents a hydrogen atom or a hydrocarbon group substituted with one or more heteroatoms selected from oxygen, sulfur or nitrogen atoms, provided that the compound of formula (1) is not:

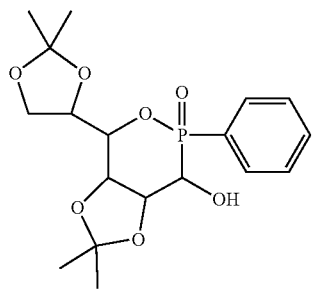

or

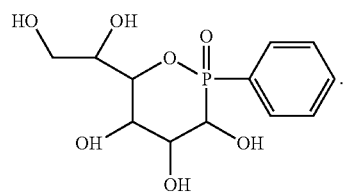

2. The compound according to claim 1, wherein Y=Z=O.

3. The compound according to claim 1, wherein $R^5$ is one of:

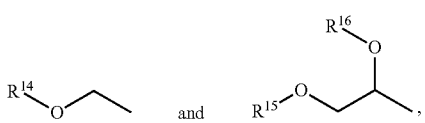

wherein $R^{14}$, $R^{15}$ and $R^{16}$ represent, independently from each other, a hydrogen atom, an aryl group, an optionally substituted alkyl group, a trichloroacetimidate group, an acyl, formyl, sulfonyl, sulfinyl, tert-butyldiphenylsilyl, allyl, ester, amide or a sulfonamide group, or $R^{15}$ and $R^{16}$, taken together, form a divalent radical of formula —$R^{15}$—$R^{16}$—, wherein —$R^{15}$—$R^{16}$— represents an isopropylidene, benzylidene, diphenyl methylidene, or a cyclohexyl methylidene group, and their substituted analogues or a linear alkylene group.

4. The compound according to claim 1 wherein the compound has a formula according to one of:

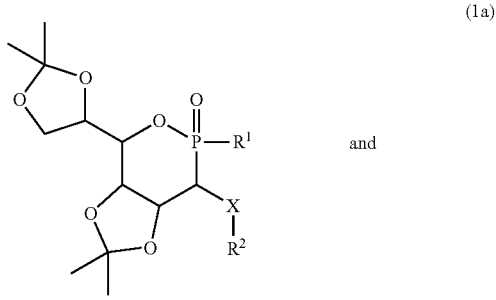

and wherein $R^1$, $R^2$ and X are such as defined in claim 1, and Bn represents the benzyl group.

5. The compound according to claim 1, wherein the compound has a formula selected from the group consisting of:

(19)

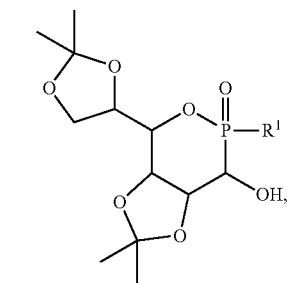

(20)

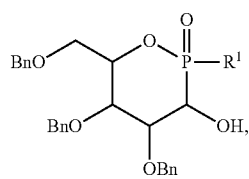

(22)

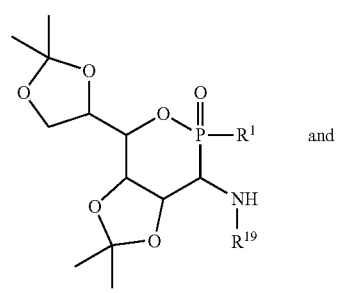

and (23)

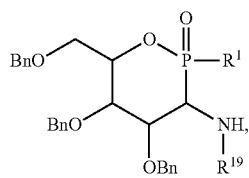

and
wherein $R^1$ is such as defined in claim 1, Bn represents the benzyl group, and $R^{19}$ represents a hydrogen atom, an aryl group or an optionally substituted alkyl group.

6. A drug comprising:
a compound of formula (1):

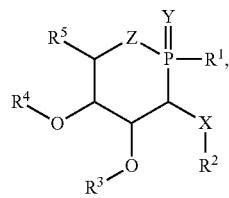

(1)

wherein:
Y represents an oxygen or a sulfur atom,
Z represents O or S, $R^1$ represents a hydrogen atom, an optionally substituted alkyl group or an aryl group,
X represents an oxygen, a sulfur, a NH or $NR^7$ group, wherein $R^7$ is an optionally substituted alkyl group or an aryl group, and
$R^2$ represents an aryl group, an optionally substituted alkyl group, a hydrogen atom, a trichloroacetimidate group (—C(=NH)CCl$_3$), an acyl, formyl, sulfonyl, sulfinyl, tert-butyldiphenylsilyl, allyl group, a saccharyl, ester, amide, thioamide, sulfonamide group, or X—$R^2$ represents a P(O)$R^{2'}R^{6'}$ group, wherein $R^{2'}$ and $R^{6'}$ represent independently from each other an aryl group, an optionally substituted alkyl group, OH, an alkoxy or an aryloxy group,
$R^3$ and $R^4$ represent, independently from each other an aryl group, an optionally substituted alkyl group, a hydrogen atom, a trichloroacetimidate group, an acyl, formyl, sulfonyl, sulfinyl, tert-butyldiphenylsilyl group, an allyl, ester, amide, thioamide, sulfonamide group, or $R^3$ and $R^4$ taken together form a divalent radical of formula —$R^3$—$R^4$—, wherein —$R^3$—$R^4$—represents an isopropylidene, benzylidene, diphenyl methylidene, cyclohexyl methylidene group, and their substituted analogues or a linear alkylene group, and
$R^5$ represents a hydrogen atom or a hydrocarbon group substituted with one or more heteroatoms selected from oxygen, sulfur or nitrogen atoms,
provided that the compound of formula (1) is not:

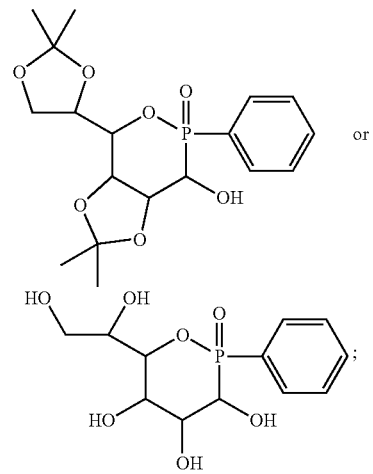

in combination with one or more pharmaceutically acceptable excipients and/or vehicles.

7. A pharmaceutical composition, comprising at least one compound of formula (1):

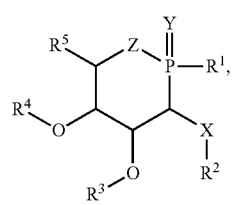

(1)

wherein:
Y represents an oxygen or a sulphur atom,
Z represents O or S, $R^4$ represents a hydrogen atom, an optionally substituted alkyl group or an aryl group,
X represents an oxygen, a sulfur, a NH or $NR^7$ group, wherein $R^7$ is an optionally substituted alkyl group or an aryl group, and
$R^2$ represents an aryl group, an optionally substituted alkyl group, a hydrogen atom, a trichloroacetimidate group (—C(=NH)CCl$_3$), an acyl, formyl, sulfonyl, sulfinyl, tert-butyldiphenylsilyl, allyl group, a saccharyl, ester, amide, thioamide, sulfonamide group, or X—R² represents a P(O)R²'R⁶' group, wherein R²' and R⁶' represent independently from each other an aryl group, an optionally substituted alkyl group, OH, an alkoxy or an aryloxy group, R³ and R⁴ represent, independently from each other an aryl group, an optionally substituted alkyl group, a hydrogen atom, a trichloroacetimidate group, an acyl, formyl, sulfonyl, sulfinyl, tert-butyldiphenylsilyl group, an allyl, ester, amide, thioamide, sulfonamide group, or R³ and R⁴ taken together form a divalent radical of formula —R³—R⁴—, wherein —R³—R⁴—represents an isopropylidene, benzylidene, diphenyl methylidene, cyclohexyl methylidene group, and their substituted analogues or a linear alkylene group, and R⁵ represents a hydrogen atom or a hydrocarbon group substituted with one or more heteroatoms selected from oxygen, sulfur or nitrogen atoms, provided that the compound of formula (1) is not:

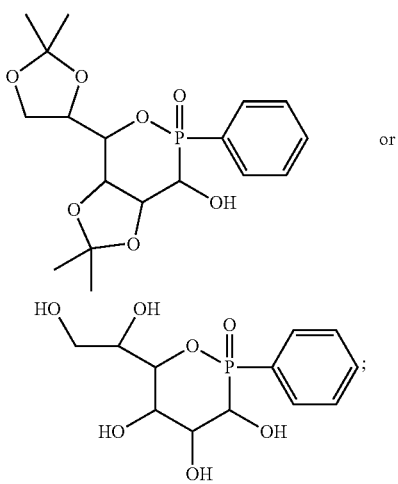

and in combination with one or more pharmaceutically acceptable excipients and/or vehicles.

8. A method of treating glioblastoma comprising administering to a subject in need thereof an effective amount of at least one compound of formula (1):

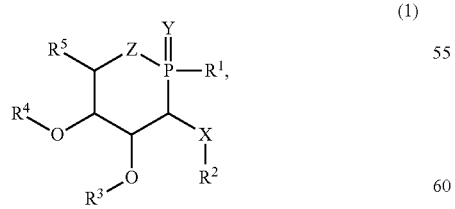

(1)

wherein:

Y represents an oxygen or a sulfur atom,

Z represents O or S, R¹ represents a hydrogen atom, an optionally substituted alkyl group or an aryl group, X represents an oxygen, a sulfur, a NH or NR⁷ group, wherein R⁷ is an optionally substituted alkyl group or an aryl group, and R² represents an aryl group, an optionally substituted alkyl group, a hydrogen atom, a trichloroacetimidate group (—C(=NH)CCl₃), an acyl, formyl, sulfonyl, sulfinyl, tert-butyldiphenylsilyl, allyl group, a saccharyl, ester, amide, thioamide, sulfonamide group, or X—R² represents a P(O)R²'R⁶' group, wherein R²' and R⁶' represent independently from each other an aryl group, an optionally substituted alkyl group, OH, an alkoxy or an aryloxy group, R³ and R⁴ represent, independently from each other an aryl group, an optionally substituted alkyl group, a hydrogen atom, a trichloroacetimidate group, an acyl, formyl, sulfonyl, sulfinyl, tert-butyldiphenylsilyl group, an allyl, ester, amide, thioamide, sulfonamide group, or R³ and R⁴ taken together form a divalent radical of formula —R³—R⁴—, wherein —R³—R⁴—represents an isopropylidene, benzylidene, diphenyl methylidene, cyclohexyl methylidene group, and their substituted analogues or a linear alkylene group, and R⁵ represents a hydrogen atom or a hydrocarbon group substituted with one or more heteroatoms selected from oxygen, sulfur or nitrogen atoms.

9. The method according to claim 8, wherein the at least one compound is administered as part of a pharmaceutical composition.

10. The compound according to claim 1, wherein X=NH.

11. The compound according to claim 10, wherein X—R² is NHC(O)R¹², wherein R¹² represents an aryl group or an optionally substituted alkyl group.

12. The compound according to claim 1, wherein R² is an ayrl group.

13. The compound according to claim 12, wherein R² is a heteroayrl group.

14. The drug according to claim 6, wherein the compound has a formula selected from the group consisting of:

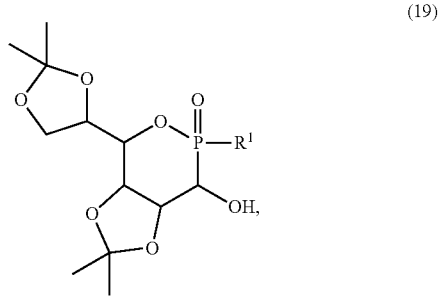

(19)

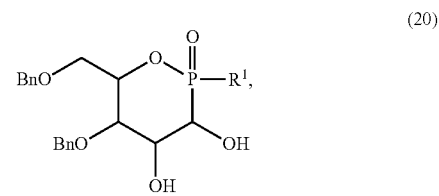

(20)

-continued

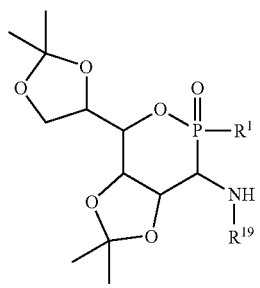
(22)

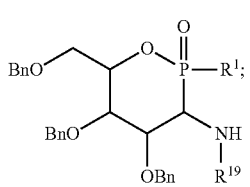
(23)

and wherein $R^1$ is as defined in claim 6, Bn represents a benzyl group, and $R^{19}$ represents a hydrogen atom, an aryl group or an optionally substituted alkyl group.

15. The drug according to claim 6, wherein the compound has a formula according to one of:

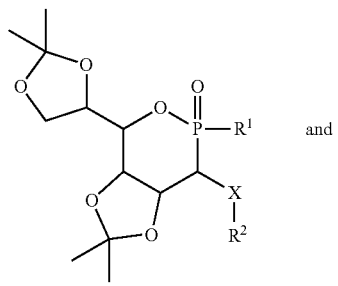
(1a)

(1b)

and wherein $R^1$, $R^2$ and X are such as defined in claim 6, and Bn represents the benzyl group.

16. The pharmaceutical composition according to claim 7, wherein the compound has a formula selected from the group consisting of:

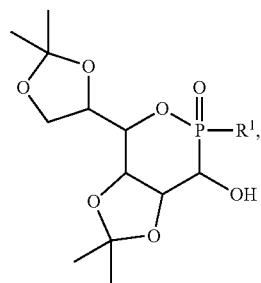
(19)

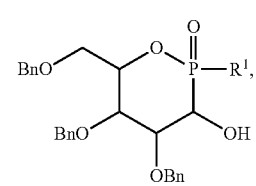
(20)

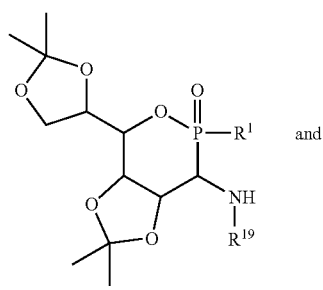
(22)

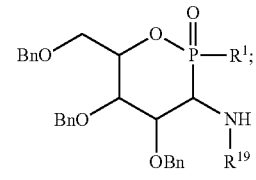
(23)

and wherein $R^1$ is as defined in claim 7, Bn represents a benzyl group, and $R^{19}$ represents a hydrogen atom, an aryl group or an optionally substituted alkyl group.

17. The pharmaceutical composition according to claim 7, wherein the compound has a formula according to one of:

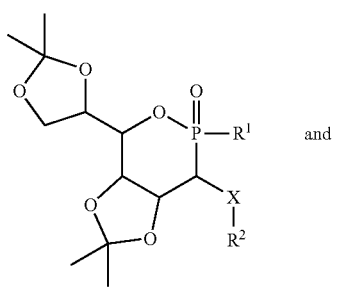
(1a)

and

-continued (1b)
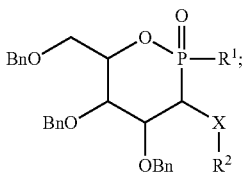

and
wherein $R^1$, $R^2$ and X are such as defined in claim 7, and Bn represents the benzyl group.

18. The method of claim 8, wherein the compound has a formula selected from the group consisting of:

(19)
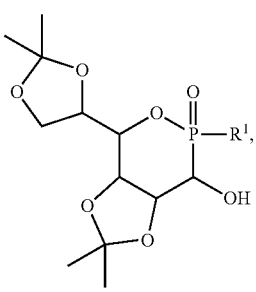

(20)
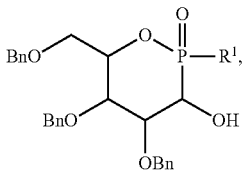

(22)
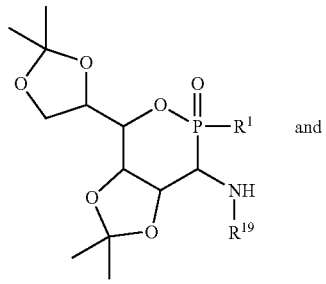

(23)
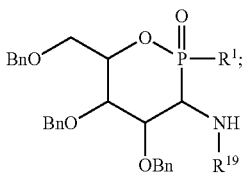

and
wherein $R^1$ is as defined in claim 9, Bn represents a benzyl group, and $R^{19}$ represents a hydrogen atom, an aryl group or an optionally substituted alkyl group.

19. The method according to claim 8, wherein the compound has a formula according to one of:

(1a)
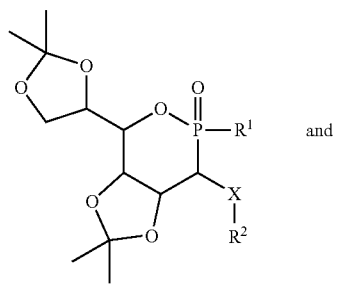

and (1b)
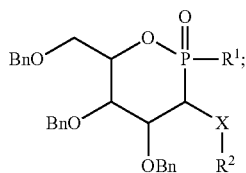

and wherein $R^1$, $R^2$ and X are such as defined in claim 8, and Bn represents the benzyl group.

20. The compound according to claim 1, further defined as having one of formula (2) and formula (3):

(2)
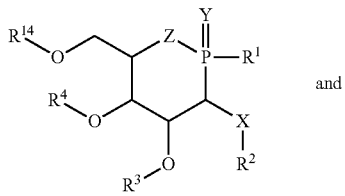

and (3)
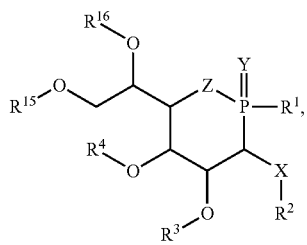

wherein $R^1$, $R^2$, $R^3$, $R^4$, X, Y and Z are as defined in claim 1, $R^{14}$, $R^{15}$ and $R^{16}$ represent, independently from each other, a hydrogen atom, an aryl, an optionally substituted alkyl group, a trichloroacetimidate group, an acyl, formyl, sulfonyl, sulfinyl, tert-butyldiphenylsilyl group, an allyl, ester, amide, thioamide, sulfonamide group, or $R^{15}$ and $R^{16}$, taken together, form a divalent radical of formula —$R^{15}$—$R^{16}$—, with the proviso that $R^{14}$ is not H.

\* \* \* \* \*